United States Patent
Minskoff et al.

(10) Patent No.: US 9,867,913 B2
(45) Date of Patent: Jan. 16, 2018

(54) SUCTION DEVICE FOR SURGICAL INSTRUMENTS

(71) Applicant: Conmed Corporation, Utica, NY (US)

(72) Inventors: Noah Mark Minskoff, Palo Alto, CA (US); James Jackson, Victoria (CA); Elisabeth Jacques Leeflang, San Francisco, CA (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 14/945,367

(22) Filed: Nov. 18, 2015

(65) Prior Publication Data

US 2016/0114086 A1   Apr. 28, 2016

Related U.S. Application Data

(63) Continuation of application No. 14/921,944, filed on Oct. 23, 2015, now Pat. No. 9,486,562.

(60) Provisional application No. 62/068,156, filed on Oct. 24, 2014, provisional application No. 62/243,422, filed on Oct. 19, 2015.

(51) Int. Cl.
| | |
|---|---|
| *A61M 35/00* | (2006.01) |
| *A61M 1/00* | (2006.01) |
| *A61B 18/14* | (2006.01) |
| *A61M 37/00* | (2006.01) |
| *A61M 5/00* | (2006.01) |
| *A61M 29/00* | (2006.01) |
| *A61M 25/00* | (2006.01) |

(52) U.S. Cl.
CPC ........... *A61M 1/0031* (2013.01); *A61B 18/14* (2013.01); *A61M 1/0035* (2014.02); *A61M 1/0064* (2013.01); *A61M 1/0076* (2013.01); *A61B 2218/007* (2013.01); *A61B 2218/008* (2013.01); *A61M 1/0056* (2013.01)

(58) Field of Classification Search
CPC ........ A61M 35/00; A61M 37/00; A61M 5/00; A61M 29/00; A61M 25/00; A61M 1/00
See application file for complete search history.

(56) References Cited

U.S. PATENT DOCUMENTS

| | | |
|---|---|---|
| 2,055,577 A | 9/1936 | Huff |
| 2,713,510 A | 7/1955 | Coanda |
| 2,773,251 A | 12/1956 | Snyder |

(Continued)

FOREIGN PATENT DOCUMENTS

| | | |
|---|---|---|
| EP | 1757317 A1 | 2/2007 |
| EP | 1909864 A2 | 4/2008 |

(Continued)

OTHER PUBLICATIONS

Chegg Study, 2003.*

(Continued)

*Primary Examiner* — Tatyana Zalukaeva
*Assistant Examiner* — Ilya Treyger
(74) *Attorney, Agent, or Firm* — Frederick J M Price; Bond, Schoeneck & King, PLLC

(57) ABSTRACT

A suction device is shown and described. The suction device includes a body, an input port configured to receive a flow of matter, a suction port, and a suction lumen that couples the suction port to the input port. In some embodiments the suction device is configured to couple with a surgical instrument for use in a surgical procedure.

24 Claims, 52 Drawing Sheets

(56) References Cited

U.S. PATENT DOCUMENTS

| | | |
|---|---|---|
| 3,494,360 A | 2/1970 | Raymond |
| 3,499,393 A | 3/1970 | John |
| 3,665,682 A | 5/1972 | Anthony et al. |
| 3,667,069 A | 6/1972 | Perry et al. |
| 3,812,855 A | 5/1974 | Banko |
| 4,654,029 A | 3/1987 | D'Antonio |
| 4,838,281 A | 6/1989 | Rogers et al. |
| 5,055,100 A | 10/1991 | Olsen |
| 5,108,389 A | 4/1992 | Cosmescu |
| 5,154,709 A | 10/1992 | Johnson |
| 5,199,944 A | 4/1993 | Cosmescu |
| 5,255,412 A | 10/1993 | Mally et al. |
| 5,318,516 A | 6/1994 | Cosmescu |
| 5,431,650 A | 7/1995 | Cosmescu |
| 5,460,602 A | 10/1995 | Shapira |
| 5,693,044 A | 12/1997 | Cosmescu |
| 5,836,944 A | 11/1998 | Cosmescu |
| 5,853,384 A | 12/1998 | Bair |
| 5,971,956 A | 10/1999 | Epstein |
| 6,149,648 A | 11/2000 | Cosmescu |
| 6,203,321 B1 | 3/2001 | Helmer et al. |
| 6,355,034 B2 | 3/2002 | Cosmescu |
| 6,368,309 B1 | 4/2002 | Yeh |
| 6,458,125 B1 | 10/2002 | Cosmescu |
| 6,599,277 B2 | 7/2003 | Neubert |
| 6,604,694 B1 | 8/2003 | Kordas et al. |
| 6,635,034 B1 | 10/2003 | Cosmescu |
| 6,702,812 B2 | 3/2004 | Cosmescu |
| 7,112,199 B2 | 9/2006 | Cosmescu |
| 7,276,063 B2 | 10/2007 | Davison et al. |
| 7,935,109 B2 | 5/2011 | Cosmescu |
| 8,092,166 B2 | 1/2012 | Nicolas et al. |
| 8,308,445 B2 | 11/2012 | Gammack et al. |
| 8,403,650 B2 | 3/2013 | Gammack et al. |
| 8,414,576 B2 | 4/2013 | Cosmescu |
| 8,439,874 B2 | 5/2013 | Hertweck |
| 8,518,018 B2 | 8/2013 | Minskoff et al. |
| 8,596,990 B2 | 12/2013 | Schaaf |
| 8,613,601 B2 | 12/2013 | Helps |
| 8,721,595 B2 | 5/2014 | Stiehl et al. |
| 8,764,412 B2 | 7/2014 | Gammack et al. |
| 8,827,945 B2 | 9/2014 | Baker et al. |
| 8,845,616 B2 | 9/2014 | Minskoff et al. |
| 8,932,286 B2 | 1/2015 | Terry et al. |
| 8,932,292 B2 | 1/2015 | Terry et al. |
| 9,023,002 B2 | 5/2015 | Robinson et al. |
| 9,119,907 B2 | 9/2015 | Sherman et al. |
| 2007/0016136 A1 | 1/2007 | Opie |
| 2007/0129722 A1 | 6/2007 | Cosmescu |
| 2007/0249990 A1 | 10/2007 | Cosmescu |
| 2007/0259226 A1 | 11/2007 | Sang et al. |
| 2010/0094283 A1 | 4/2010 | Cosmescu |
| 2010/0241026 A1 | 9/2010 | Boukas |
| 2012/0114513 A1 | 5/2012 | Simmonds et al. |
| 2012/0203209 A1 | 8/2012 | Minskoff et al. |
| 2012/0203223 A1 | 8/2012 | Terry et al. |
| 2013/0053795 A1 | 2/2013 | Coulthard et al. |
| 2013/0053796 A1 | 2/2013 | Robinson et al. |
| 2013/0131580 A1 | 5/2013 | Blackhurst et al. |
| 2013/0150782 A1 | 6/2013 | Sorensen et al. |
| 2013/0276751 A1 | 10/2013 | Raasch |
| 2014/0228839 A1 | 8/2014 | Cosmescu |
| 2015/0088132 A1 | 3/2015 | Minskoff et al. |
| 2015/0088133 A1 | 3/2015 | Minskoff et al. |
| 2015/0088134 A1 | 3/2015 | Minskoff et al. |
| 2015/0094718 A1 | 4/2015 | Minskoff et al. |
| 2015/0157773 A1 | 6/2015 | Baker et al. |

FOREIGN PATENT DOCUMENTS

| | | |
|---|---|---|
| EP | 2548537 A2 | 1/2013 |
| EP | 2977613 A1 | 1/2016 |
| WO | WO-9623448 A1 | 8/1996 |
| WO | WO-9714364 A1 | 4/1997 |
| WO | WO-2009054732 A1 | 4/2009 |
| WO | WO-2012106543 A1 | 8/2012 |

OTHER PUBLICATIONS

U.S. Appl. No. 14/921,944 Office Action dated Mar. 15, 2016.
U.S. Appl. No. 14,945,368 Office Action dated Mar. 17, 2016.
U.S. Appl. No. 14/945,370 Office Action dated Mar. 15, 2016.
Integrated Surgical, Inc. "Pulse" FTO Review. Powerpoint presentation dated Apr. 29, 2016 (21 pgs.).
Co-pending U.S. Appl. No. 14/921,944, filed Oct. 23, 2015.
Co-pending U.S. Appl. No. 14/945,366, filed Nov. 18, 2015.
Co-pending U.S. Appl. No. 14/945,368, filed Nov. 18, 2015.
Co-pending U.S. Appl. No. 14/945,370, filed Nov. 18, 2015.
PCT/US2015/57241 International Search Report and Written Opinion dated Jan. 8, 2016.
Co-pending U.S. Appl. No. 14/887,191, filed Oct. 19, 2015.
Co-pending U.S. Appl. No. 14/938,731, filed Nov. 11, 2015.
Co-pending U.S. Appl. No. 14/938,733, filed Nov. 11, 2015.
Co-pending U.S. Appl. No. 14/938,736, filed Nov. 11, 2015.
Co-pending U.S. Appl. No. 14/938,742, filed Nov. 11, 2015.
PCT/US2015/056276 International Search Report and Written Opinion dated Jan. 28, 2016.
U.S. Appl. No. 14/887,191 Office Action dated May 23, 2016.
U.S. Appl. No. 14/921,944 Office Action dated Jun. 29, 2016.
U.S. Appl. No. 14/938,731 Office Action dated Aug. 16, 2016.
U.S. Appl. No. 14/938,733 Office Action dated Aug. 15, 2016.
U.S. Appl. No. 14/938,742 Office Action dated Aug. 23, 2016.
U.S. Appl. No. 14/945,366 Office Action dated Jul. 14, 2016.
U.S. Appl. No. 14/887,191 Office Action dated Dec. 1, 2016.
U.S. Appl. No. 14/938,736 Office Action dated Sep. 8, 2016.
U.S. Appl. No. 14/945,368 Office Action dated Jan. 3, 2017.
U.S. Appl. No. 14/945,370 Office Action dated Dec. 30, 2016.

\* cited by examiner

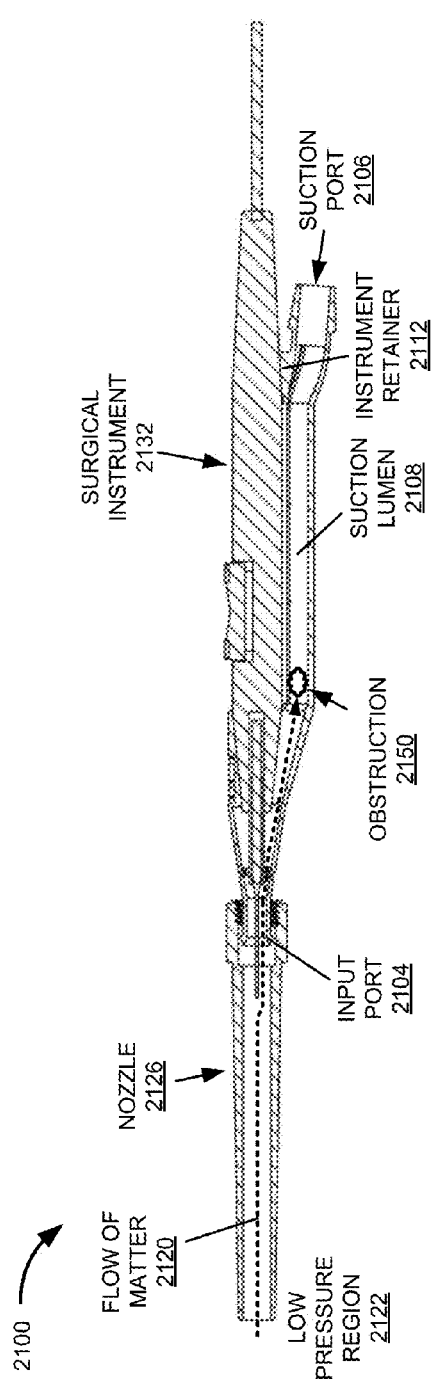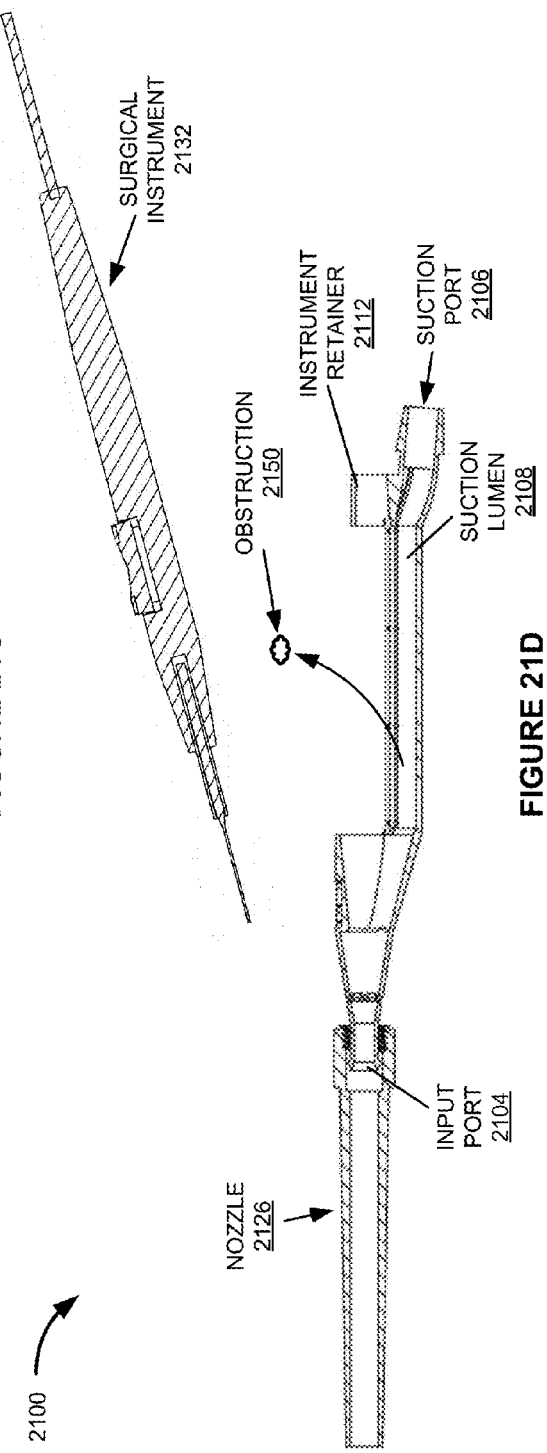
FIGURE 21C
FIGURE 21D

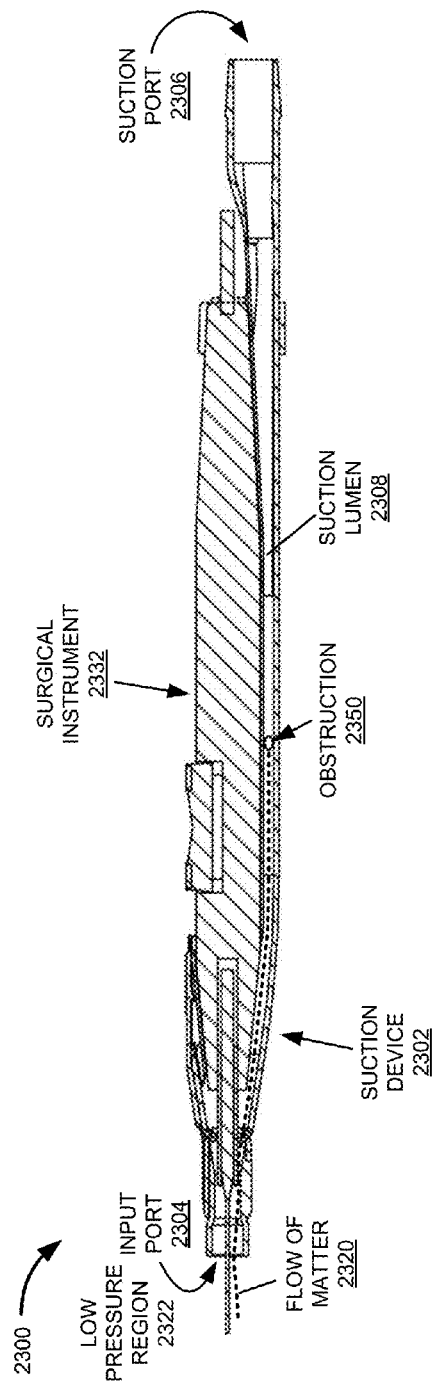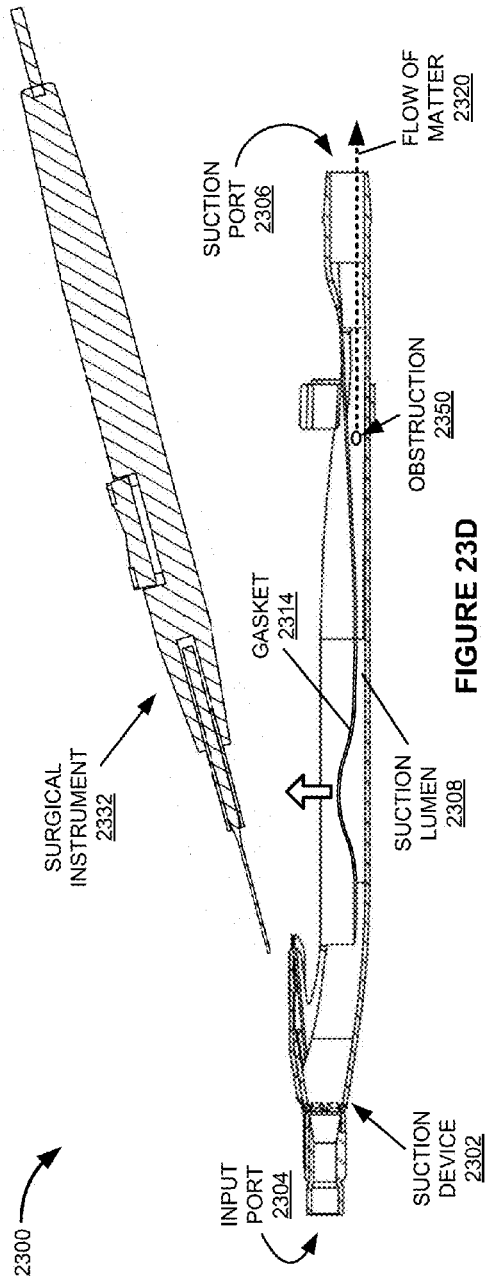
FIGURE 23C
FIGURE 23D

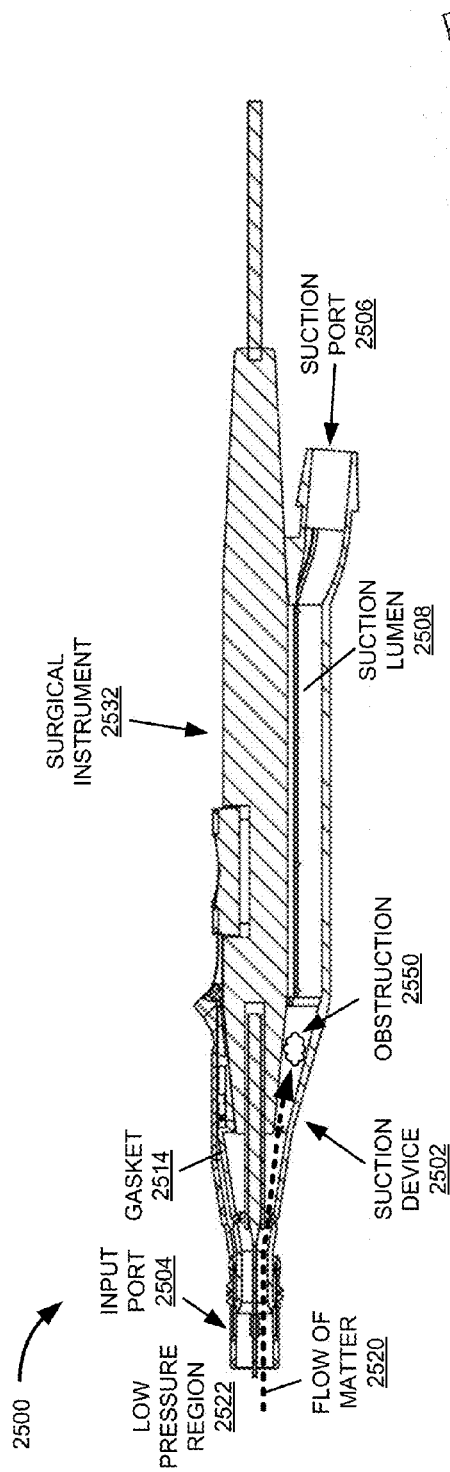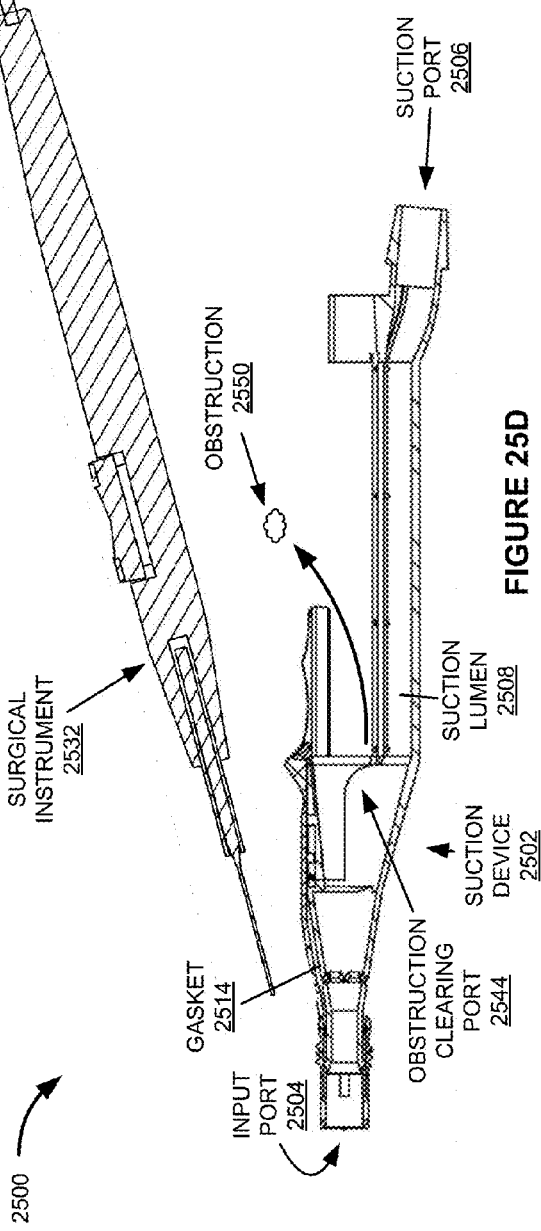
FIGURE 25C
FIGURE 25D

SUCTION DEVICE FOR SURGICAL INSTRUMENTS

CROSS-REFERENCE

This application is a continuation of U.S. patent application Ser. No. 14/921,944 filed Oct. 23, 2015 which claims the benefit of U.S. Provisional Application No. 62/068,156, filed Oct. 24, 2014, as well as U.S. Provisional Application No. 62/243,422, filed Oct. 19, 2015, which applications are both incorporated entirely herein by reference.

BACKGROUND

Simultaneous removal of gas and fluid from a field, such as a surgical field, is important to reduce exposure to hazardous byproducts and increase user visibility. Current surgical devices poorly handle suctioning of a flow of matter comprising both gas and liquid components.

SUMMARY

Described herein are devices, systems, and methods for suctioning a flow of matter from a field, such as a surgical field.

An aspect of the present disclosure provides a suction device comprising: (a) a body configured to couple with or integral thereto a surgical instrument; (b) an input port disposed towards the distal end of the body, configured to receive a flow of matter; (c) an suction port disposed towards the proximal end of the body, configured to couple to a suction source; (d) a suction lumen disposed within the body that couples the input port to the suction port; and (e) one or more intake ports in fluid communication with the suction lumen disposed towards the distal end of the body.

In some embodiments, the suction device further comprises an instrument retainer configured to couple the surgical instrument to the body and a gasket disposed within the body and configured to provide a seal between the suction device and the surgical instrument. In some embodiments, the body is configured to couple with the surgical instrument. In some embodiments, the one or more intake ports are disposed between the input port and the suction port, are disposed on the input port, or a combination thereof.

In some embodiments, the suction device further comprises a suction control. In some embodiments, the suction control is configured to be adjustable by a user. In some embodiments, the suction control adjusts the suction capacity at the input port. In some embodiments, the suction control comprises a sliding member configured to be adjustable by a user. In some embodiments, the sliding member adjusts a gas evacuation, a liquid evacuation, or a combination thereof at the input port. In some embodiments, the suction control comprises detents configured to locate the suction control in user controlled positions. In some embodiments, the suction control is configured to locate the suction control in a user controlled position using friction. In some embodiments, the suction control is integral to the gasket. In some embodiments, the gasket comprises a flexible membrane configured to permit a user to manipulate the flexible membrane to clear an obstruction.

In some embodiments, the suction lumen comprises an open portion that is closed by attachment of the surgical instrument, configured to permit a user to detach the surgical instrument and remove an obstruction from the suction device.

In some embodiments, the suction device further comprises a positive pressure operated fluid accelerator disposed near the distal end of the body, configured to take advantage of the Coanda effect to generate suction near the input port.

In some embodiments, the suction device further comprises a nozzle adapter configured to attach and detach nozzles without the use of tools or other devices. In some embodiments, the suction device further comprises a nozzle. In some embodiments, the nozzle includes the one or more intake ports.

In some embodiments, the suction device further comprises a suction control configured to open and close at least one of the one or more intake ports to vary the flow of matter of liquids, solids or gasses suctioned by the suction device.

In some embodiments, the input port, the one or more intake ports, or a combination thereof comprise a double scallop shape. In some embodiments, the one or more intake ports disposed between the input port and the suction port are configured to take advantage of the Venturi effect. In some embodiments, the suction lumen comprises a narrowing between the input port and the suction port. In some embodiments, the one or more intake ports disposed between the input port and the suction port are fluidically coupled to the suction lumen at the narrowing. In some embodiments, the one or more intake ports disposed between the input port and the suction port are positioned a) circumferentially around the suction lumen at the narrowing, b) in series along the suction lumen at the narrowing or c) a combination thereof. In some embodiments, the one or more intake ports disposed between the input port and the suction port are fluidically coupled to the suction lumen at a point of maximum pressure differential of the flow of matter within the suction lumen. In some embodiments, the one or more intake ports disposed between the input port and the suction port are fluidically coupled to the suction lumen at a narrowest point within the suction lumen.

In some embodiments, a shape of the suction lumen enhances a laminar profile of the flow of matter through the suction lumen. In some embodiments, the shape is an edge of the one or more intake ports in fluidic communication with the suction lumen. In some embodiments, the edge forms an angle of less than 90 degrees relative to the body.

In some embodiments, the suction device further comprises a filter attachable to the suction device. In some embodiments, the filter substantially covers the one or more intake ports. In some embodiments, the filter prevents solids from entering the suction lumen via the one or more intake ports. In some embodiments, the filter comprises a pore size of 100 micrometers or less.

In some embodiments, the suction device further comprises an emulsion segment positioned between the input port and the one or more intake ports disposed between the input port and the suction port. In some embodiments, the emulsion segment comprises an inner lumen and an outer lumen. In some embodiments, the inner lumen comprises one or more holes through which a least a portion of the flow of matter passes. In some embodiments, the one or more holes are spaced toroidally or helically along a length of the inner lumen.

Another aspect of the present disclosure provides a method for providing suction to a surgical field. The method comprises providing a suction device comprising (a) a body configured to couple with or integral thereto a surgical instrument; (b) an input port disposed towards the distal end of the body, configured to receive a flow of matter; (c) an suction port disposed towards the proximal end of the body, configured to couple to a suction source; (d) a suction lumen disposed within the body that couples the input port to the suction port; and (e) one or more intake ports in fluid communication with the suction lumen disposed towards the distal end of the body.

In some embodiments, the suction device further comprises an instrument retainer configured to couple the surgical instrument to the body and a gasket disposed within the body and configured to provide a seal between the suction device and the surgical instrument. In some embodiments, the body is attachable to the surgical instrument. In some embodiments, the one or more intake ports are disposed between the input port and the suction port, are disposed on the input port, or a combination thereof.

In some embodiments, the suction device generates at least a 3 fold greater suction capacity at the input port compared to a suction device without the one or more intake ports disposed between the input port and the suction port. In some embodiments, the suction device generates at least a 2 fold greater suction area at the input port compared to a suction device without the one or more intake ports disposed between the input port and the suction port.

In some embodiments, the suction device further comprises an emulsion segment positioned between the input port and the one or more intake ports disposed between the input port and the suction port. In some embodiments, the emulsion segment comprises an inner lumen and an outer lumen. In some embodiments, the inner lumen comprises one or more holes. In some embodiments, the method further comprises passing at least a portion of the flow of matter through the one or more holes thereby frothing a liquid portion of the flow of matter.

In some embodiments, the method further comprises adjusting a suction capacity at the input port using a suction control. In some embodiments, the method further comprises adjusting a gas suction, a liquid suction, or combination thereof at the input port using a sliding member.

In some embodiments, the method further comprises manipulating a gasket to free an obstruction. In some embodiments, the method further comprises removing an obstruction through an obstruction clearing port included in a gasket.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the subject matter described herein are set forth with particularity in the appended claims. A better understanding of the features and advantages of the present subject matter will be obtained by reference to the following detailed description that sets forth illustrative embodiments, in which the principles of the subject matter described herein are utilized, and the accompanying drawings of which:

FIG. 21C is a diagram illustrating the operation of a suction device with surgical instrument in the event of an obstruction.

FIG. 21D is a diagram illustrating the operation of clearing a suction device with surgical instrument.

FIG. 23C is a diagram illustrating the operation of a suction device with surgical instrument in the event of an obstruction.

FIG. 23D is a diagram illustrating the operation of clearing a suction device with surgical instrument.

FIG. 25C is a diagram illustrating the operation of a suction device with surgical instrument in the event of an obstruction.

FIG. 25D is a diagram illustrating the operation of clearing a suction device with surgical instrument.

DETAILED DESCRIPTION

Figure 1:
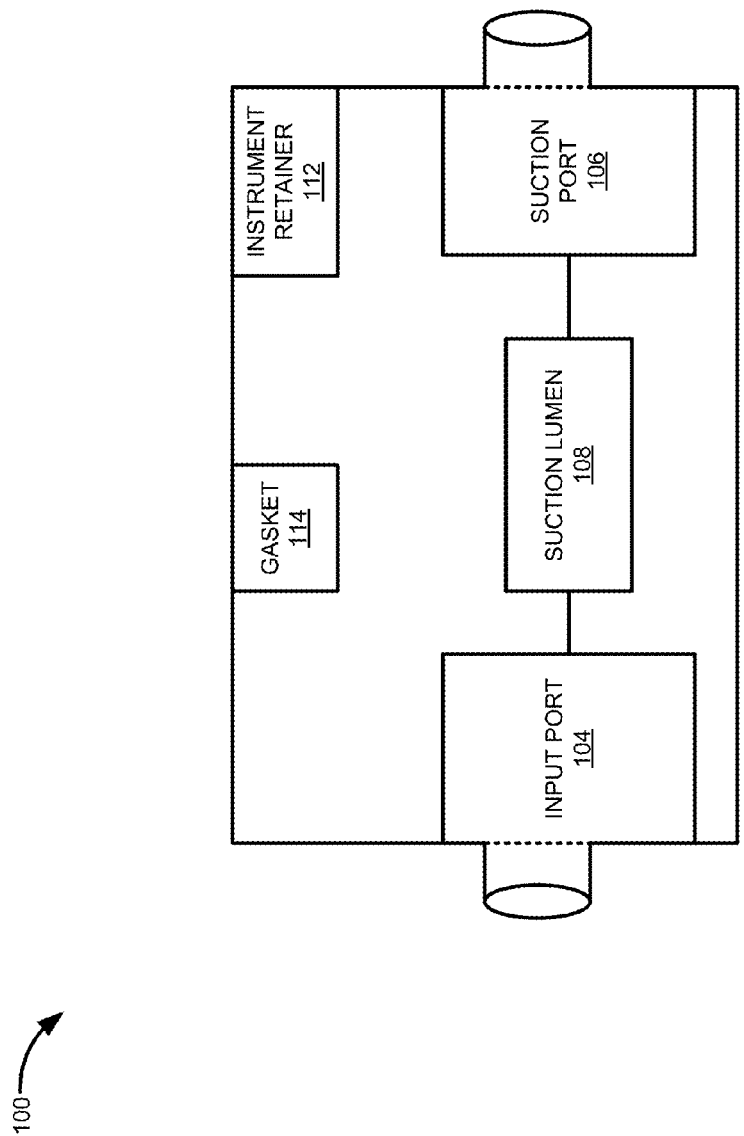
FIG. 1 is a block diagram illustrating a suction device.

Described herein are devices, methods, and systems for a suction device. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details.

The term "about" means the referenced numeric indication plus or minus 15% of that referenced numeric indication.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The term "subject" as used herein may refer to a human subject or any animal subject.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

A suction device is shown and described. The suction device includes a body configured to attach to a surgical instrument. In some embodiments, the body may be configured for handheld operation. In some embodiments, the body may be configured to attach to a surgical instrument. The suction device includes an input port disposed towards the distal end of the body configured to receive a flow of matter. The suction device includes a suction port disposed towards the proximal end of the body configured to couple to a suction source. The suction device includes a suction lumen disposed within the body that couples the input port to the suction port. The suction device includes an instrument retainer configured to couple the surgical instrument to the body. The suction device includes a gasket disposed within the body and configured to provide a seal between the suction device and the surgical instrument.

In some embodiments, the suction device may include a suction control configured for a user input to control suction at an input port. In some embodiments, the suction control may include a sliding member configured to receive a user input. In some embodiments, the suction control may include detents configured to locate the suction control in predetermined positions. In some embodiments, the suction control may use friction supplied by a gasket to locate the suction control in predetermined positions. In some embodiments, a suction lumen may include a gasket comprising a flexible membrane disposed between the suction lumen and the surgical instrument configured to permit a user to detach the surgical instrument and manipulate the flexible membrane to clear an obstruction. In some embodiments, the suction lumen may include an open portion that is closed by attachment of a surgical instrument configured to permit a user to detach the surgical instrument and remove an obstruction. In some embodiments, a suction device may include suction ports are configured to utilize the Venturi effect. In some embodiments, a suction device may include a positive pressure operated suction element located near the distal end of the body configured to generate suction at an input port using the Coanda effect. In some embodiments, a suction device may include a nozzle adapter configured to accept different nozzles. In some embodiments, the nozzle may include suction ports disposed near the distal end of the nozzle. In some embodiments, a suction device may include a suction control configured to close the suction ports in the suction device and open the suction ports disposed near the distal end of the nozzle.

FIG. 1 is a block diagram illustrating suction device 100. Suction device 100 includes input port 104, suction port 106, suction lumen 108, instrument retainer 112 and gasket 114. Suction device 100 is configured to suction matter. The matter may include liquids, solids and gasses. The matter may also include surgical byproducts, smoke and noxious aerosols. Suction device 100 is configured to couple to a suction source. The suction source may be a vacuum pump, aspirator, positive pressure operated suction source configured to take advantage of the Coanda effect, or some other means of generating suction. The suction source generates a low pressure region near input port 104. The low pressure region is at a pressure below the ambient air pressure, thus causing a flow of matter to be pulled into input port 104. In some embodiments, suction device 100 may be configured to couple to a surgical instrument via instrument retainer 112. Some surgical instruments that may benefit from suction device 100 include electrosurgical instruments using heat conduction, diathermy, radio-frequency, and laser methods of operation.

Suction device 100 includes input port 104. Input port 104 is configured to receive a flow of matter. The flow of matter may include liquids, gasses and solids. The flow of matter may include bodily fluids, surgical byproducts and smoke. Input port 104 is configured to supply flow of matter 120 to suction lumen 108 Input port 104 is disposed towards the distal end of suction device 100. Input port 104 is coupled to suction lumen 108. In some embodiments, input port 104 may include a positive pressure operated suction device configured to take advantage of the Coanda effect.

Suction device 100 includes suction port 106. Suction port 106 is configured to receive a flow of matter from suction lumen 108. Suction port 106 is also configured to expel a flow of matter. Suction port 106 is disposed at the proximal end of suction device 100. Suction port 106 is coupled to suction lumen 108. Suction port 106 may be coupled to a suction source. The suction source may include a vacuum pump, aspirator, positive pressure operation suction source configured to take advantage of the Coanda effect, or some other means of generating suction. In some embodiments, a suction system may include a separator disposed between suction port 106 and the suction source to remove waste material from a flow of matter.

Suction device 100 includes suction lumen 108. Suction lumen 108 is configured to couple input port 104 to suction port 106. Suction lumen 108 is disposed within suction device 100. In some embodiments, suction lumen 108 may be fully enclosed. In some embodiments, suction lumen 108 may include an open portion configured to allow an obstruction to be removed from suction lumen 108. The open portion may be covered and sealed by gasket 114. The open portion may also be configured to be sealed by the attachment of a surgical instrument.

Suction device 100 includes instrument retainer 112. Instrument retainer 112 is configured to couple suction device 100 to a surgical instrument. Instrument retainer 112 allows a surgical instrument to be attached and detached from suction device 100 without the use of tools. In some embodiments, instrument retainer 112 may be configured to accept a particular make and model of surgical instrument. In some embodiments, instrument retainer 112 may be configured to include a clip-type configuration to allow quick attachment and detachment of a surgical instrument without tools.

Suction device 100 includes gasket 114. Gasket 114 is configured to provide a seal between suction device 100 and a surgical instrument. Gasket 114 may prevent suction from a suction source from leaking between a suction device 100 and surgical instrument interface. In some embodiments, gasket 114 may be configured to include an obstruction clearing port configured to provide access to suction lumen 108 to remove an obstruction. This configuration allows a user to detach a surgical instrument and directly access suction lumen 108 to remove an obstruction. In some embodiments, gasket 114 may be comprises of a flexible membrane configured to be manipulated to clear an obstruction within suction lumen 108.

Figure 2:
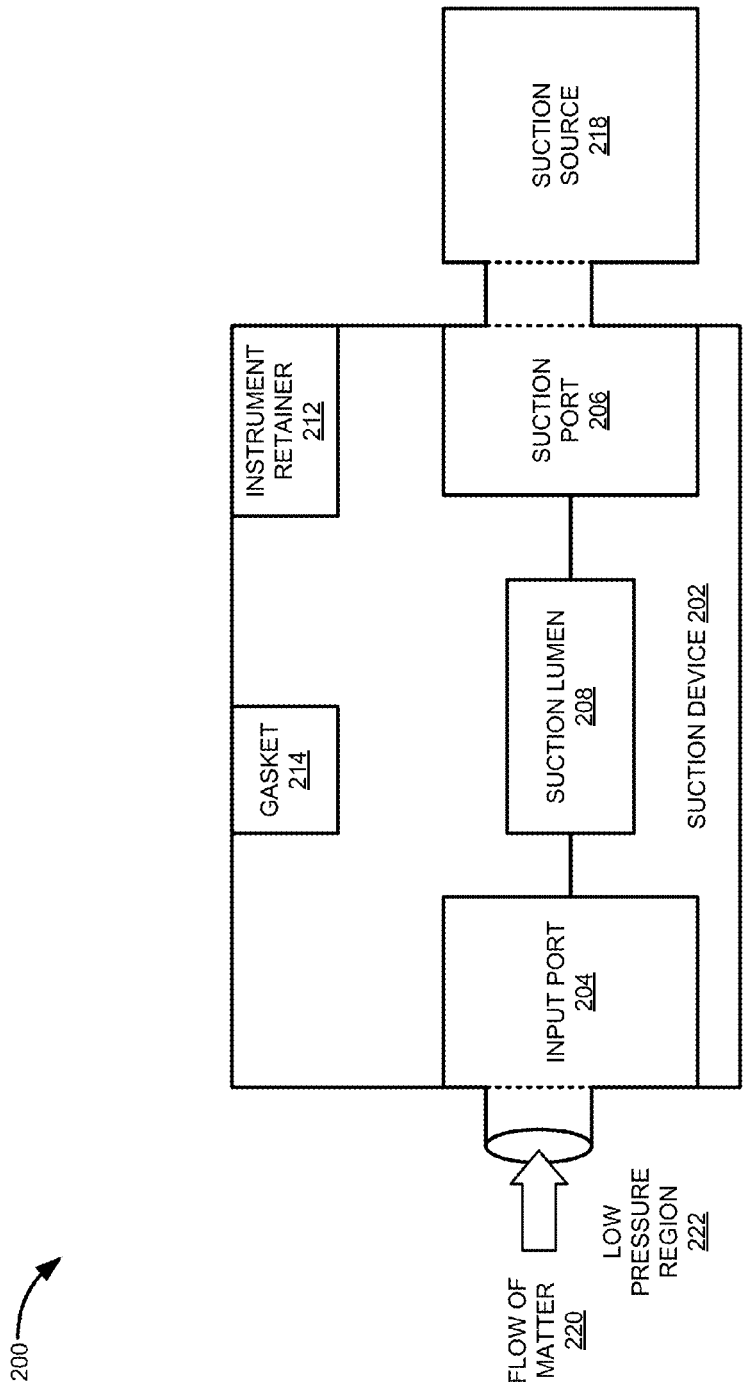
FIG. 2 is a block diagram illustrating the operation of a suction system.

FIG. 2 is a block diagram illustrating the operation of suction system 200. Suction system 200 includes suction device 202 and suction source 218. Suction device 202 is an example of suction device 100; however, suction device 202 may include alternative configurations and methods of operation. Suction device 202 includes input port 204, suction port 206, suction lumen 208, instrument retainer 212 and gasket 214.

Suction system 200 includes suction device 202. Suction device 202 is configured to suction matter. The matter may include liquids, solids and gasses. The matter may also include surgical byproducts, smoke and noxious aerosols. Suction device 202 is configured to couple to suction source 218. Suction source 218 may be a vacuum pump, aspirator, positive pressure operated suction source configured to take advantage of the Coanda effect, or some other means of generating suction. Suction source 218 generates low pressure region 222 near input port 204. Low pressure region 222 is at a pressure below the ambient air pressure, thus causing flow of matter 220 to be pulled into input port 204. In some embodiments, suction device 202 may be configured to couple to a surgical instrument via instrument retainer 212. Some surgical instruments that may benefit from suction device 202 include electrosurgical instruments using heat conduction, diathermy, radio-frequency, and laser methods of operation.

Suction device 202 includes input port 204. Input port 204 is configured to receive flow of matter 220. Flow of matter 220 may include liquids, gasses and solids. Flow of matter 220 may include bodily fluids, surgical byproducts and smoke. Input port 204 is disposed towards the distal end of suction device 202. Input port 204 is coupled to suction lumen 208. Input port 204 is configured to supply flow of matter 220 to suction lumen 208.

Suction device 202 includes suction port 206. Suction port 206 is configured to receive flow of matter 220 from suction lumen 208. Suction port 206 is disposed at the proximal end of suction device 202. Suction port 206 is coupled to suction lumen 208. Suction port 206 is configured to expel flow of matter 220. Suction port 206 is coupled to a suction source 218. Suction source 218 may include a vacuum pump, aspirator, positive pressure operation suction source configured to take advantage of the Coanda effect, or some other means of generating suction. In some embodiments, suction system 200 may include a separator disposed between suction port 206 and suction source 218 to remove waste material from flow of matter 220.

Suction device 202 includes suction lumen 208. Suction lumen 208 is configured to couple input port 204 to suction port 206. Suction lumen 208 is disposed within suction device 202. In some embodiments, suction lumen 208 may be fully enclosed. In some embodiments, suction lumen 208 may include an open portion configured to allow an obstruction to be removed from suction lumen 208.

Suction device 202 includes instrument retainer 212. Instrument retainer 212 is configured to couple suction device 202 to a surgical instrument. Instrument retainer 212 allows a surgical instrument to be attached and detached from suction device 202 without the use of tools. In some embodiments, instrument retainer 212 may be configured to accept a particular make and model of surgical instrument. In some embodiments, instrument retainer 212 may be configured to include a clip-type configuration to allow quick attachment and detachment of a surgical instrument without tools.

Suction device 202 includes gasket 214. Gasket 214 is configured to provide a seal between suction device 202 and a surgical instrument. Gasket 214 may prevent suction from a suction source from leaking between suction device 202 and a surgical instrument interface. In some embodiments, gasket 214 may include an obstruction clearing port configured to allow access to suction lumen 208 to clear an obstruction. This configuration allows a user to detach a surgical instrument and directly access suction lumen 208 to remove an obstruction. In some embodiments, gasket 214 may comprise a flexible membrane configured to be manipulated to clear an obstruction within suction lumen 208.

Suction system 200 includes suction source 218. Suction source 218 is configured to supply suction to suction device 202. Suction source may be a vacuum pump, aspirator, positive pressure operated suction source configured to take advantage of the Coanda effect, or some other means of generating suction.

Figure 3:
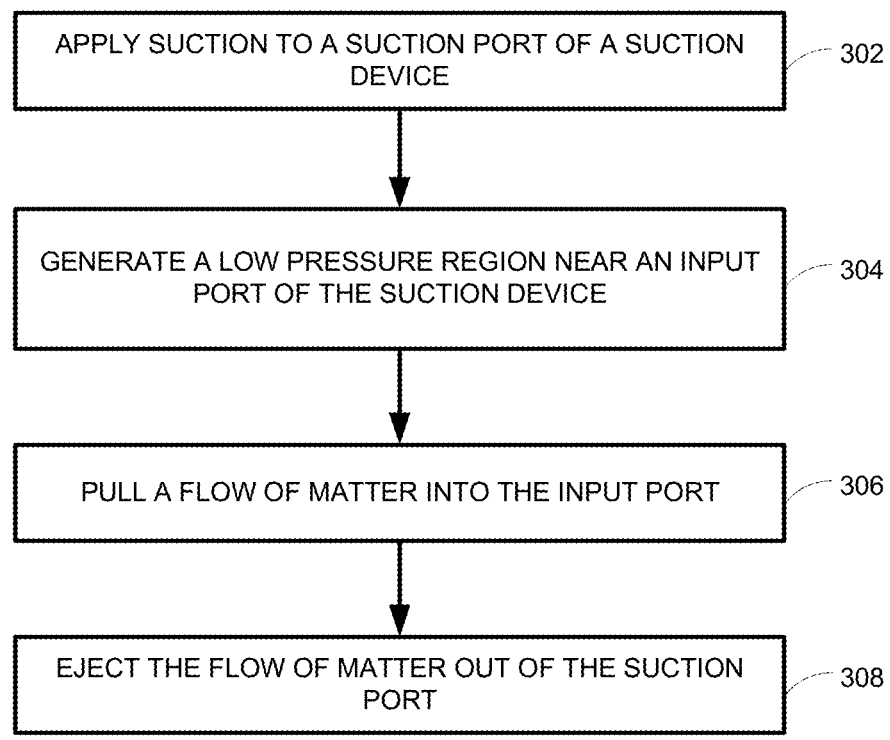
FIG. 3 is a diagram illustrating a method of operating a suction system.

FIG. 3 is a diagram illustrating a method of operating a suction device. The steps illustrated in FIG. 3 may be performed by one or more elements of suction system 200. Suction is applied to a suction port of a suction device (302). For example, suction port 206 is configured to couple to suction source 218. Suction source 218 is configured to apply suction to suction port 206 of suction device 202. A low pressure region is generated near an input port of the suction device (304). For example, input port 204 is coupled to suction port 206 via suction lumen 208. Suction from suction source 218 is used to generate low pressure region 222 near input port 204. A flow of matter is pulled into the input port (306). For example, input port 204 is configured to receive flow of matter 220. Low pressure region 222 is at a pressure below the ambient air pressure. Low pressure region 222 causes flow of matter 220 to be pulled into input port 204. The flow of matter is ejected out of the suction port (308). For example, input port 204 is coupled to suction port 206 via suction lumen 208. Suction lumen 208 is configured to supply flow of matter 220 to suction port 206. Suction port 206 is configured to eject flow of matter 220 from suction device 202.

Figure 4:
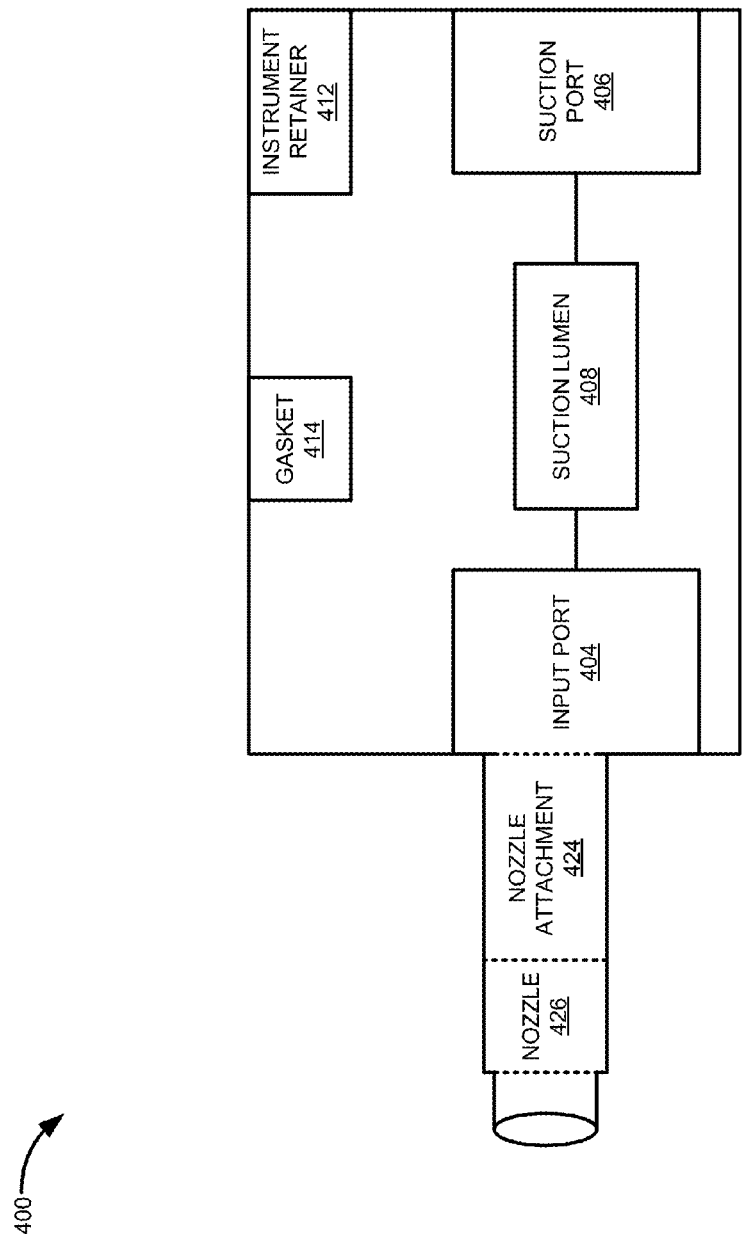
FIG. 4 is a block diagram illustrating a suction device with nozzle.

FIG. 4 is a block diagram illustrating suction device with nozzle 400. Suction device with nozzle includes suction device 402. Suction device 402 is an example of suction device 100 and suction device 202; however, suction device 402 includes nozzle attachment 424 and nozzle 426. Suction device with nozzle 400 includes input port 404, suction port 406, suction lumen 408, instrument retainer 412, gasket 414, nozzle attachment 424 and nozzle 426.

Suction device with nozzle 400 includes input port 404. Input port 404 is configured to receive a flow of matter from nozzle 426 and nozzle attachment 424. The flow of matter may include liquids, gasses and solids. The flow of matter may include bodily fluids, surgical byproducts and smoke. Input port 404 is disposed towards the distal end of suction device with nozzle 400. Input port 404 is coupled to suction lumen 408. Input port 404 is configured to supply flow of matter 420 to suction lumen 408. Input port 404 is coupled to nozzle attachment 424. In some embodiments, nozzle attachment 424 may be integral to input port 404.

Suction device with nozzle 400 includes suction port 406. Suction port 406 is configured to receive a flow of matter from suction lumen 408. Suction port 406 is coupled to suction lumen 408. Suction port 406 is disposed at the proximal end of suction device with nozzle 400. Suction port 406 is configured to expel a flow of matter. The suction source may include a vacuum pump, aspirator, positive pressure operation suction source configured to take advantage of the Coanda effect, or some other means of generating suction. Suction port 406 is configured to couple to a suction source. In some embodiments, a suction system may include a separator disposed between suction port 406 and a suction source to remove waste material from a flow of matter.

Suction device with nozzle 400 includes suction lumen 408. Suction lumen 408 is configured to couple input port 404 to suction port 406. Suction lumen 408 is disposed within suction device 402. In some embodiments, suction lumen 408 may be fully enclosed. In some embodiments, suction lumen 408 may include an open portion configured to allow an obstruction to be removed from suction lumen 408. In some embodiments, gasket 414 may be configured to cover the open portion of suction lumen 408. In some embodiments, gasket 414 may be configured to permit a user to detach a surgical instrument to manipulate gasket 414 to clear an obstruction.

Suction device with nozzle 400 includes instrument retainer 412. Instrument retainer 412 is configured to couple suction device 402 to a surgical instrument. Instrument retainer 412 allows a surgical instrument to be attached and detached from suction device 402 without the use of tools. In some embodiments, instrument retainer 412 may be configured to accept a particular make and model of surgical instrument. In some embodiments, instrument retainer 412 may be configured to include a clip-type configuration to allow quick attachment and detachment of a surgical instrument without tools.

Suction device with nozzle 400 includes gasket 414. Gasket 414 is configured to provide a seal between suction device 402 and a surgical instrument. Gasket 414 may prevent suction from a suction source from leaking between a suction device 402 and a surgical instrument interface. In some embodiments, gasket 414 may be configured to provide an obstruction clearing port configured to allow access to suction lumen 408 to clear an obstruction. This configuration allows a user to detach a surgical instrument and directly access suction lumen 408 to remove an obstruction. In some embodiments, gasket 414 may comprise a flexible membrane configured to be manipulated to clear an obstruction within suction lumen 408.

Suction device with nozzle 400 includes nozzle attachment 424. Nozzle attachment 424 is configured to accept a variety of different nozzles 426 suited for an intended application. In some embodiments, nozzle attachment 424 may include threads, Luer locks, quick-disconnect, or some other fitting configured to allow attachment of nozzle 426.

Suction device with nozzle 400 includes nozzle 426. Nozzle 426 is configured to couple to nozzle attachment 424. The shape and configuration of nozzle 426 may vary depending upon the intended application. In some embodiments, nozzle 426 may include intake ports disposed near the distal end of nozzle 426. In some embodiments, the intake ports disposed near the distal end of nozzle 426 may be variably opened or closed by a suction control. Nozzle 426 may be a commercially available nozzle.

Figure 5:
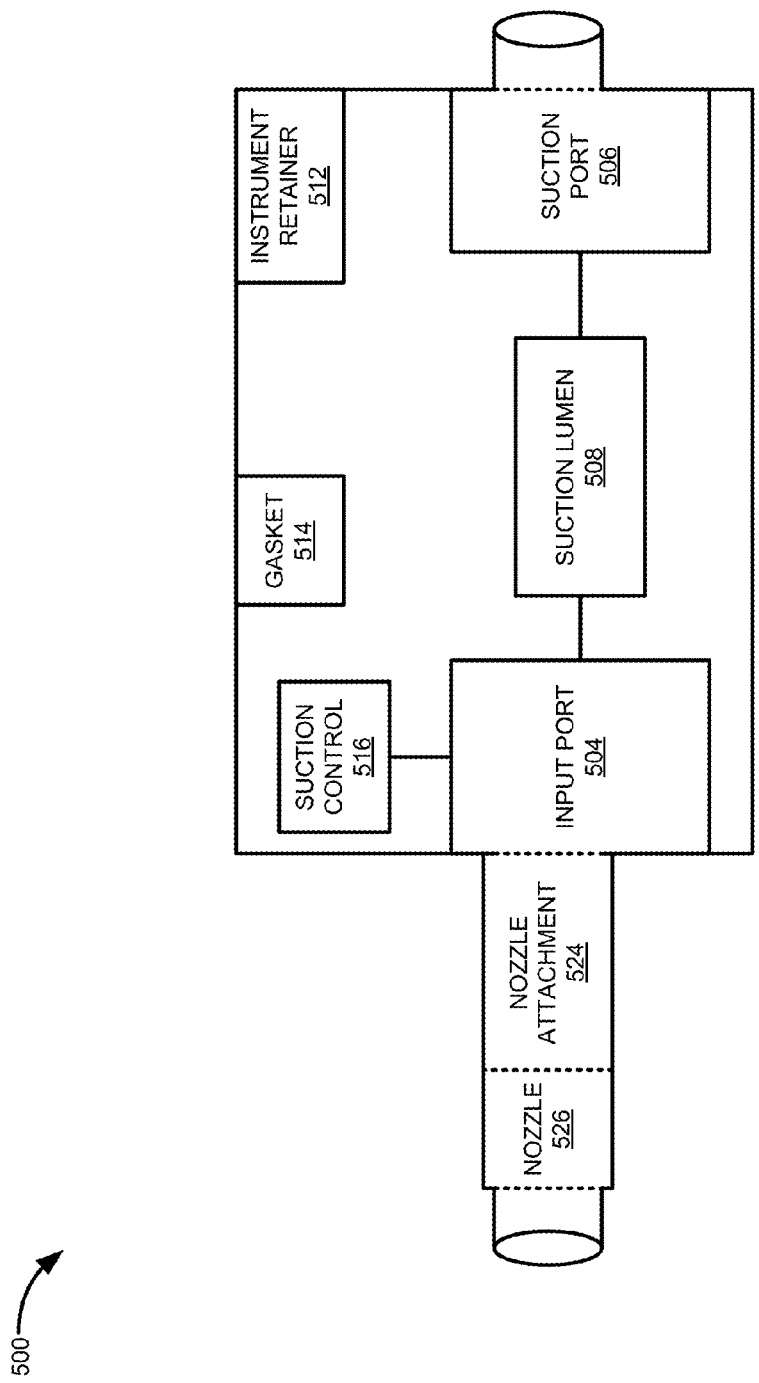
FIG. 5 is a block diagram illustrating a suction device with suction control.

FIG. 5 is a block diagram illustrating suction device with suction control 500. Suction device with suction control 500 includes suction device 502. Suction device 502 is an example of suction device 100, suction device 202 and suction device 402; however, suction device 502 includes suction control 516. Suction device with suction control 500 includes input port 504, suction port 506, suction lumen 508, instrument retainer 512, gasket 514, suction control 516, nozzle attachment 524 and nozzle 526.

Suction device with suction control 500 includes input port 504. Input port 504 is disposed towards the distal end of suction device 502. Input port 504 is coupled to nozzle attachment 524. In some embodiments, nozzle attachment 524 may be integral to input port 504. Input port 504 is coupled to suction lumen 508. Input port 504 is configured to receive a flow of matter from nozzle 526 and nozzle attachment 524. The flow of matter may include liquids, gasses and solids. The flow of matter may include bodily fluids, surgical byproducts and smoke. Input port 504 is configured to supply flow of matter 520 to suction lumen 508. In some embodiments, input port 504 may include a positive pressure operated suction source configured to take advantage of the Coanda effect.

Suction device with suction control 500 includes suction port 506. Suction port 506 is configured to couple to a suction source. The suction source may include a vacuum pump, aspirator, positive pressure operation suction source configured to take advantage of the Coanda effect, or some other means of generating suction. Suction port 506 is disposed at the proximal end of suction device 502. Suction port 506 is coupled to suction lumen 508. Suction port 506 is configured to receive a flow of matter from suction lumen 508. Suction port 506 is configured to expel a flow of matter. In some embodiments, a suction system may include a separator disposed between suction port 506 and a suction source to remove waste material from a flow of matter.

Suction device with suction control 500 includes suction lumen 508. Suction lumen 508 is configured to couple input port 504 to suction port 506. Suction lumen 508 is disposed within suction device 502. In some embodiments, suction lumen 508 may be fully enclosed. In some embodiments, suction lumen 508 may include an open portion configured to allow an obstruction to be removed from suction lumen 508.

Suction device with suction control 500 includes instrument retainer 512. Instrument retainer 512 is configured to couple suction device 502 to a surgical instrument. Instrument retainer 512 allows a surgical instrument to be attached and detached from suction device 502 without the use of tools. In some embodiments, instrument retainer 512 may be configured to accept a particular make and model of surgical instrument. In some embodiments, instrument retainer 512 may be configured to include a clip-type configuration to allow quick attachment and detachment of a surgical instrument.

Suction device with suction control 500 includes gasket 514. Gasket 514 is configured to provide a seal between suction device 502 and a surgical instrument. Gasket 514 may prevent suction from a suction source from leaking between suction device 502 and a surgical instrument interface. In some embodiments, gasket 514 may be configured to provide an obstruction clearing port configured to allow access to suction lumen 508 to clear an obstruction. This configuration allows a user to detach a surgical instrument and directly access suction lumen 508 to remove an obstruction. In some embodiments, gasket 514 may comprise a flexible membrane configured to be manipulated to clear an obstruction within suction lumen 508.

Suction device with suction control 500 includes suction control 516. Suction control 516 is configured to adjust a suction ratio of liquids, solids and gasses pulled into suction device 502. Suction control 516 may adjust a ratio of liquids, solids and gasses by adjusting the location of nozzle 526. In some embodiments, suction control 516 may be configured to adjust intake ports included at input port 504. In some embodiments, suction control 516 may be configured to adjust intake ports included at nozzle 526. In some embodiments, suction control 516 may comprise a sliding member. In some embodiments, the sliding member may be configured to extend and retract nozzle 526 in order to selectively adjust a ratio of liquids, solids and gasses suctioned by suction device 502. In some embodiments, suction control 516 may include a means for securing a location of suction control 516. The means for securing suction control 516 may include detents, friction fit, notches or some other means for securing a location of suction control 516.

Suction device with suction control 500 includes nozzle attachment 524. Nozzle attachment 524 is configured to accept a variety of different nozzles suited for an intended application. In some embodiments, nozzle attachment 524 may include threads, Luer locks, quick-disconnect, or some other fitting configured to allow attachment of nozzle 526.

Suction device with suction control 500 includes nozzle 526. Nozzle 526 is configured to couple to nozzle attachment 524. The shape and configuration of nozzle 526 may vary depending upon the intended application. In some embodiments, nozzle 522 may include intake ports disposed near the distal end of nozzle 522. In some embodiments, the intake ports disposed near the distal end of nozzle 526 may be variably opened or closed by suction control 516. Nozzle 526 may be a commercially available nozzle.

Figure 6:
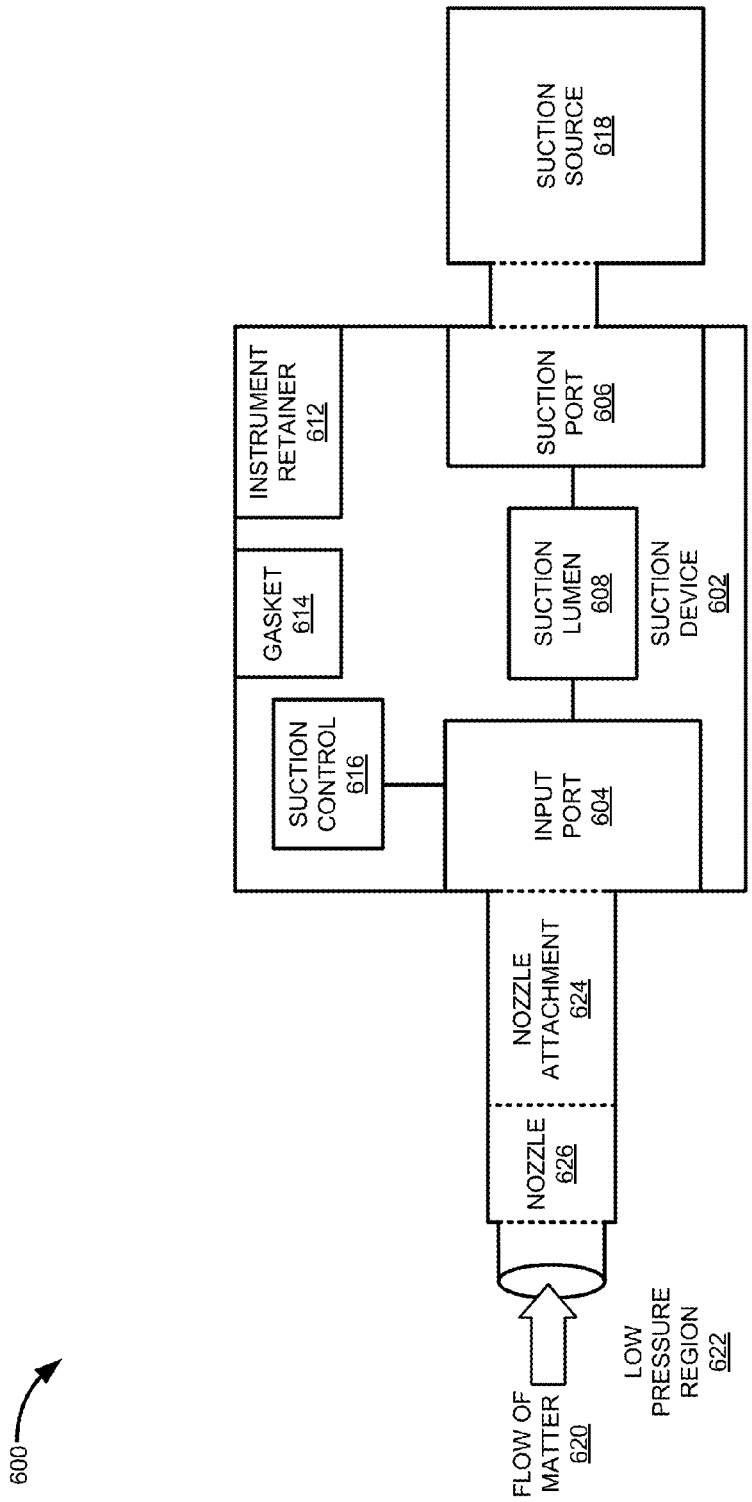
FIG. 6 is a block diagram illustrating the operation of a suction system with suction control.

FIG. 6 is a block diagram illustrating the operation of suction system with suction control 600. Suction system with suction control 600 is an example of suction system 200; however suction system with suction control 600 may include alternative configurations and methods of operation. Suction system with suction control 600 includes suction device 602 and suction source 618.

Suction system with suction control 600 includes suction device 602. Suction device 602 is an example of suction device 100, suction device 202, suction device 402, and suction device 502; however, suction device 602 may include alternative configurations and methods of operation. Suction device 602 includes input port 604, suction port 606, suction lumen 608, instrument retainer 612, gasket 614, suction control 616, nozzle attachment 624 and nozzle 626. Suction device 602 is configured to couple to suction source 618. Suction source 618 may be a vacuum pump, aspirator, positive pressure operated suction source configured to take advantage of the Coanda effect, or some other means of generating suction. Suction source 618 generates low pressure region 622 near input port 604. Low pressure region 622 is at a pressure below the ambient air pressure, thus causing flow of matter 620 to be pulled into input port 604.

In some embodiments, suction device 602 may be configured to couple to a surgical instrument via instrument retainer 612.

Suction device 602 includes input port 604. Input port 604 is configured to supply flow of matter 620 to suction lumen 608. Input port 604 is disposed towards the distal end of suction device 602. Input port 604 is coupled to suction lumen 608. Input port 604 is configured to receive flow of matter 620. Flow of matter 620 may include liquids, gasses and solids. Flow of matter 620 may include bodily fluids, surgical byproducts and smoke. In some embodiments, input port 604 may include a positive pressure operated suction device configured to take advantage of the Coanda effect.

Suction device 602 includes suction port 606. Suction port 606 is configured to receive flow of matter 620 from suction lumen 608. Suction port 606 is coupled to suction lumen 608. Suction port 606 is disposed at the proximal end of suction device 602. Suction port 606 is configured to expel flow of matter 620. Suction port 606 is coupled to a suction source 618. Suction source 618 may include a vacuum pump, aspirator, positive pressure operation suction source configured to take advantage of the Coanda effect, or some other means of generating suction. In some embodiments, suction system 600 may include a separator disposed between suction port 606 and suction source 618 to remove waste material from flow of matter 620.

Suction device 602 includes suction lumen 608. Suction lumen 608 is configured to couple input port 604 to suction port 606. Suction lumen 608 is disposed within suction device 602. In some embodiments, suction lumen 608 may be fully enclosed. In some embodiments, suction lumen 608 may include an open portion configured to allow an obstruction to be removed from suction lumen 608.

Suction device 602 includes instrument retainer 612. Instrument retainer 612 is configured to couple suction device 602 to a surgical instrument. Instrument retainer 612 allows a surgical instrument to be attached and detached from suction device 602 without the use of tools. In some embodiments, instrument retainer 612 may be configured to accept a particular make and model of surgical instrument. In some embodiments, instrument retainer 612 may be configured to include a clip-type configuration to allow quick attachment and detachment of a surgical instrument without tools.

Suction device 602 includes gasket 614. Gasket 614 is configured to provide a seal between suction device 602 and a surgical instrument. Gasket 614 may prevent suction from suction source 618 from leaking between suction device 602 and a surgical instrument interface. In some embodiments, gasket 614 may be configured to include an obstruction clearing port configured to allow access to suction lumen 608 to remove an obstruction from suction lumen 608. This configuration allows a user to detach a surgical instrument and directly access suction lumen 608 to remove an obstruction. In some embodiments, gasket 614 may comprise a flexible membrane configured to be manipulated to clear an obstruction within suction lumen 608.

Suction device 602 includes suction control 616. Suction control 616 is configured to adjust a suction ratio of liquids, solids and gasses pulled into suction device 602. Suction control 616 may adjust a ratio of liquids, solids and gasses suctioned by suction device 602 by adjusting the location of nozzle 626. In some embodiments, suction control 616 may be configured to adjust intake ports included at input port 604. In some embodiments, suction control 616 may be configured to adjust intake ports included at nozzle 626. In some embodiments, suction control 616 may comprise a sliding member. In some embodiments, the sliding member may be configured to extend and retract nozzle 626 in order to selectively adjust a ratio of liquids, solids and gasses suctioned by suction device 602. In some embodiments, suction control 616 may include a means for securing a location of suction control 616. The means for securing suction control 616 may include detents, friction fit, notches or some other means for securing a location of suction control 616.

Suction device 602 includes nozzle attachment 624. Nozzle attachment 624 is configured to accept a variety of different nozzles 626 suited for an intended application. In some embodiments, nozzle attachment 624 may include threads, Luer locks, quick-disconnect, or some other fitting configured to allow attachment of nozzle 626.

Suction device 604 includes nozzle 626. Nozzle 626 is configured to couple to nozzle attachment 624. The shape and configuration of nozzle 626 may vary depending upon the intended application. In some embodiments, nozzle 626 may include intake ports disposed near the distal end of nozzle 626. In some embodiments, the intake ports disposed near the distal end of nozzle 626 may be variably opened or closed by a suction control. Nozzle 626 may be a commercially available nozzle.

Suction system 600 includes suction source 618. Suction source 618 is configured to supply suction to suction device 602. Suction source may be a vacuum pump, aspirator, positive pressure operated suction source configured to take advantage of the Coanda effect, or some other means of generating suction.

Figure 7:
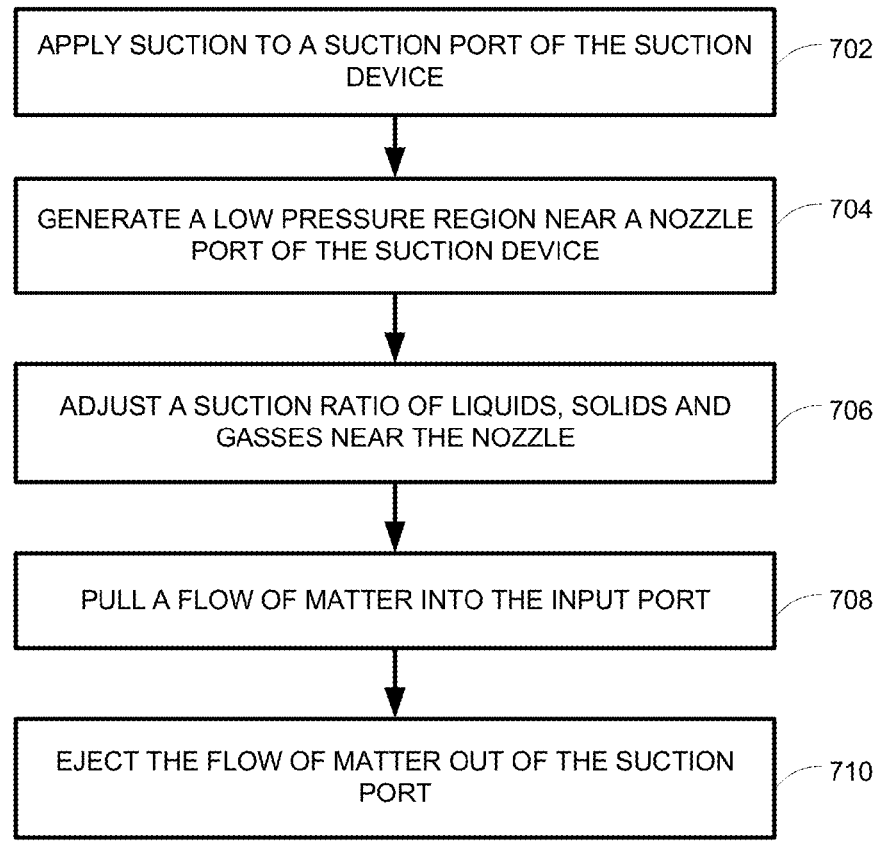
FIG. 7 is a block diagram illustrating a method of operating a suction system with suction control.

FIG. 7 is a block diagram illustrating a method of operating a suction system with suction control. The steps illustrated in FIG. 7 may be performed by one or more elements of suction system with suction control 600. Suction is applied to a suction port of a suction device (702). For example, suction port 606 is configured to couple to suction source 618. Suction source 618 is configured to apply suction to suction port 606 of suction device 602. Suction port 606 is coupled to suction lumen 608. Suction lumen 608 is coupled to input port 604. Suction lumen 608 is configured to transfer suction from suction source 618 to input port 604. A low pressure region is generated near a nozzle of the suction device (704). For example, nozzle 626 is coupled to input port 604. Input port 604 is configured to transfer suction from suction source 618 to nozzle 626 to generate low pressure region 622. Suction device 602 is configured to generate low pressure region 622 near input port 604 of suction device 602 from suction source 618. A suction ratio of liquids, solids and gasses adjusted near the nozzle (706). For example, suction device 602 includes suction control 616. Suction control 616 is configured to adjust a ratio of liquids, solids and gasses suctioned by suction device 602. In some embodiments, suction control 616 may be configured to adjust dimensions of intake ports disposed in input port 604 or nozzle 626 to adjust a ratio of liquids, solids and gasses suctioned by suction device 602. A flow of matter is pulled into the input port (708). For example, input port 604 is configured to receive flow of matter 620. Low pressure region 622 is at a pressure below an ambient air pressure. Low pressure region 622 is configured to pull flow of matter 620 into input port 604. The flow of matter is ejected out of the suction port (708). For example, suction device 602 includes suction lumen 608. Suction lumen 608 is coupled to suction port 606. Suction lumen 608 is configured to transfer flow of matter 620 to suction port 606. Suction port 606 is configured to eject flow of matter 620 from suction device 602.

Figure 8:
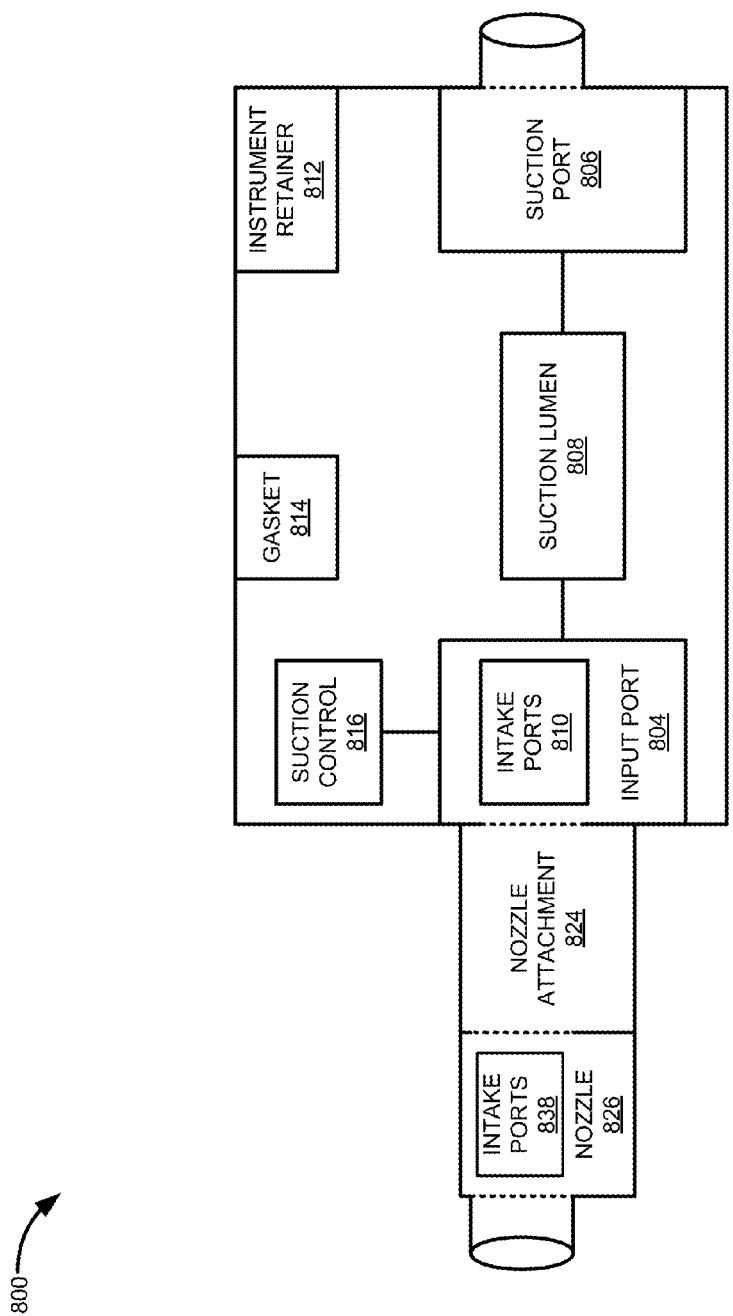
FIG. 8 is a block diagram illustrating a suction device.

FIG. 8 is a block diagram illustrating suction device 800. Suction device 800 is an example of suction device 100, suction device 202, suction device 402, suction device 502 and suction device 602; however, suction device 800 includes intake ports 810, 838. Suction device 800 includes input port 804, suction port 806, suction lumen 808, instrument retainer 812, gasket 814, suction control 816, nozzle attachment 824 and nozzle 826.

Suction device 800 is configured to couple to a suction source. The suction source may be a vacuum pump, aspirator, positive pressure operated suction source configured to take advantage of the Coanda effect, or some other means of generating suction. The suction source generates a low pressure region near nozzle 826. The low pressure region is at a pressure below the ambient air pressure, thus causing a flow of matter to be pulled into suction device 800. In some embodiments, suction device 800 may be configured to couple to a surgical instrument via instrument retainer 812.

Suction device 800 includes input port 804. Input port 804 is configured to receive a flow of matter. The flow of matter may include liquids, gasses and solids. The flow of matter may include bodily fluids, surgical byproducts and smoke. Input port 804 is disposed towards the distal end of suction device 800. Input port 804 is coupled to suction lumen 808. Input port 804 is configured to supply a flow of matter to suction lumen 808.

Input port 804 includes intake ports 810. Intake ports 810 are configured to suction a flow of matter into suction device 800. Intake ports 810 are disposed within input port 804. In some embodiments, intake ports 810 may be configured to take advantage of the Venturi effect. In some embodiments, intake ports 810 may be controlled by suction control 816. In some embodiments, suction control 816 may be configured to open and close intake ports 810. In some embodiments, suction control 816 may be configured to adjust dimension of intake ports 810 to adjust the amount of suction through intake ports 810.

Suction device 800 includes suction port 806. Suction port 806 is configured to receive flow of matter 820 from suction lumen 808. Suction port 806 is disposed at the proximal end of suction device 800. Suction port 806 is coupled to suction lumen 808. Suction port 806 is configured to expel a flow of matter. Suction port 806 may be coupled to a suction source. The suction source may include a vacuum pump, aspirator, positive pressure operation suction source configured to take advantage of the Coanda effect, or some other means of generating suction. In some embodiments, a suction system may include a separator disposed between suction port 806 and a suction source to remove waste material from a flow of matter.

Suction device 800 includes suction lumen 808. Suction lumen 808 is configured to couple input port 804 to suction port 806. Suction lumen 808 is disposed within suction device 800. In some embodiments, suction lumen 808 may be fully enclosed. In some embodiments, suction lumen 808 may include an open portion configured to allow an obstruction to be removed from suction lumen 808.

Suction device 800 includes instrument retainer 812. Instrument retainer 812 is configured to couple suction device 800 to a surgical instrument. Instrument retainer 812 allows a surgical instrument to be attached and detached from suction device 800 without the use of tools. In some embodiments, instrument retainer 812 may be configured to accept a particular make and model of surgical instrument. In some embodiments, instrument retainer 812 may be configured to include a clip-type configuration to allow quick attachment and detachment of a surgical instrument without tools.

Suction device 800 includes gasket 814. Gasket 814 is configured to provide a seal between suction device 800 and a surgical instrument. Gasket 814 may prevent suction from a suction source from leaking between suction device 800 and a surgical instrument interface. In some embodiments, gasket 814 may include an obstruction clearing port configured to allow access to suction lumen 808 to remove an obstruction. This configuration allows a user to detach a surgical instrument and directly access suction lumen 808 to remove an obstruction. In some embodiments, gasket 814 may comprise a flexible membrane configured to be manipulated to clear an obstruction within suction lumen 808.

Suction device 800 includes suction control 816. Suction control 816 is configured to adjust a suction ratio of liquids, solids and gasses pulled into suction device 800. Suction control 816 may adjust a ratio of liquids, solids and gasses suctioned by suction device 800 by adjusting the location of nozzle 826. In some embodiments, suction control 816 may be configured to adjust intake ports 810 included at input port 804. In some embodiments, suction control 816 may be configured to adjust intake ports 810, 838. In some embodiments, suction control 816 may comprise a sliding member. In some embodiments, the sliding member may be configured to extend and retract nozzle 826 in order to selectively adjust a ratio of liquids, solids and gasses suctioned by suction device 800. In some embodiments, suction control 816 may include a means for securing a location of suction control 816. The means for securing suction control 816 may include detents, friction fit, notches or some other means for securing a location of suction control 816.

Suction device 800 includes nozzle attachment 824. Nozzle attachment 824 is configured to accept a variety of different nozzles 826 suited for an intended application. In some embodiments, nozzle attachment 824 may include threads, Luer locks, quick-disconnect, or some other fitting configured to allow attachment of nozzle 826.

Suction device 800 includes nozzle 826. Nozzle 826 is configured to couple to nozzle attachment 824. The shape and configuration of nozzle 826 may vary depending upon the intended application. In some embodiments, nozzle 826 may include intake ports 838 disposed near the distal end of nozzle 826. In some embodiments, intake ports 838 may be variably opened or closed by suction control 816. Nozzle 826 may be a commercially available nozzle.

Nozzle 826 includes intake ports 838. Intake ports 838 are disposed within nozzle 826. Intake ports 838 are configured to suction a flow of matter into suction device 800. In some embodiments, intake ports 838 may be configured to take advantage of the Venturi effect. In some embodiments, intake ports 838 may be controlled by suction control 816. In some embodiments, suction control 816 may be configured to open and close intake ports 838. In some embodiments, suction control 816 may be configured to adjust dimension of intake ports 838 to adjust the amount of suction through intake ports 838.

Figure 9:
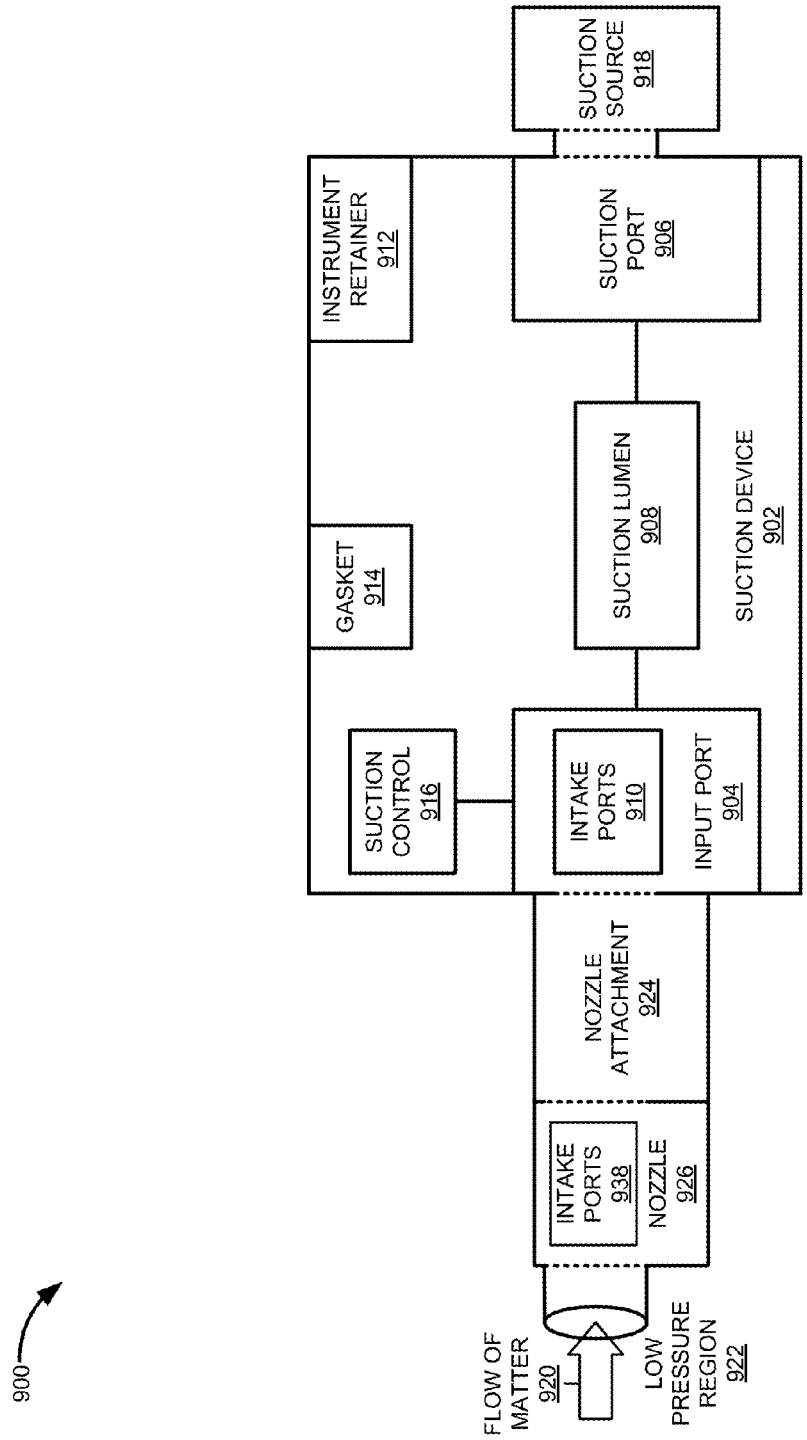
FIG. 9 is a block diagram illustrating the operation of a suction system.

FIG. 9 is a block diagram illustrating the operation of suction system 900. Suction system 900 is an example of suction system 200 and suction system with suction control 600; however suction system 900 may include alternative configurations and methods of operation. Suction system 900 includes suction device 902 and suction source 918.

Suction system 900 includes suction device 902. Suction device 902 is an example of suction device 100, suction device 202, suction device 402, and suction device 502;

however, suction device 902 includes intake ports 910, 938. Suction device 902 includes input port 904, suction port 906, suction lumen 908, instrument retainer 912, gasket 914, suction control 916, nozzle attachment 924 and nozzle 926. Suction device 902 is configured to couple to suction source 918. Suction source 918 may be a vacuum pump, aspirator, positive pressure operated suction source configured to take advantage of the Coanda effect, or some other means of generating suction. Suction source 918 is configured to generate low pressure region 922 near nozzle 926. Low pressure region 922 is at a pressure below the ambient air pressure, thus causing flow of matter 920 to be pulled into suction device 902. In some embodiments, suction device 902 may be configured to couple to a surgical instrument via instrument retainer 912.

Suction device 902 includes input port 904. Input port 904 is disposed towards the distal end of suction device 902. Input port 904 is coupled to suction lumen 908. Input port 904 is configured to receive flow of matter 920. Flow of matter 920 may include liquids, gasses and solids. Flow of matter 920 may include bodily fluids, surgical byproducts and smoke. Input port 904 is configured to supply flow of matter 920 to suction lumen 908. In some embodiments, input port 904 may include a positive pressure operated suction source configured to take advantage of the Coanda effect.

Input port 904 includes intake ports 910. Intake ports 910 are disposed within input port 904. Intake ports 910 are configured to suction flow of matter 920 into suction device 902. In some embodiments, intake ports 910 may be configured to take advantage of the Venturi effect. In some embodiments, intake ports 910 may be controlled by suction control 916. In some embodiments, suction control 916 may be configured to open and close intake ports 910. In some embodiments, suction control 916 may be configured to adjust dimension of intake ports 910 to adjust the amount of suction through intake ports 910.

Suction device 902 includes suction port 906. Suction port 906 is configured to expel flow of matter 920. Suction port 906 is disposed at the proximal end of suction device 902. Suction port 906 is coupled to suction lumen 908. Suction port 906 is configured to receive flow of matter 920 from suction lumen 908. Suction port 906 is coupled to a suction source 918. Suction source 918 may include a vacuum pump, aspirator, positive pressure operation suction source configured to take advantage of the Coanda effect, or some other means of generating suction. In some embodiments, suction system 900 may include a separator disposed between suction port 906 and suction source 918 to remove waste material from flow of matter 920.

Suction device 902 includes suction lumen 908. Suction lumen 908 is configured to couple input port 904 to suction port 906. Suction lumen 908 is disposed within suction device 902. In some embodiments, suction lumen 908 may be fully enclosed. In some embodiments, suction lumen 908 may include an open portion configured to allow an obstruction to be removed from suction lumen 908.

Suction device 902 includes instrument retainer 912. Instrument retainer 912 is configured to couple suction device 902 to a surgical instrument. Instrument retainer 912 allows a surgical instrument to be attached and detached from suction device 902 without the use of tools. In some embodiments, instrument retainer 912 may be configured to accept a particular make and model of surgical instrument. In some embodiments, instrument retainer 912 may be configured to include a clip-type configuration to allow quick attachment and detachment of a surgical instrument without tools.

Suction device 902 includes gasket 914. Gasket 914 is configured to provide a seal between suction device 902 and a surgical instrument. Gasket 914 may prevent suction from a suction source from leaking between suction device 902 and a surgical instrument interface. In some embodiments, gasket 914 may be configured to include an obstruction clearing port configured to allow access to suction lumen 908 to clear an obstruction within suction lumen 908. This configuration allows a user to detach a surgical instrument and directly access suction lumen 908 to remove an obstruction. In some embodiments, gasket 914 may be comprised of a flexible membrane configured to be manipulated to clear an obstruction within suction lumen 908.

Suction device 902 includes suction control 916. Suction control 916 is configured to adjust a ratio of liquids, solids and gasses pulled into suction device 902. Suction control 916 may adjust a ratio of liquids, solids and gasses suctioned by suction device 902 by adjusting the location of nozzle 926. In some embodiments, suction control 916 may be configured to adjust intake ports 910. In some embodiments, suction control 916 may be configured to adjust intake ports 938. In some embodiments, suction control 916 may comprise a sliding member. In some embodiments, the sliding member may be configured to extend and retract nozzle 926 in order to selectively adjust a ratio of liquids, solids and gasses suctioned by suction device 902. In some embodiments, suction control 916 may include a means for securing a location of suction control 916. The means for securing suction control 916 may include detents, friction fit, notches or some other means for securing a location of suction control 916.

Suction device 902 includes nozzle attachment 924. Nozzle attachment 924 is configured to accept a variety of different nozzles 926 suited for an intended application. In some embodiments, nozzle attachment 924 may include threads, Luer locks, quick-disconnect, or some other fitting configured to allow attachment of nozzle 926.

Suction device 902 includes nozzle 926. Nozzle 926 is configured to couple to nozzle attachment 924. The shape and configuration of nozzle 926 may vary depending upon the intended application. Nozzle 926 includes intake ports 938 disposed near the distal end of nozzle 926. In some embodiments, intake ports 938 may be variably opened or closed by suction control 916. Nozzle 926 may be a commercially available nozzle.

Nozzle 926 includes intake ports 938. Intake ports 938 are configured to suction flow of matter 920 into suction device 902. Intake ports 938 are disposed within nozzle 926. In some embodiments, intake ports 938 may be configured to take advantage of the Venturi effect. In some embodiments, intake ports 938 may be controlled by suction control 916. In some embodiments, suction control 916 may be configured to open and close intake ports 938. In some embodiments, suction control 916 may be configured to adjust dimension of intake ports 938 to adjust the amount of suction through intake ports 938.

Suction system 900 includes suction source 918. Suction source 918 is configured to supply suction to suction device 902. Suction source may be a vacuum pump, aspirator, positive pressure operated suction source configured to take advantage of the Coanda effect, or some other means of generating suction.

Figure 10:
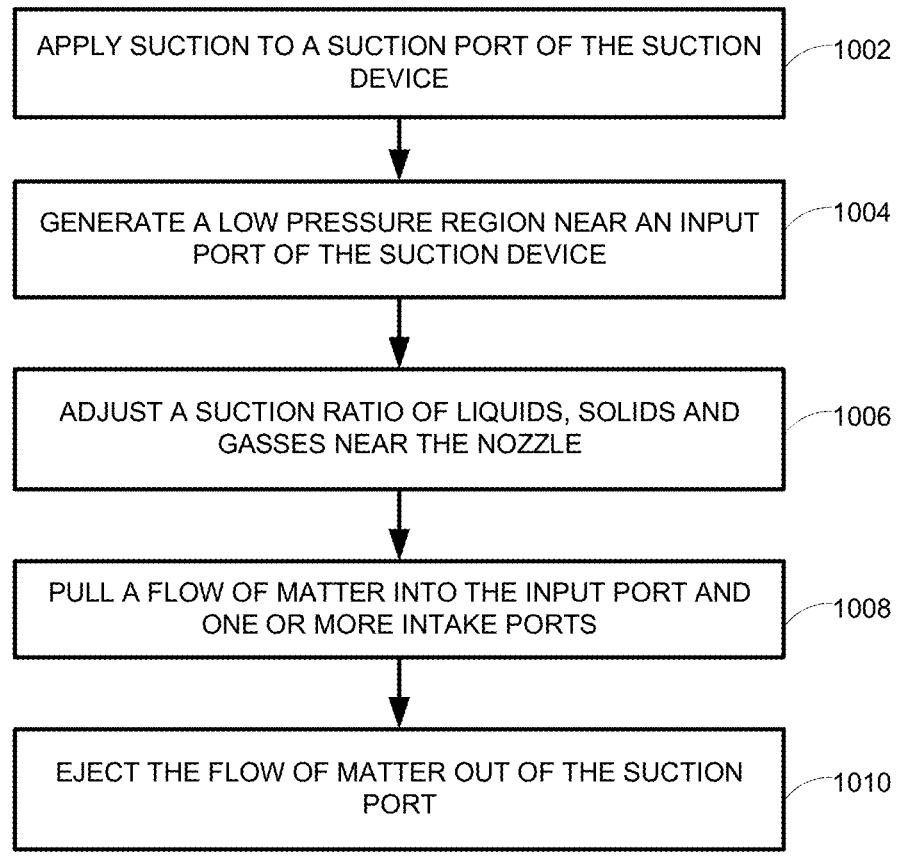
FIG. 10 is a diagram illustrating a method of operating a suction system.

FIG. 10 is a diagram illustrating a method of operating a suction system. The steps illustrated in FIG. 10 may be performed by one or more elements of suction system 900. Suction is applied to a suction port of a suction device (1002). For example, suction port 906 is configured to couple to suction source 918. Suction source 918 is configured to apply suction to suction port 906 of suction device 902. Suction port 906 is coupled to suction lumen 908. Suction lumen 908 is coupled to input port 904. Suction lumen 908 is configured to transfer suction from suction source 918 to input port 904. A low pressure region is generated near a nozzle of the suction device (1004). For example, nozzle 926 is coupled to input port 904. Input port 904 is configured to transfer suction from suction source 918 to nozzle 926 to generate low pressure region 922. Suction device 902 is configured to generate low pressure region 922 near input port 904 of suction device 902 from suction source 918. A suction ratio of liquids, solids and gasses adjusted near the nozzle (1006). For example, suction device 902 includes suction control 916. Suction control 916 is configured to adjust a ratio of liquids, solids and gasses suctioned by suction device 902. In some embodiments, suction control 916 may be configured to adjust dimensions of intake ports 910, 938 disposed in input port 904 or nozzle 926 to adjust a ratio of liquids, solids and gasses suctioned by suction device 902. A flow of matter is pulled into the input port and one or more intake ports (1008). For example, input port 904 is configured to receive flow of matter 920. Low pressure region 922 is at a pressure below an ambient air pressure. Low pressure region 922 is configured to pull flow of matter 920 into input port 904 and intake ports 910, 938. The flow of matter is ejected out of the suction port (1008). For example, suction device 902 includes suction lumen 908. Suction lumen 908 is coupled to suction port 906. Suction lumen 908 is configured to transfer flow of matter 920 to suction port 906. Suction port 906 is configured to eject flow of matter 920 from suction device 902.

Figure 11A:
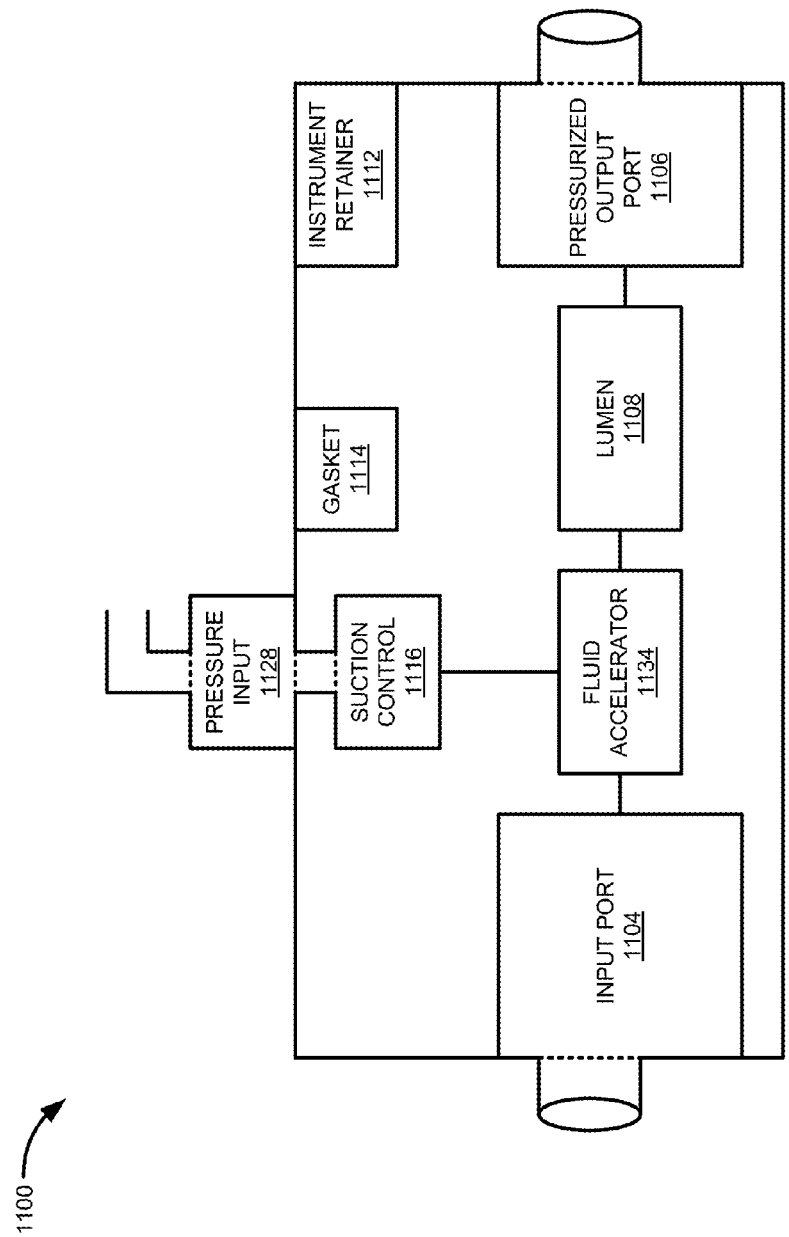
FIG. 11A is a block diagram illustrating a positive pressure operated suction device.

FIG. 11A is a block diagram illustrating positive pressure operated suction device 1100. Positive pressure operated suction device 1100 is an example of suction device 100, suction device 202, suction device 402, suction device 502, suction device 602, suction device 800, and suction device 902; however, positive pressure operated suction device 1100 includes pressure input 1128 and fluid accelerator 1134. Positive pressure operated suction device 1100 is configured to generate suction from a positive pressure supply rather than a suction or vacuum source. However, positive pressure operated suction device 1100 may be used in conjunction with a suction or vacuum source. Positive pressure operated suction device 1100 includes input port 1104, pressurized output port 1106, lumen 1108, instrument retainer 1112, gasket 1114, suction control 1116, pressure input 1128 and fluid accelerator 1134.

Positive pressure operated suction device 1100 is configured to couple to a positive pressure source. The positive pressure source may be an air compressor, compressed gas, a human breath or some other means of generating positive pressure. Positive pressure operated suction device 1100 is configured to take advantage of the Coanda effect to generate a low pressure region input port 1104. The low pressure region is at a pressure below the ambient air pressure, thus causing a flow of matter to be pulled into positive pressure operated suction device 1100.

Positive pressure operated suction device 1100 includes input port 1104. Input port 1104 is configured to receive a flow of matter. The flow of matter may include liquids, gasses and solids. The flow of matter may include bodily fluids, surgical byproducts and smoke. Input port 1104 is configured to supply a flow of matter to lumen 1108. Input port 1104 is disposed towards the distal end of positive pressure operated suction device 1100. Input port 1104 is coupled to lumen 1108.

Positive pressure operated suction device 1100 includes pressurized output port 1106. Pressurized output port 1106 is configured to receive a flow of matter 1120 from lumen 1108. Pressurized output port 1106 is disposed at the proximal end of positive pressure operated suction device 1100. Pressurized output port 1106 is coupled to lumen 1108. Pressurized output port 1106 is configured to expel a flow of matter. Pressurized output port 1106 may be coupled to a suction source. The suction source may include a vacuum pump, aspirator, positive pressure operation suction source configured to take advantage of the Coanda effect, or some other means of generating suction. In some embodiments, a suction system may include a separator disposed between pressurized output port 1106 and a suction source to remove waste material from a flow of matter.

Positive pressure operated suction device 1100 includes lumen 1108. Lumen 1108 is configured to couple input port 1104 to pressurized output port 1106. Lumen 1108 is disposed within positive pressure operated suction device 1100. In some embodiments, lumen 1108 may be fully enclosed. In some embodiments, lumen 1108 may include an open portion configured to allow an obstruction to be removed from lumen 1108.

Positive pressure operated suction device 1100 includes instrument retainer 1112. Instrument retainer 1112 is configured to couple positive pressure operated suction device 1100 to a surgical instrument. Instrument retainer 1112 allows a surgical instrument to be attached and detached from positive pressure operated suction device 1100 without the use of tools. In some embodiments, instrument retainer 1112 may be configured to accept a particular make and model of surgical instrument. In some embodiments, instrument retainer 1112 may be configured to include a clip-type configuration to allow quick attachment and detachment of a surgical instrument without tools.

Positive pressure operated suction device 1100 includes gasket 1114. Gasket 1114 is configured to provide a seal between positive pressures operated suction device 1100 and a surgical instrument. Gasket 1114 may prevent suction from a suction source from leaking between positive pressure operated suction device 1100 and a surgical instrument interface. In some embodiments, gasket 1114 may include an obstruction clearing port configured to allow access to lumen 1108 to remove an obstruction. This configuration allows a user to detach a surgical instrument and directly access lumen 1108 to remove an obstruction. In some embodiments, gasket 1114 may comprise a flexible membrane configured to be manipulated to clear an obstruction within lumen 1108.

Positive pressure operated suction device 1100 includes suction control 1116. Suction control 1116 is configured to adjust suction generated near input port 1104. Suction control 1116 may adjust a ratio of liquids, solids and gasses suctioned by positive pressure operated suction device 1100. In some embodiments, suction control 1116 may include an adjustable pressure gap. The adjustable pressure gap may comprise an annular opening within suction control 1116 configured to supply pressure from a positive pressure source. The adjustable pressure gap may be configured to adjust a mass flow rate of pressure received from a positive pressure source. Increasing the mass flow rate of pressure will increase the mass flow rate of a flow of matter received at input port 1104 until an upper threshold mass flow rate of the flow of matter is limited by the internal dimensions of positive pressure operated suction device 1100. Increasing the mass flow rate of pressure beyond the upper threshold may not increase the mass flow rate of the flow of matter received at input port 1104. However, increasing the mass flow rate of pressure beyond the upper threshold may increase suction near input port 1104. In other words, increasing the mass flow rate of pressure beyond the upper threshold may not increase the amount of matter suctioned by positive pressure operated suction device 1100, but it may increase how hard the matter is suctioned. In some embodiments, suction control 1116 may include a rotatable member configured to adjust the dimension of the annular opening. In some embodiments, suction control 1116 may include a sliding member configured to adjust the dimension of annular opening.

The annular opening of the adjustable pressure gap may be configured to supply pressure from a positive pressure source to fluid accelerator 1134 at an angle in relation to an interior wall of fluid accelerator 1134. In some embodiments, suction control 1116 may be configured to adjust the angle. Adjusting the angle at which pressure is supplied by suction control 1116 to fluid accelerator 1134 may adjust suction generated near input port 1104. In some embodiments, the angle may be fixed. In some embodiments, the angle will be an acute angle. In some embodiments, the angle may be in a range between 30-60°. In an embodiment, the angle may be 55°.

Positive pressure operated suction device 1100 includes pressure input 1128. Pressure input 1128 is configured to receive a positive pressure source. For example, the positive pressure source may be a flow of compressed air, nitrogen, carbon dioxide or some other gaseous pressure source. The positive pressure source is pressured above the ambient air pressure surrounding positive pressure operated suction device 1100. Pressure input 1128 is coupled to suction control 1116. Pressure input 1128 is configured to supply a positive pressure gas to suction control 1116. In some embodiments, pressure input 1128 may further comprises an external coupler or connector for coupling with, for example, tubing.

Positive pressure operated suction device 1100 includes fluid accelerator 1134. Fluid accelerator 1134 is configured to generate a low pressure region near input port 1104 from a positive pressure source. In an embodiment, fluid accelerator 1134 is configured to take advantage of the Coanda effect to create suction near input port 1104. The suction is primarily created by fluid accelerator 1134 from a flow of air or a gas (typically pressurized above ambient) that is provided to fluid accelerator 1134—not an external suction pump (although the device may be used in conjunction with a suction pump). Fluid accelerator 1134 is configured to receive a positive pressure source from suction control 1116. A ratio of liquids, solids, and gasses suctioned by positive pressure operated suction device 1100 may be varied by suction control 1116. Suction control 1116 may be configured to vary a ratio of liquids, solids, and gasses suctioned by controlling the amount of positive pressure received by fluid accelerator 1134. In some embodiments, suction control 1116 is configured to direct a positive pressure gas at an angle in relation to an interior wall of fluid accelerator 1134. In some embodiments, fluid accelerator 1134 may comprise one or more hollow segments positioned essentially in line with one another. The one or more hollow segments may be configured to communicate such that the one or more hollow segments are continuous. The one or more hollow segments may be fluidly continuous such that, for example, a flow of suction may travel from one hollow segment to another. The one or more hollow segments may be configured to communicate such that, for example, a flow of a suctioned gas, liquid, solid, or any combination thereof may travel from one hollow segment to another.

Figure 11B:
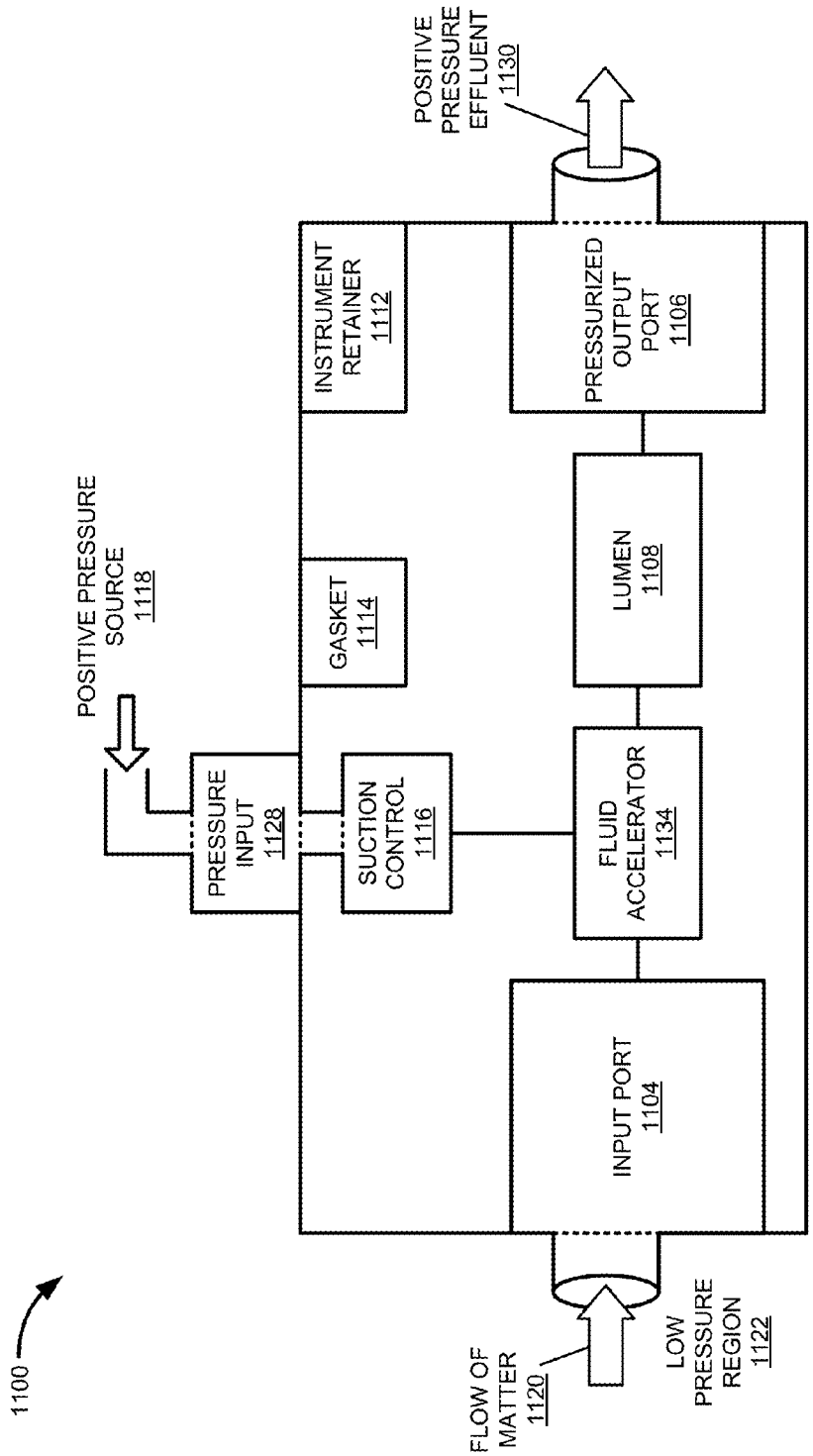
FIG. 11B is a block diagram illustrating the operation of a positive pressure operated suction device.

FIG. 11B is a block diagram illustrating the operation of a positive pressure operated suction device 1100. In operation, positive pressure source 1118 is received by pressure input 1128. Pressure input 1128 is coupled to suction control 1116. Pressure input 1128 supplies positive pressure source 1118 to suction control 1116. Suction control 1116 includes an annular opening configured to supply positive pressure source 1118 to fluid accelerator 1134. Suction control 1116 may be configured to adjust the amount of positive pressure source 1118 supplied to fluid accelerator 1134. The amount of positive pressure source 1118 supplied to fluid accelerator 1134 may adjust a ratio of liquids, solids, and gasses suctioned as flow of matter 1120. Fluid accelerator 1134 is configured to generate low pressure region 1122 from positive pressure source 1118 received from suction control 1116. Low pressure region 1122 is at a pressure below an ambient air pressure, thus causing flow of matter 1120 to be pulled into positive pressure operated suction device 1100. Flow of matter 1120 passes through input port 1104, fluid accelerator 1134 and lumen 1108 before being expelled by pressurized output port 1106 as positive pressure effluent 1130.

Figure 11C:
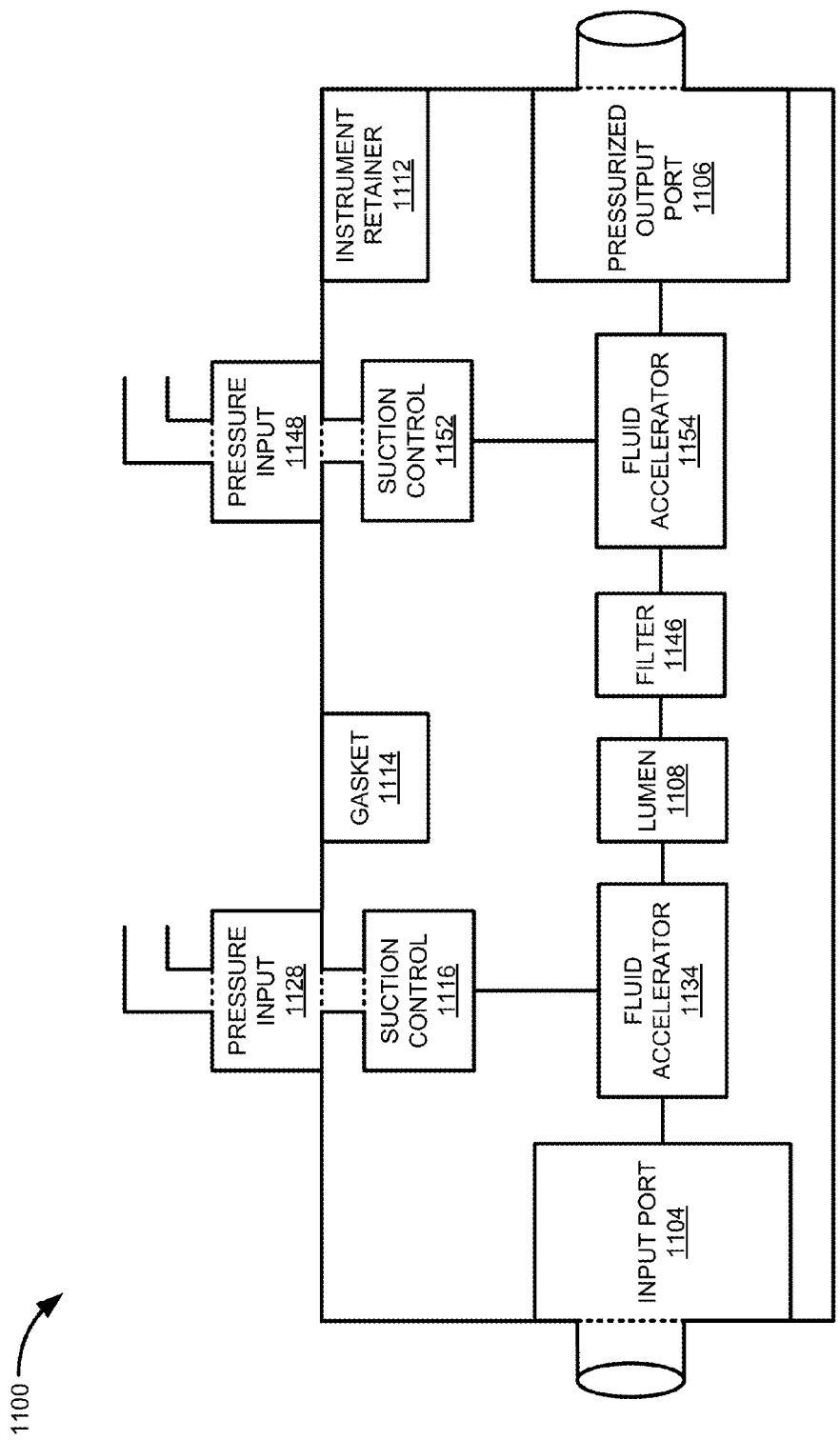
FIG. 11C is a block diagram illustrating the operation of a positive pressure operated suction device.

FIG. 11C is a block diagram illustrating the operation of a positive pressure operated suction device 1100. In some embodiments, the suction device 1100 comprises one or more fluid accelerators. In the embodiment shown, the suction device comprises two fluid accelerators 1134 and 1154. A first fluid accelerator 1134 is positioned to generate or increase a suction force at the input port 1104. In some embodiments, a suction device comprises a filter 1146 that may be configured to filter, for example, a solid, liquid, or gas that is suctioned through the suction device. In the embodiment shown, a filter 1146 is positioned proximal to a fluid accelerator 1154 so that a suction force draws a solid, liquid, or gas through the filter 1146.

Figure 12:
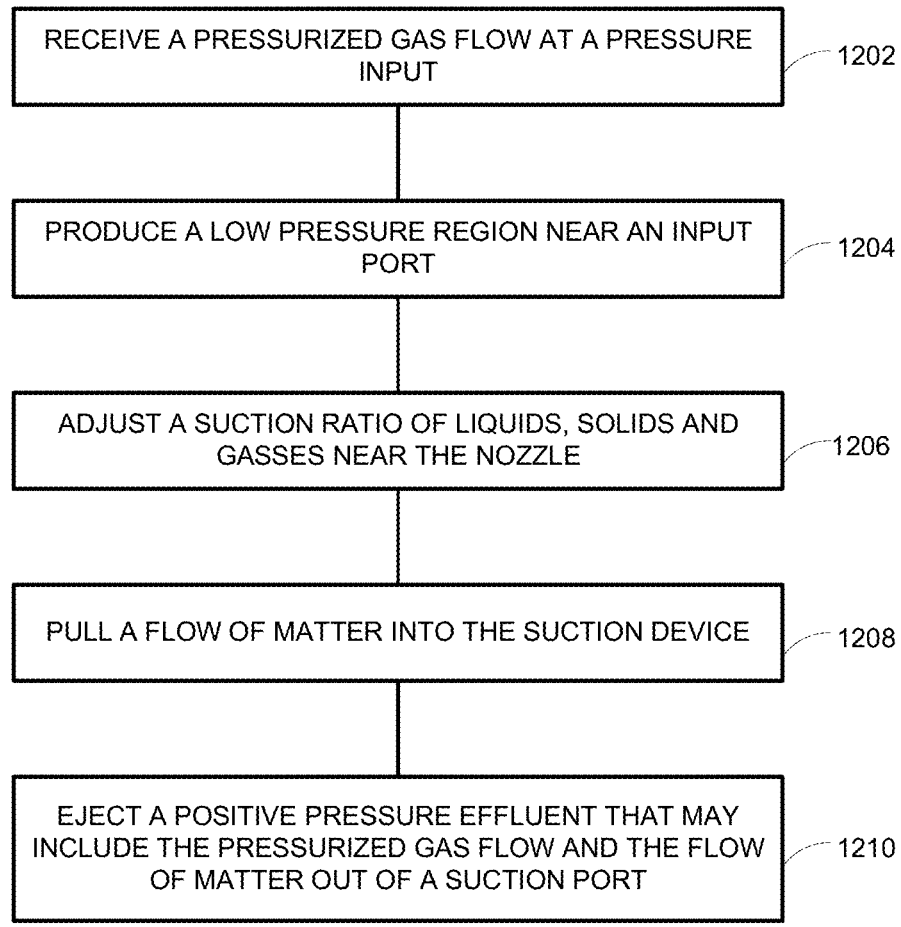
FIG. 12 is a diagram illustrating a method of operating a positive pressure operated suction device.

FIG. 12 is a diagram illustrating a method of operating a positive pressure operated suction device. The steps illustrated in FIG. 12 may be performed by one or more elements of positive pressure operated suction device 1100. A pressurized gas flow is received at an input port (1202). For example, input port 1104 is configured to receive positive pressure source 1118. Positive pressure source 1118 is an example of a pressurized gas flow. Input port 1104 is configured to supply positive pressure source 1118 to suction control 1116. Suction control 1116 is coupled to fluid accelerator 1134. Suction control 1116 is configured to supply positive pressure source 1118 to fluid accelerator 1134. A low pressure region is produced near an input port (1204). For example, fluid accelerator 1134 is configured to produce low pressure region 1122 near input port 1104 from positive pressure source 1118. Fluid accelerator 1134 may be configured to take advantage of the Coanda effect to generate low pressure region 1122. A pressure difference between the low pressure region and an ambient air pressure is adjusted (1206). For example, suction control 1116 includes an adjustable annular gap configured to adjust the supply of positive pressure source 1118 to fluid accelerator 1134. Adjustment of the supply of positive pressure source 1118 to fluid accelerator 1134 adjusts a pressure difference between low pressure region 1122 and the ambient air pressure. A flow of matter is pulled into the suction device (1208). For example, low pressure region 1122 is less than the ambient air pressure. This pressure difference causes flow of matter 1120 to enter input port 1104. Input port 1104 is configured to receive flow of matter 1120. A positive pressure effluent that may include the pressurized gas flow and the flow of matter is ejected out of an exhaust port (1210). For example, positive pressure operated suction device 1100 is configured to pass flow of matter 1120 from input port 1104 through fluid accelerator 1134 and lumen 1108 and eject positive pressure effluent 1130 (which can include positive pressure source 1118 and flow of matter 1120) out pressurized output port 1106.

Figure 13A:
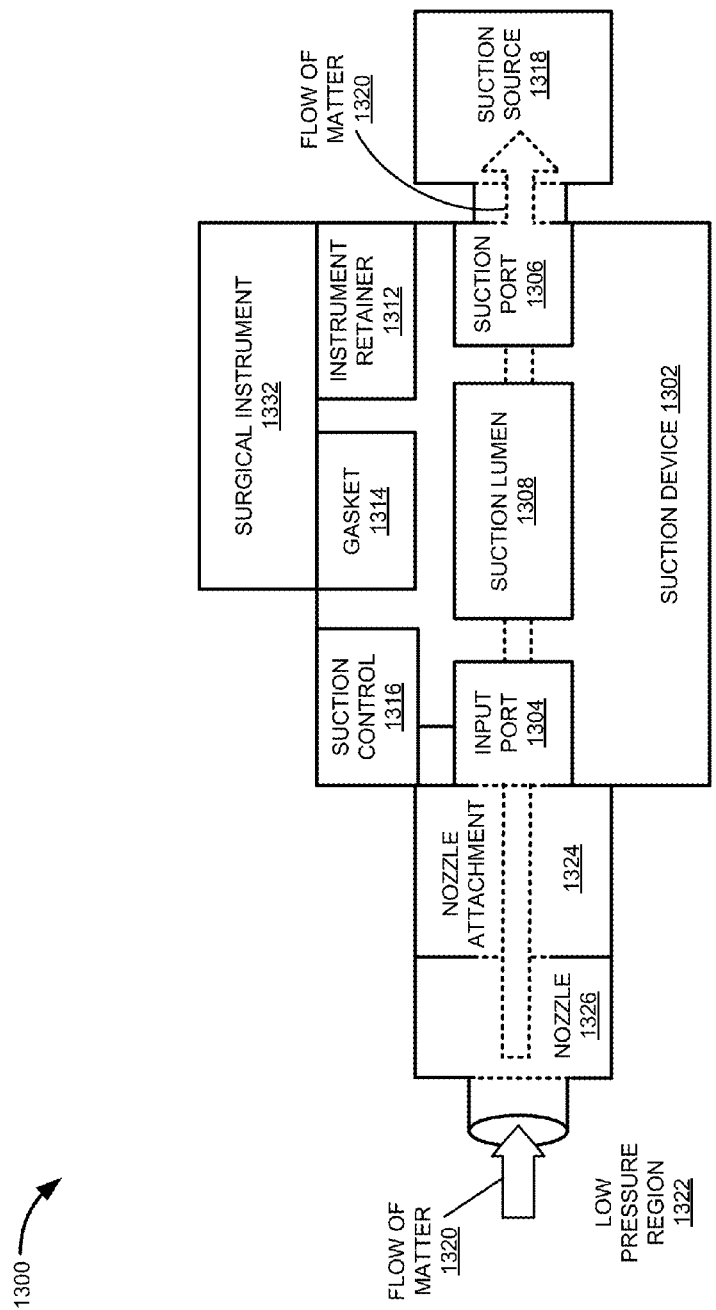
FIG. 13A is a block diagram illustrating the operation of a suction system.

FIG. 13A is a block diagram illustrating the operation of suction system 1300. Suction system 1300 includes suction device 1302, suction source 1318, and surgical instrument 1332.

Suction system 1300 includes suction device 1302. Suction device 1302 is an example of suction device 100, suction device 202, suction device 402, suction device 502, suction device 602, suction device 800, suction device 902 and positive pressure operated suction device 1100; however, suction device 1302 may include alternative configurations and methods of operation. Suction device 1302 includes input port 1304, suction port 1306, suction lumen 1308, instrument retainer 1312, gasket 1314, suction control 1316, suction source 1318, nozzle attachment 1324 and nozzle 1326. Suction device 1302 is configured to couple to suction source 1318. Suction source 1318 may be a vacuum pump, aspirator, positive pressure operated suction source configured to take advantage of the Coanda effect, or some other means of generating suction. Suction source 1318 generates low pressure region 1322 near input port 1304. Low pressure region 1322 is at a pressure below the ambient air pressure, thus causing flow of matter 1320 to be pulled into suction device 1302. Suction device 1302 includes instrument retainer 1312. Instrument retainer 1312 is configured to couple suction device 1302 to surgical instrument 1332.

Suction device 1302 includes input port 1304. Input port 1304 is configured to receive flow of matter 1320. Flow of matter 1320 may include liquids, gasses and solids. Flow of matter 1320 may include bodily fluids, surgical byproducts and smoke. Input port 1304 is disposed towards the distal end of suction device 1302. Input port 1304 is coupled to suction lumen 1308. Input port 1304 is configured to supply flow of matter 1320 to suction lumen 1308.

Suction device 1302 includes suction port 1306. Suction port 1306 is configured to receive flow of matter 1320 from suction lumen 1308. Suction port 1306 is disposed at the proximal end of suction device 1302. Suction port 1306 is coupled to suction lumen 1308. Suction port 1306 is configured to expel flow of matter 1320. Suction port 1306 is coupled to suction source 1318. Suction source 1318 may include a vacuum pump, aspirator, positive pressure operation suction source configured to take advantage of the Coanda effect, or some other means of generating suction. In some embodiments, suction system 1300 may include a separator disposed between suction port 1306 and suction source 1318 to remove waste material from flow of matter 1320.

Suction device 1302 includes suction lumen 1308. Suction lumen 1308 is configured to couple input port 1304 to suction port 1306. Suction lumen 1308 is disposed within suction device 1302. In some embodiments, suction lumen 1308 may be fully enclosed. In some embodiments, suction lumen 1308 may include an open portion configured to allow an obstruction to be removed from suction lumen 1308.

Suction device 1302 includes instrument retainer 1312. Instrument retainer 1312 is configured to couple suction device 1302 to a surgical instrument. Instrument retainer 1312 allows a surgical instrument to be attached and detached from suction device 1302 without the use of tools. In some embodiments, instrument retainer 1312 may be configured to accept a particular make and model of surgical instrument. In some embodiments, instrument retainer 1312 may be configured to include a clip-type configuration to allow quick attachment and detachment of a surgical instrument without tools.

Suction device 1302 includes gasket 1314. Gasket 1314 is configured to provide a seal between suction device 1302 and a surgical instrument. Gasket 1314 may prevent suction from suction source 1318 from leaking between suction device 1302 and a surgical instrument interface. In some embodiments, gasket 1314 may include an obstruction clearing port configured to allow access to suction lumen 1308 to remove an obstruction. This configuration allows a user to detach a surgical instrument and directly access suction lumen 1308 to remove an obstruction. In some embodiments, gasket 1314 may comprise a flexible membrane configured to be manipulated to clear an obstruction within suction lumen 1308.

Suction device 1302 includes suction control 1316. Suction control 1316 is configured to adjust a suction ratio of liquids, solids and gasses pulled into suction device 1302. Suction control 1316 may adjust a ratio of liquids, solids and gasses suctioned by suction device 1302 by adjusting the location of nozzle 1326. In some embodiments, suction control 1316 may be configured to adjust intake ports included at input port 1304. In some embodiments, suction control 1316 may be configured to adjust intake ports included at nozzle 1326. In some embodiments, suction control 1316 may comprise a sliding member. In some embodiments, the sliding member may be configured to extend and retract nozzle 1326 in order to selectively adjust a ratio of liquids, solids and gasses suctioned by suction device 1302. In some embodiments, suction control 1316 may include a means for securing a location of suction control 1316. The means for securing suction control 1316 may include detents, friction fit, notches or some other means for securing a location of suction control 1316.

Suction device 1302 includes nozzle attachment 1324. Suction device 1302 includes nozzle attachment 1324. Nozzle attachment 1324 is configured to accept a variety of different nozzles 1326 suited for an intended application. In some embodiments, nozzle attachment 1324 may include threads, Luer locks, quick-disconnect, or some other fitting configured to allow attachment of nozzle 1326.

Suction device 1304 includes nozzle 1326. Nozzle 1326 is configured to couple to nozzle attachment 1324. The shape and configuration of nozzle 1326 may vary depending upon the intended application. Nozzle 926 may be a commercially available nozzle.

Suction system 1300 includes suction source 1318. Suction source 1318 is an example of suction source 218, suction source 618 and suction source 918; however, suction source 1318 may include alternative configurations and methods of operation. Suction source 1318 is configured to supply suction to suction device 1302. Suction source 1318 may be a vacuum pump, aspirator, positive pressure operated suction source configured to take advantage of the Coanda effect, or some other means of generating suction.

Suction system 1300 includes surgical instrument 1332. Surgical instrument 1332 may be any surgical instrument that may benefit from suction device 1302. Some surgical instruments that may benefit from suction device 1302 include electrosurgical instruments using heat conduction, diathermy, radio-frequency, and laser methods of operation.

In operation, suction source 1318 supplies suction to suction port 1306. Suction port 1306 is coupled to suction source 1318. Suction port 1306 receives suction from suction source 1318. Suction lumen 1308 is configured to couple suction port 1306 to input port 1304. Suction lumen 1308 transfers suction received by suction port 1306 to input port 1304. Input port 1304 is coupled to nozzle attachment 1324. Nozzle attachment 1324 is coupled to nozzle 1326. Suction is transferred from input port 1304 through nozzle attachment 1324 and nozzle 1326 to generate low pressure region 1322. Suction control 1316 is configured to vary a ratio of liquids, solids, and gasses suctioned by suction device 1302. In some embodiments, suction control 1316 may be configured to adjust the position of nozzle 1326 in relation to surgical instrument 1332 to vary the suction ration of liquids, solids and gasses. Low pressure region 1322 is at a pressure below the ambient air pressure. This pressure difference causes flow of matter 1320 to pass through suction device 1302. Flow of matter 1320 passes through suction device 1302 and is expelled by suction port 1306.

Figure 13B:
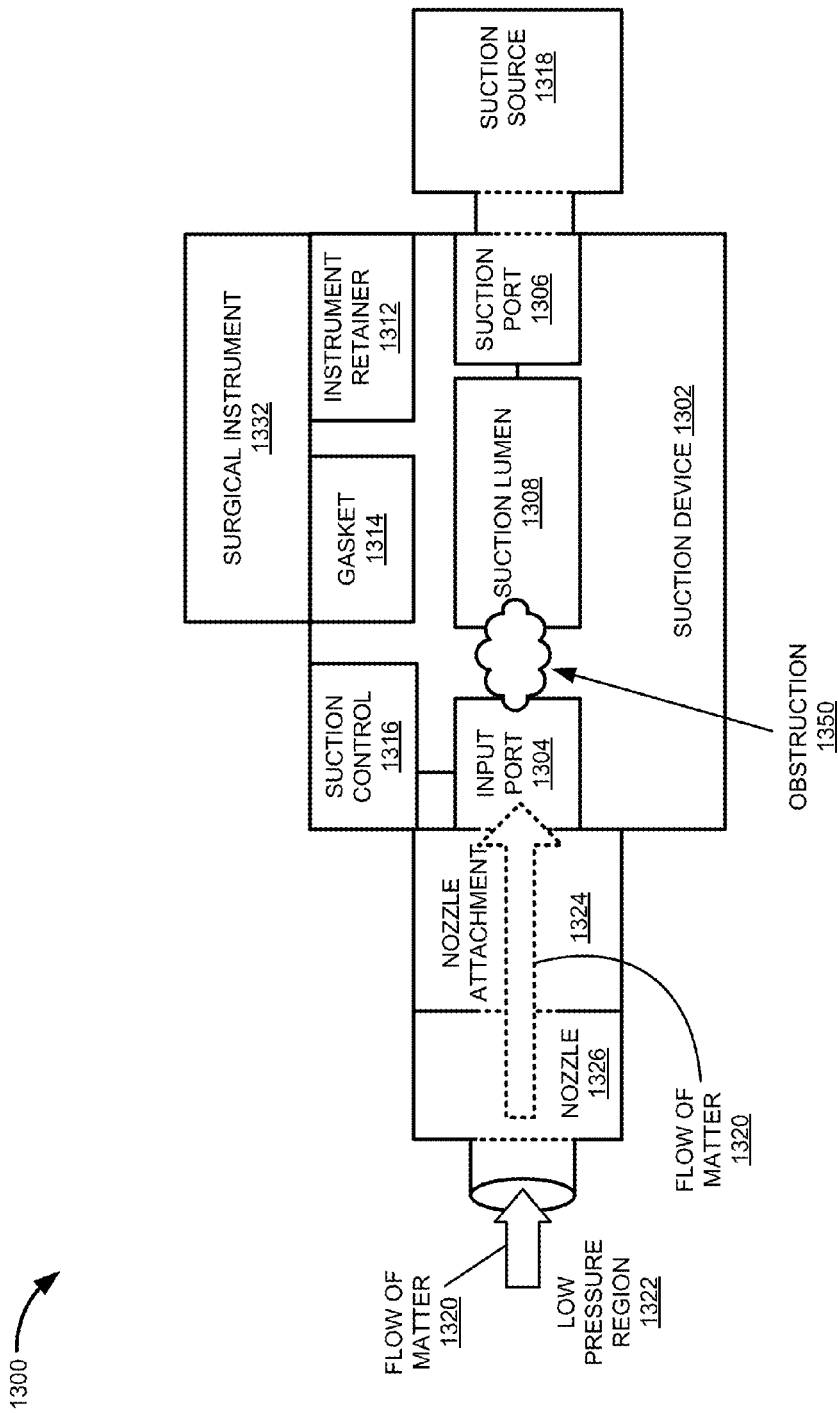
FIG. 13B is a block diagram illustrating the operation of a suction system in the event of an obstruction.

FIG. 13B is a block diagram illustrating the operation of suction system 1300 in the event of an obstruction. FIG. 13B illustrates suction system 1300 with obstruction 1350. Obstruction 1350 prevents all, or a portion of, flow of matter 1320 from passing through suction device 1302. Although obstruction 1350 is illustrated in FIG. 13B between input port 1304 and suction lumen 1308, it should be understood that obstruction 1350 could be anywhere within suction device 1302.

Figure 13C:
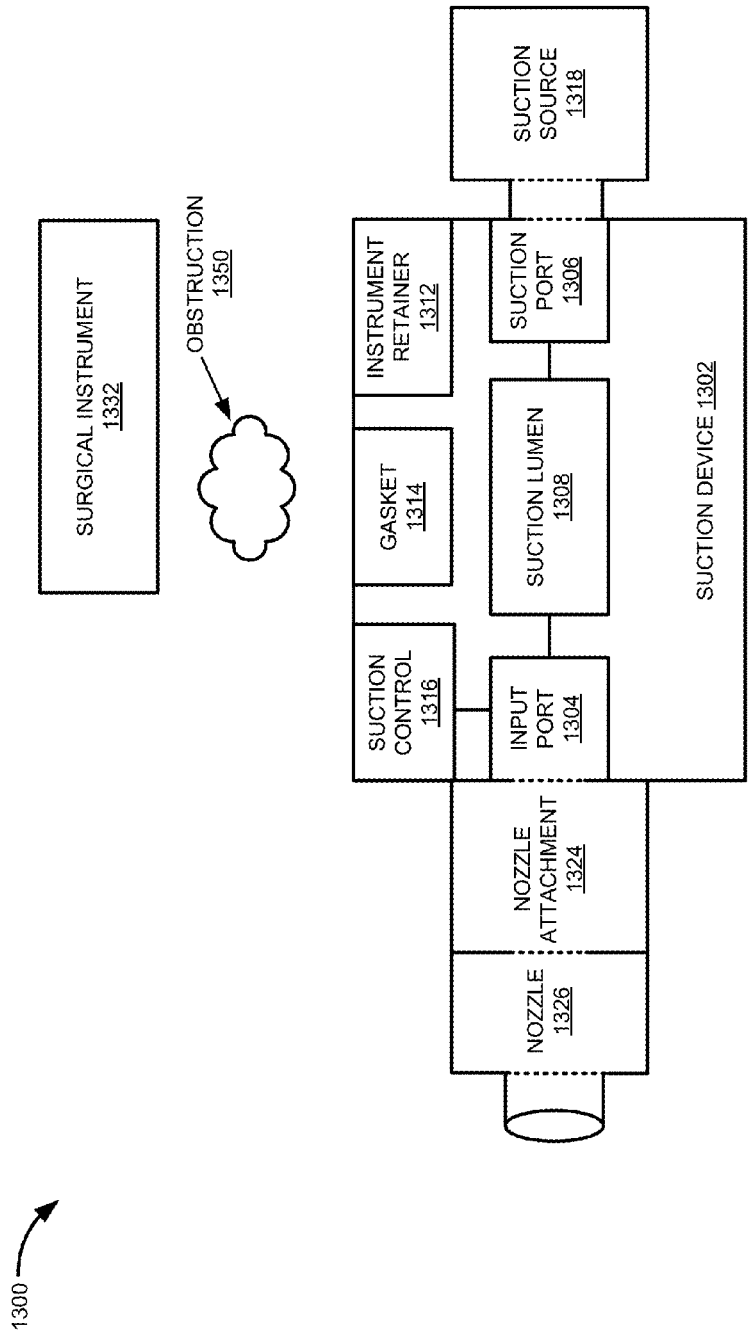
FIG. 13C is a block diagram illustrating the operation of clearing a suction system.

FIG. 13C is a block diagram illustrating the operation of clearing suction system 1300. Instrument retainer 1312 is configured to allow surgical instrument 1332 to be attached and detached from suction device 1302 without the use of tools or other devices. In the event that obstruction 1350 has prevented flow of matter 1320 from passing through suction device 1302 as illustrated in FIG. 13B, surgical instrument 1332 may be detached from suction device 1302 to remove obstruction 1350.

FIG. 13C illustrates surgical instrument 1332 detached from suction device 1302. Obstruction 1350 has been removed from suction device 1302. In some embodiments, gasket 1314 may include an obstruction clearing port configured to allow access to input port 1304, suction lumen 1308, or suction port 1306, or a combination thereof. Obstruction 1350 may be removed through the obstruction clearing port. In some embodiments, gasket 1314 may comprise a flexible membrane. The flexible membrane may be configured to allow a user to manipulate the membrane to free obstruction 1350 and allow it to pass out suction port 1306. In some embodiments, suction lumen 1308 may include an opening disposed between suction device 1302 and surgical instrument 1332. In this configuration, surgical instrument 1332 forms a portion of a wall of suction lumen 1308. Gasket 1314 may be configured to provide a seal between suction lumen 1308 and surgical instrument 1332.

Figure 14:
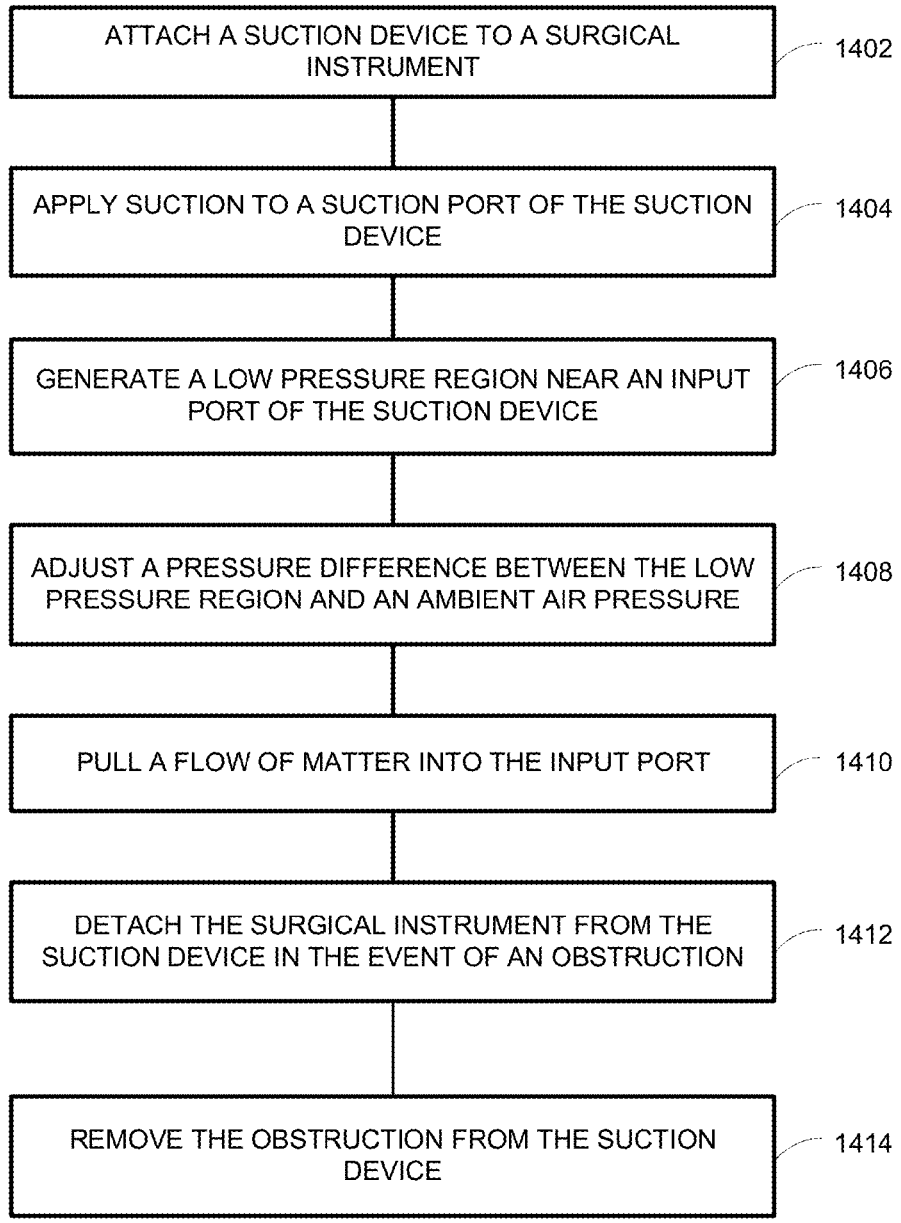
FIG. 14 is a diagram illustrating a method of operating a suction system.

FIG. 14 is a diagram illustrating a method of operating a suction system. The steps illustrated in FIG. 14 may be performed by one or more elements of suction system 1300. A surgical instrument is attached to suction device (1400). For example, suction device 1302 includes instrument retainer 1312. Instrument retainer 1312 is configured to attach surgical instrument 1332 to suction device 1302. Instrument retainer 1312 is configured such that surgical instrument 1332 may be quickly attached or detached from suction device 1302. Suction is applied to a suction port of a suction device (1404). For example, suction port 1306 is configured to couple to suction source 1318. Suction source 1318 is configured to apply suction to suction port 1306 of suction device 1302. A low pressure region is generated near an input port of the suction device (1406). For example, suction device 1302 is configured to generate low pressure region 1322 near nozzle 1326 of suction device 1302 from suction source 1318. In some embodiments, input port 1304 may be used without nozzle 1326. A pressure difference between the low pressure region and an ambient air pressure is adjusted (1408). For example, suction device 1302 includes suction control 1316. Suction control 1316 is configured to adjust a pressure difference between low pressure region 1322 and an ambient air pressure. Suction control 1316 does not adjust suction source 1318 to adjust the pressure difference between low pressure region 1322 and an ambient air pressure. A flow of matter is pulled into the input port (1410). For example, input port 1304 is configured to receive flow of matter 1320. Low pressure region 1322 is at a pressure below an ambient air pressure. Low pressure region 1322 is configured to pull flow of matter 1320 into input port 1304. The surgical instrument is detached from the suction device in the event of an obstruction (1412). For example, instrument retainer 1312 is configured to allow surgical instrument 1332 to be easily detached from suction device 1302. The obstruction is removed from the suction device (1414). Suction device 1302 may be configured to include access ports to remove obstruction 1350 from suction device 1302. The method may be repeated beginning at step 1400 once obstruction 1350 is removed from suction device 1302.

Figure 15:
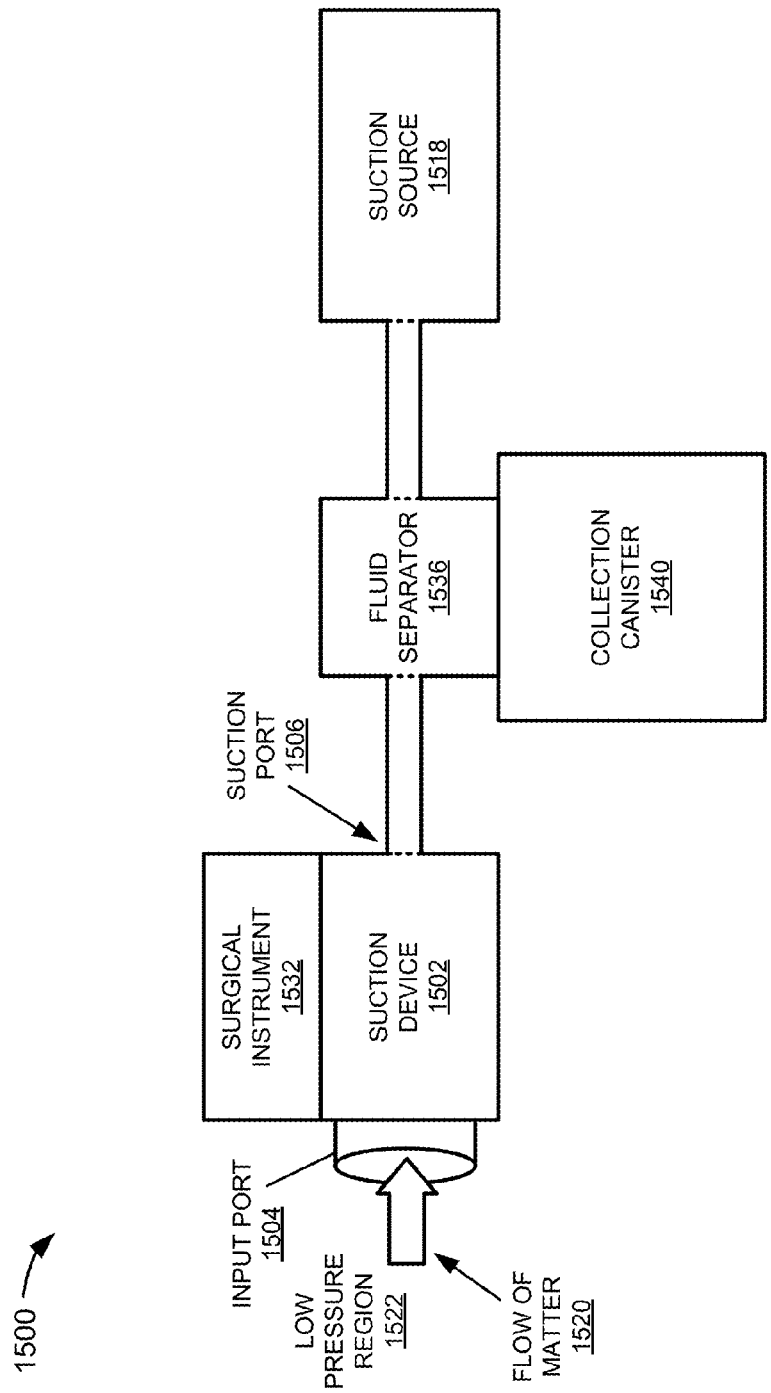
FIG. 15 is a block diagram illustrating a suction system.

FIG. 15 is a block diagram illustrating suction system 1500. Suction system 1500 includes suction device 1502, suction source 1518, surgical instrument 1532, fluid separator 1536 and collection canister 1540. Suction device 1502, suction source 1518 and surgical instrument 1532 are examples of elements previously described. Fluid separator 1536 may be configured to separate liquids, solids, and gasses that may be included in flow of matter 1520. Fluid separator 1536 is coupled to collection canister 1540. Collection canister 1540 is configured to receive constituents separated from flow of matter 1520 by fluid separator 1536. Collection canister 1540 may be used to measure, safely transport, or dispose of constituents separated from flow of matter 1520 by fluid separator 1536.

In operation, suction source 1518 supplies suction to fluid separator 1536. Fluid separator 1536 is configured to use suction supplied by suction source 1518 to separate constituents included in flow of matter 1520. Fluid separator 1536 is configured to transfer suction from suction source 1518 to suction device 1502. Suction device 1502 is configured to generate low pressure region 1522 near input port 1504. Low pressure region 1522 is at a pressure below the ambient air pressure. This pressure difference causes flow of matter 1520 to be pulled into suction device 1502.

Surgical instrument 1532 may be an electrosurgical instrument. The use of electrosurgical instruments may generate smoke or other noxious gasses. Suction device 1502 is configured to suction at least the smoke or other noxious gasses generated by surgical instrument 1532. Suction device 1502 may suction liquids and solids in addition to smoke and other noxious gasses. Suction device 1502 may include a suction control to vary a ratio of liquids, solids, and gasses suctioned by suction device 1502.

Flow of matter 1520 is expelled from suction device 1502 out suction port 1506. Flow of matter 1520 is received by fluid separator 1536. Fluid separator 1536 may be configured to use cyclonic flow and gravity to separate liquids and solids from gasses that may comprise flow of matter 1520. Fluid separator 1536 is configured to expel at least liquids and solids included in the flow of matter 1520 to collection canister 1540. Gasses from flow of matter 1520 may be suctioned from fluid separator 1536 by suction source 1518. While not illustrated in FIG. 15, filters may be included at various points throughout suction system 1500. For example, suction device 1502 may be configured to include a filter or a filter may be placed between fluid separator 1536 and suction source 1518.

Figure 16:
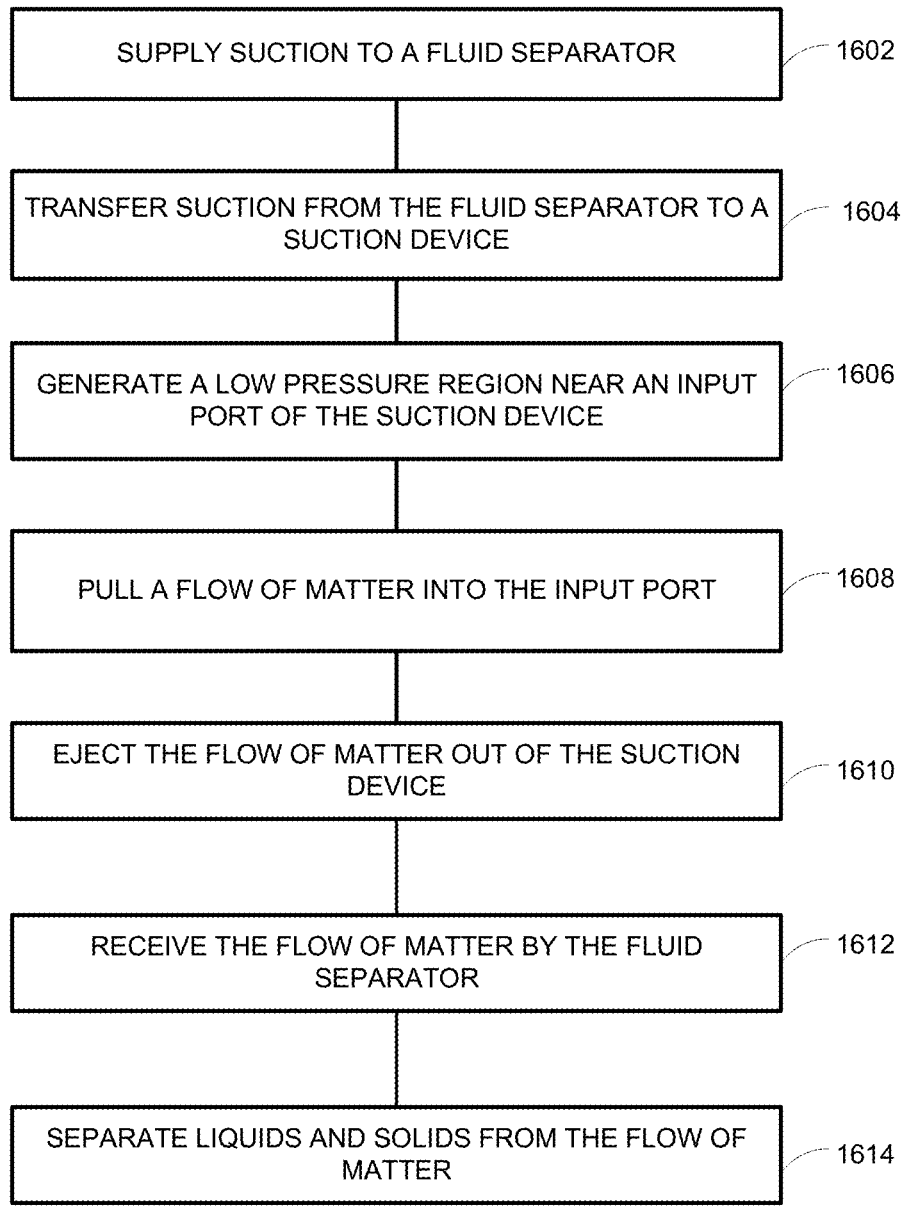
FIG. 16 is a diagram illustrating a method of operating a suction system.

FIG. 16 is a diagram illustrating a method of operating a suction system. The steps illustrated in FIG. 16 may be performed by one or more elements of suction system 1500. Suction is supplied to a fluid separator (1602). For example, suction system 1500 includes suction source 1518. Suction source 1518 is coupled to fluid separator 1536. Suction source 1518 is configured to supply suction to fluid separator 1536. Suction is transferred from the fluid separator to a suction device (1604). For example, fluid separator 1536 is coupled to suction device 1502. Fluid separator 1536 is configured to transfer suction from suction source 1518 to suction device 1502. A low pressure region is generated near an input port of the suction device (1606). For example, suction device 1502 includes input port 1504. Low pressure region 1522 is generated near input port 1504 by suction source 1518. Pull a flow of matter into the input port (1608). For example, low pressure region 1522 is at a pressure below an ambient air pressure. The pressure difference between low pressure region 1522 and the ambient air pressure causes flow of matter 1520 to be pulled into input port 1504. Eject the flow of matter out of the suction device (1610). Suction device 1502 includes suction port 1506. Suction port 1506 is configured to eject flow of matter 1520. The flow of matter is received by the fluid separator (1612). For example, fluid separator 1536 is coupled to suction device 1502. Fluid separator 1536 is configured to receive flow of matter 1520. Liquids and solids are separated from the flow of matter (1614). Fluid separator 1536 is configured to separate liquids, solids and gasses from flow of matter 1520 using suction supplied by suction source 1518.

Figure 17A:
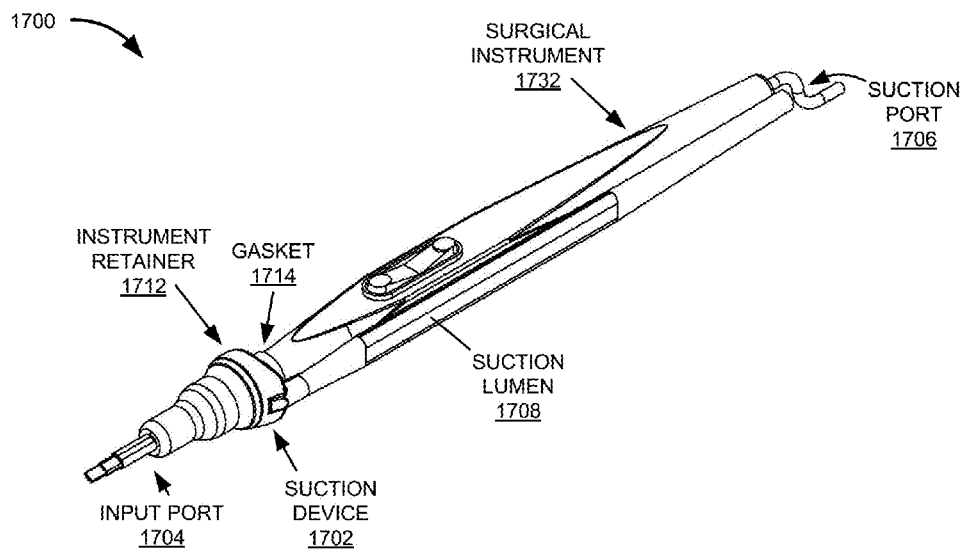
FIG. 17A is a diagram illustrating a suction device with surgical instrument.

FIG. 17A is a diagram illustrating suction device with surgical instrument 1700. Suction device with surgical instrument 1700 includes suction device 1702 and surgical instrument 1732.

Suction device with surgical instrument 1700 includes suction device 1702. Suction device 1702 is an example of suction device 100, suction device 202, suction device 402, suction device 502, suction device 602, suction device 800, suction device 902 and positive pressure operated suction device 1100; however, suction device 1702 may include alternative configurations and methods of operation. Suction device 1702 includes input port 1704, suction port 1706, suction lumen 1708, instrument retainer 1712 and gasket 1714. Suction device 1702 is configured to couple to a suction source. The suction source may be a vacuum pump, aspirator, positive pressure operated suction source configured to take advantage of the Coanda effect, or some other means of generating suction. The suction source is configured to generate a low pressure region near input port 1704. The low pressure region is at a pressure below the ambient air pressure, thus causing a flow of matter to be pulled into suction device 1702. Suction device 1702 includes instrument retainer 1712. Instrument retainer 1712 is configured to couple suction device 1702 to surgical instrument 1732.

Suction device 1702 includes input port 1704. Input port 1704 is disposed towards the distal end of suction device 1702. Input port 1704 comprises a cylindrical body. Input port 1704 is configured to couple to a mating cylindrical cavity included in suction device 1702. Input port 1704 is configured to be in fluidic communication with suction lumen 1708. In some embodiments, input port 1704 may include a plurality of Venturi ports disposed within the cylindrical body. Input port 1704 is configured to receive a flow of matter. The flow of matter may include liquids, gasses and solids. The flow of matter may include bodily fluids, surgical byproducts and smoke. Input port 1704 is configured to supply the flow of matter to suction lumen 1708.

Suction device 1702 includes suction port 1706. Suction port 1706 is configured to expel the flow of matter received from suction lumen 1708. Suction port 1706 is disposed at the proximal end of suction device 1702. Suction port 1706 is coupled to suction lumen 1708. Suction port 1706 is configured to receive a flow of matter from suction lumen 1708. Suction port 1706 is configured to couple to a suction source or fluid separator that is coupled to a suction source. The suction source may include a vacuum pump, aspirator, positive pressure operation suction source configured to take advantage of the Coanda effect, or some other means of generating suction. In some embodiments, the suction system may include a separator disposed between suction port 1706 and the suction source to remove waste material from a flow of matter.

Suction device 1702 includes suction lumen 1708. Suction lumen 1708 is disposed within suction device 1702. Suction lumen 1708 is comprised of a lumen having a fully enclosed solid wall. Suction lumen 1708 is configured to be approximately the same length as surgical instrument 1732 so that suction port 1706 is conveniently located in relation to surgical instrument 1732. This configuration prevents an output tube or hose from interfering with the operation of surgical instrument 1732. Suction lumen 1708 is configured to couple input port 1704 to suction port 1706.

Suction device 1702 includes instrument retainer 1712. Instrument retainer 1712 is configured to couple suction device 1702 to surgical instrument 1732. Instrument retainer 1712 allows surgical instrument 1732 to be attached and detached from suction device 1702 without the use of tools. In some embodiments, instrument retainer 1712 may be configured to accept a particular make and model of surgical instrument. In this example, instrument retainer 1712 is configured to couple suction device 1702 to surgical instrument 1732 using friction.

Suction device 1702 includes gasket 1714. Gasket 1714 is configured to provide a seal between suction device 1702 and surgical instrument 1732. Gasket 1214 may prevent suction from leaking between suction device 1702 and surgical instrument 1732.

Suction device with surgical instrument 1700 includes surgical instrument 1732. Surgical instrument 1732 may be any surgical instrument that may benefit from suction device 1702. Some surgical instruments that may benefit from suction device 1702 include electrosurgical instruments using heat conduction, diathermy, radio-frequency, and laser methods of operation.

Figure 17B:
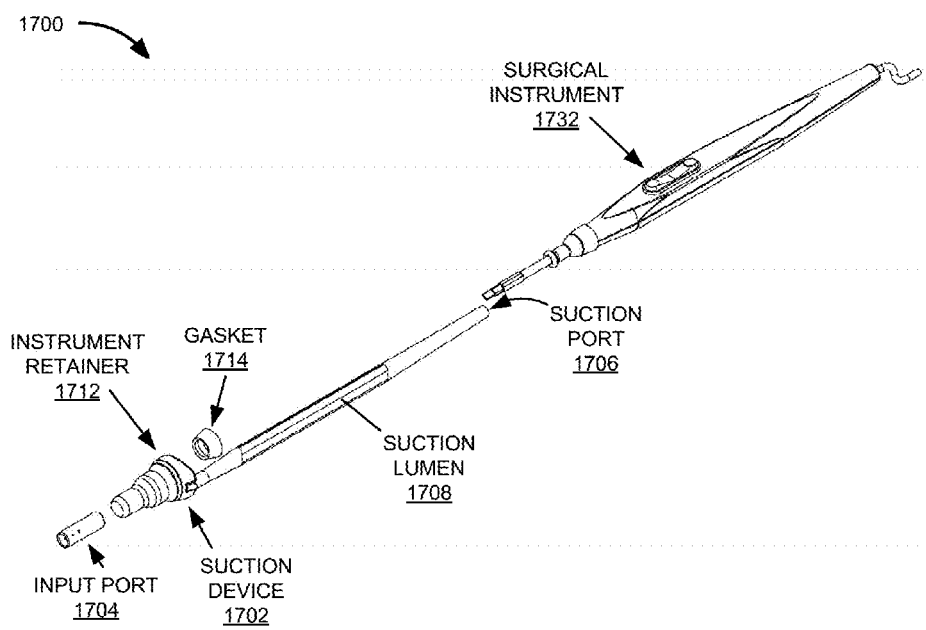
FIG. 17B is an exploded-view diagram illustrating a suction device with surgical instrument.

FIG. 17B is an exploded-view diagram illustrating suction device with surgical instrument 1700. The elements illustrated in FIG. 17B are the same as FIG. 17A. For the sake of brevity, the elements will not be described further.

Figure 17C:
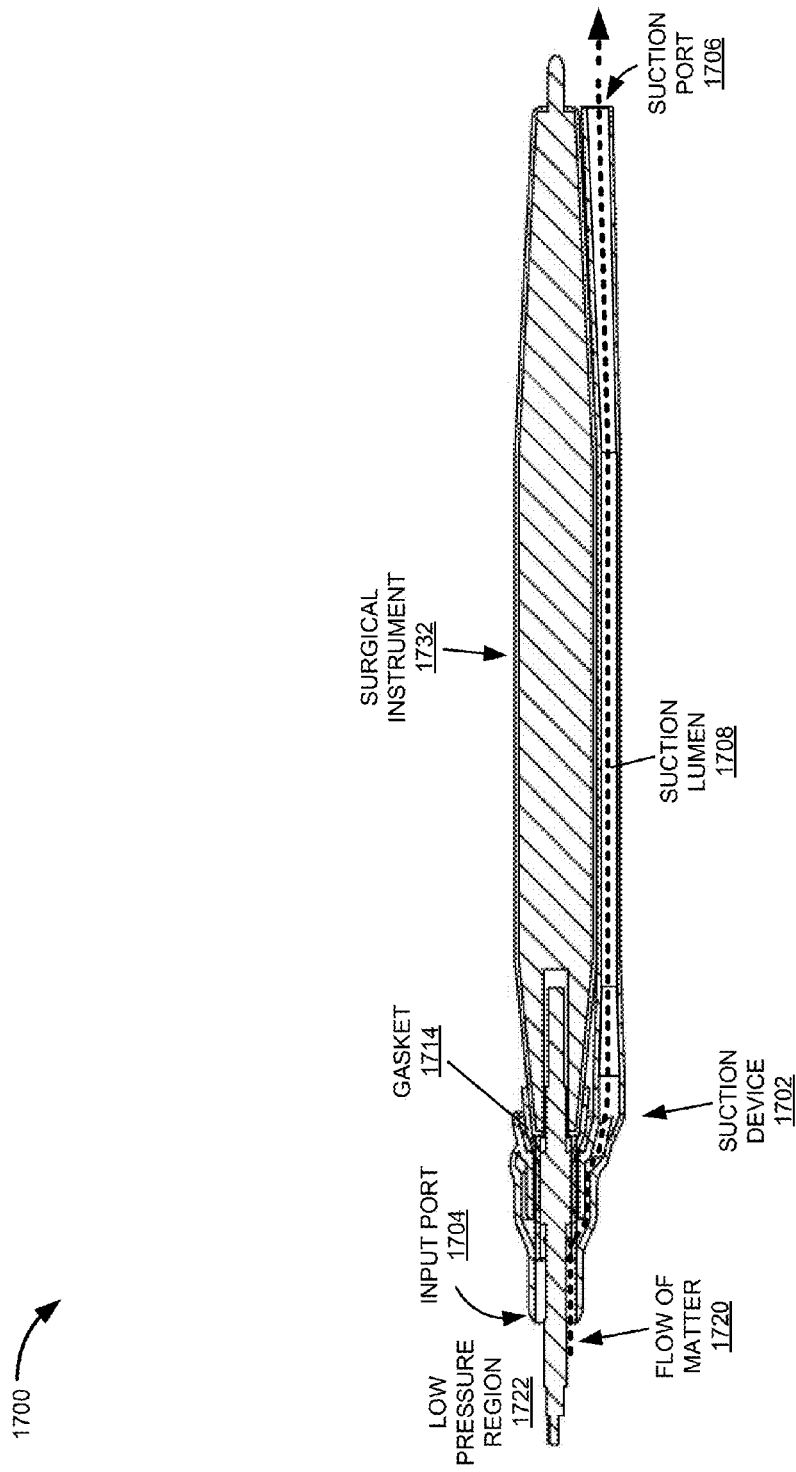
FIG. 17C is a cross-section diagram illustrating the operation of a suction device with surgical instrument.

FIG. 17C is a cross-section diagram illustrating the operation of suction device with surgical instrument 1700. In operation, suction from a suction source is applied to suction port 1706. Suction lumen 1708 is configured to couple suction port 1706 to input port 1704. Suction lumen 1708 transfers suction received by suction port 1706 to input port 1704. Suction device 1702 is configured to generate low pressure region 1722 near input port 1704 from suction supplied by a suction source. Gasket 1714 is configured to prevent suction from leaking between a suction device 1702 and surgical instrument 1732 interface. Low pressure region 1722 is at a pressure below the ambient air pressure. This pressure difference causes flow of matter 1720 to be pulled into suction device 1702. Suction device 1702 passes flow of matter 1720 through input port 1704, suction lumen 1708 and out suction port 1706. In some embodiments, a filter may be coupled to suction port 1706 before coupling to a suction source. In some embodiments, a fluid separator may be coupled to suction port 1706 before coupling to a suction source.

Figure 18A:
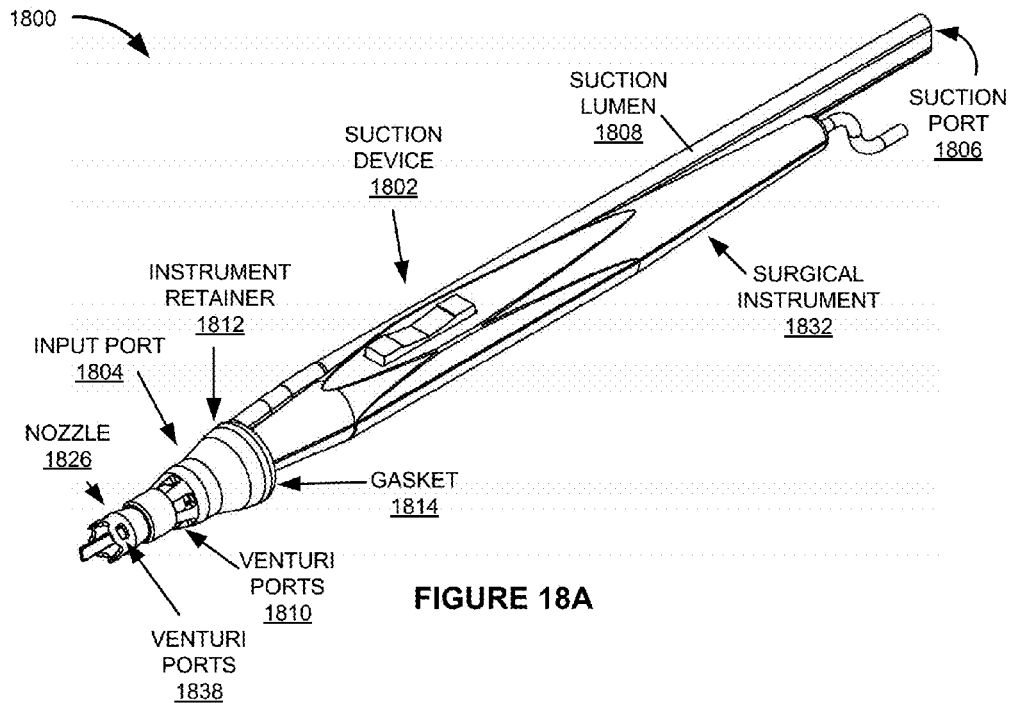
FIG. 18A is a diagram illustrating a suction device with surgical instrument.

FIG. 18A is a diagram illustrating suction device with surgical instrument 1800. Suction device with surgical instrument 1800 includes suction device 1802 and surgical instrument 1832. Suction device 1802 is configured to couple to a suction source. The suction source may be a vacuum pump, aspirator, positive pressure operated suction source configured to take advantage of the Coanda effect, or some other means of generating suction. The suction source is configured to generate a low pressure region near input port 1804. The low pressure region is at a pressure below the ambient air pressure, thus causing a flow of matter to be pulled into suction device 1802. Suction device 1802 includes instrument retainer 1812. Instrument retainer 1812 is configured to couple suction device 1802 to surgical instrument 1832.

Suction device with surgical instrument 1800 includes suction device 1802. Suction device 1802 is an example of suction device 100, suction device 202, suction device 402, suction device 502, suction device 602, suction device 800, suction device 902 and positive pressure operated suction device 1100; however, suction device 1802 may include alternative configurations and methods of operation. Suction device 1802 includes input port 1804, suction port 1806, suction lumen 1808, Venturi ports 1810, instrument retainer 1812, gasket 1814, nozzle attachment 1824 and nozzle 1826.

Suction device 1802 includes input port 1804. Input port 1804 is configured to receive a flow of matter. The flow of matter may include liquids, gasses and solids. The flow of matter may include bodily fluids, surgical byproducts and smoke. Input port 1804 is disposed towards the distal end of suction device 1802. Input port 1804 couples to suction port 1806 via suction lumen 1808. Input port 1804 is in fluidic communication with suction lumen 1808. Input port 1804 is configured to supply the flow of matter to suction lumen 1808.

Input port 1804 includes a plurality of Venturi ports 1810. Venturi ports 1810 are configured to suction at least gasses, aerosols and smoke. Venturi ports 1810 may improve the suction of a flow of matter suctioned by suction device 1802. Venturi ports 1810 may be configured to adjust a ratio of liquids, solids, and gasses suctioned by suction device 1802. In operation, Venturi ports 1810 increase the velocity of a flow while maintaining a constant volume of flow. Venturi ports 1810 may be configured for specific applications.

Suction device 1802 includes suction port 1806. Suction port 1806 is configured to expel the flow of matter received from suction lumen 1808. Suction port 1806 is disposed at the proximal end of suction device 1802. Suction port 1806 is coupled to suction lumen 1808. Suction port 1806 is configured to receive a flow of matter from suction lumen 1808. Suction port 1806 is configured to couple to a suction source or fluid separator that is coupled to a suction source. The suction source may include a vacuum pump, aspirator, positive pressure operation suction source configured to take advantage of the Coanda effect, or some other means of generating suction. In some embodiments, the suction system may include a separator disposed between suction port 1806 and the suction source to remove waste material from a flow of matter.

Suction device 1802 includes suction lumen 1808. Suction lumen 1808 is disposed within suction device 1802. Suction lumen 1808 is comprised of a lumen having a fully enclosed solid wall. Suction lumen 1808 is configured to be approximately the same length as surgical instrument 1832 so that suction port 1806 is conveniently located in relation to surgical instrument 1832. This configuration prevents an output tube or hose from interfering with the operation of surgical instrument 1832. Suction lumen 1808 is configured to couple input port 1804 to suction port 1806.

Suction device 1802 includes instrument retainer 1812. Instrument retainer 1812 is configured to couple suction device 1802 to surgical instrument 1832. Instrument retainer 1812 allows surgical instrument 1832 to be attached and detached from suction device 1802 without the use of tools. In some embodiments, instrument retainer 1812 may be configured to accept a particular make and model of surgical instrument. In this example, instrument retainer 1812 is configured to couple suction device 1802 to surgical instrument 1832 using friction.

Suction device 1802 includes gasket 1814. Gasket 1814 is configured to provide a seal between suction device 1802 and surgical instrument 1832. Gasket 1814 may prevent suction from leaking between suction device 1802 and surgical instrument 1832.

Suction device 1802 includes nozzle attachment 1824. Nozzle attachment 1824 is configured to couple to a variety of different nozzles 1826 suited for an intended application. In this embodiment, nozzle attachment 1824 is configured to secure nozzle 1826 using friction. In some embodiments, nozzle attachment 1824 may include threads, Luer locks, quick-disconnect, or some other fitting configured to allow attachment of nozzle 1826.

Suction device 1802 includes nozzle 1826. Nozzle 1826 is configured to couple to nozzle attachment 1824. In this embodiment, nozzle 1826 is secured to nozzle attachment 1824 using friction. The shape and configuration of nozzle 1826 may vary depending upon the intended application. In this example, the distal end of nozzle 1826 includes a plurality of indentations. The size, shape and dimensions of the plurality of indentations may be varied to suit specific applications. Nozzle 1826 may be a commercially available nozzle.

Nozzle 1826 includes Venturi ports 1838. Venturi ports 1838 are configured to suction at least gasses, aerosols and smoke. Venturi ports 1838 may also suction liquids. Venturi ports 1838 may improve suction of a flow of matter suctioned by suction device 1802. Venturi ports 1838 may be configured to adjust a ratio of liquids, solids, and gasses suctioned by suction device 1802. In operation, Venturi ports 1838 increase the velocity of a flow while maintaining a constant volume of flow. Venturi ports 1838 may be configured for specific applications.

Suction device with surgical instrument 1800 includes surgical instrument 1832. Surgical instrument 1832 may be any surgical instrument that may benefit from suction device 1802. Some surgical instruments that may benefit from suction device 1802 include electrosurgical instruments using heat conduction, diathermy, radio-frequency, and laser methods of operation.

Figure 18B:
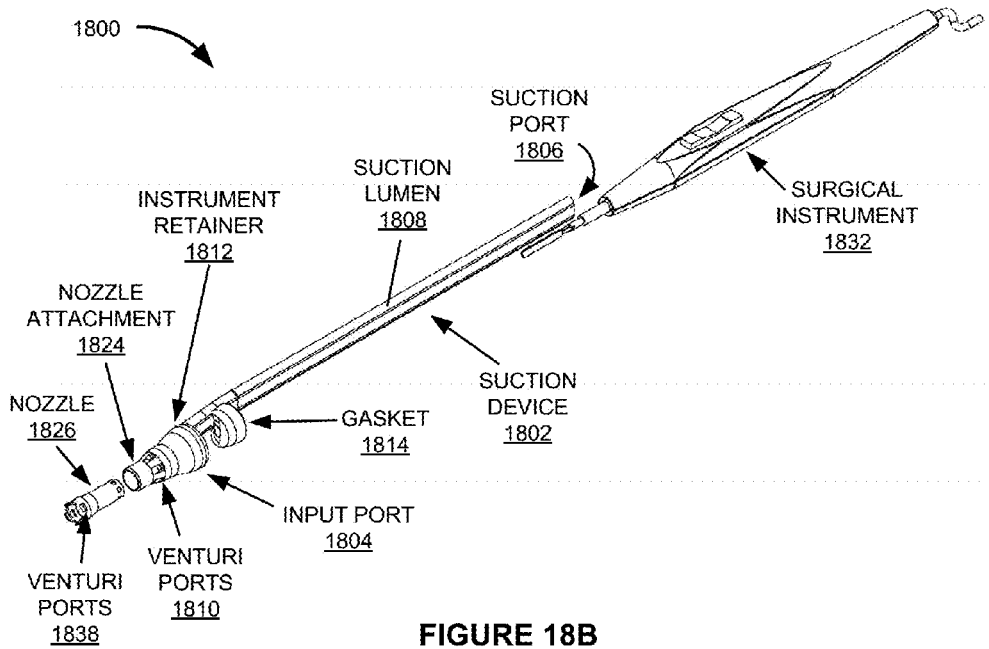
FIG. 18B is an exploded-view diagram illustrating a suction device with surgical instrument.

FIG. 18B is an exploded-view diagram illustrating a suction device with surgical instrument 1800. The elements illustrated in FIG. 18B are the same as FIG. 18A. For the sake of brevity, the elements will not be described further.

Figure 18C:
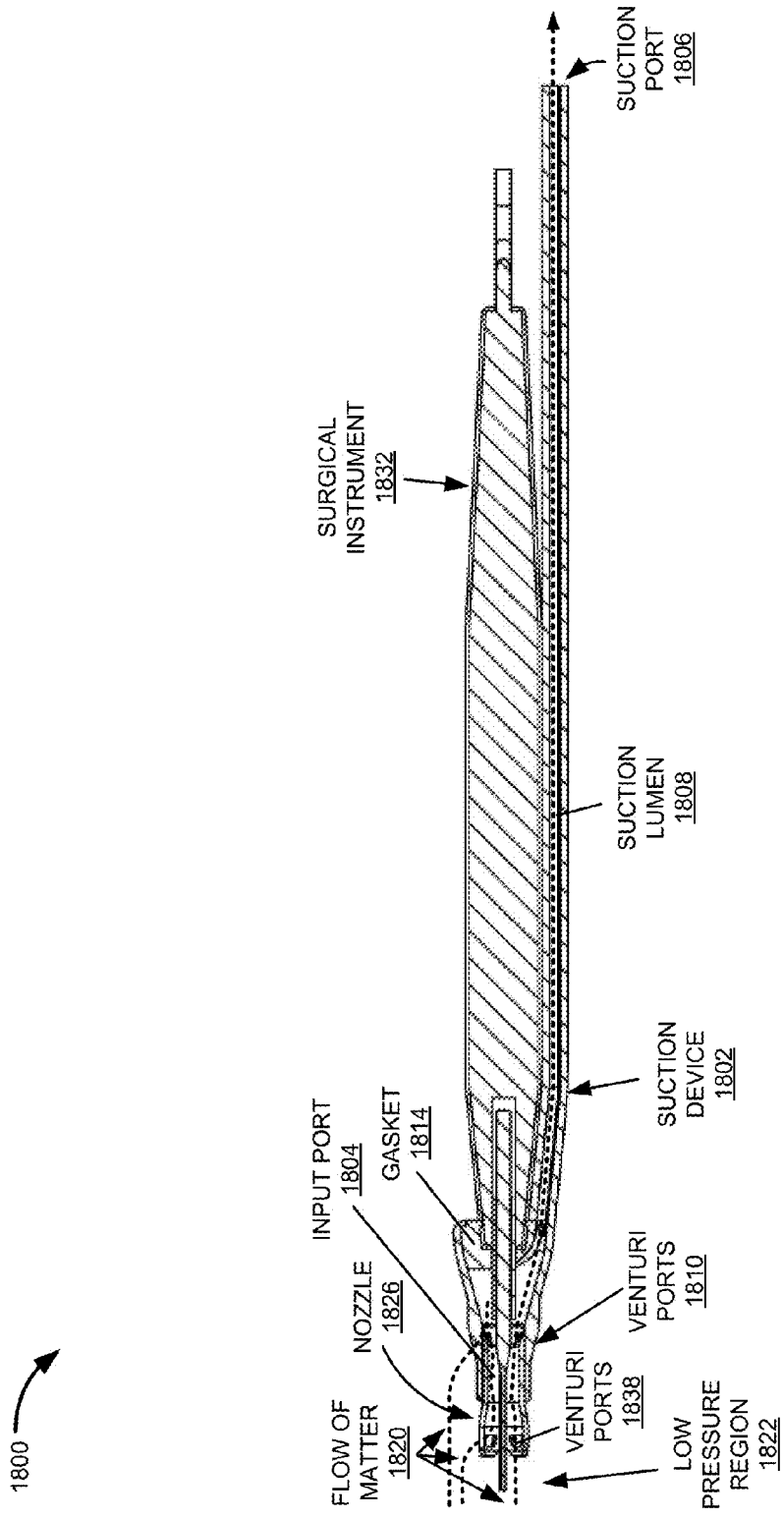
FIG. 18C is a cross-section diagram illustrating the operation of a suction device with surgical instrument.

FIG. 18C is a cross-section diagram illustrating the operation of a suction device with surgical instrument 1800. In operation, suction from a suction source is applied to suction port 1806. Suction lumen 1808 is configured to couple suction port 1806 to input port 1804. Suction lumen 1808 transfers suction received by suction port 1806 to input port 1804. Suction device 1802 is configured to generate low pressure region 1822 near input port 1804 and nozzle 1826 from suction supplied by a suction source. Input port 1804 includes Venturi ports 1810. Venturi ports 1810 pull flow of matter 1820 into input port 1804. Input port 1804 is coupled to nozzle 1826. Nozzle 1826 includes Venturi ports 1838. Venturi ports 1838 pull flow of matter 1820 into nozzle 1826. Gasket 1814 is configured to prevent suction from leaking between a suction device 1802 and surgical instrument 1832 interface. Low pressure region 1822 is at a pressure below the ambient air pressure. This pressure difference causes flow of matter 1820 to be pulled into suction device 1802. Suction device 1802 passes flow of matter 1820 through input port 1804, suction lumen 1808 and out suction port 1806. In some embodiments, a filter may be coupled to suction port 1806 before coupling to a suction source. In some embodiments, a fluid separator may be coupled to suction port 1806 before coupling to a suction source.

Figure 19A:
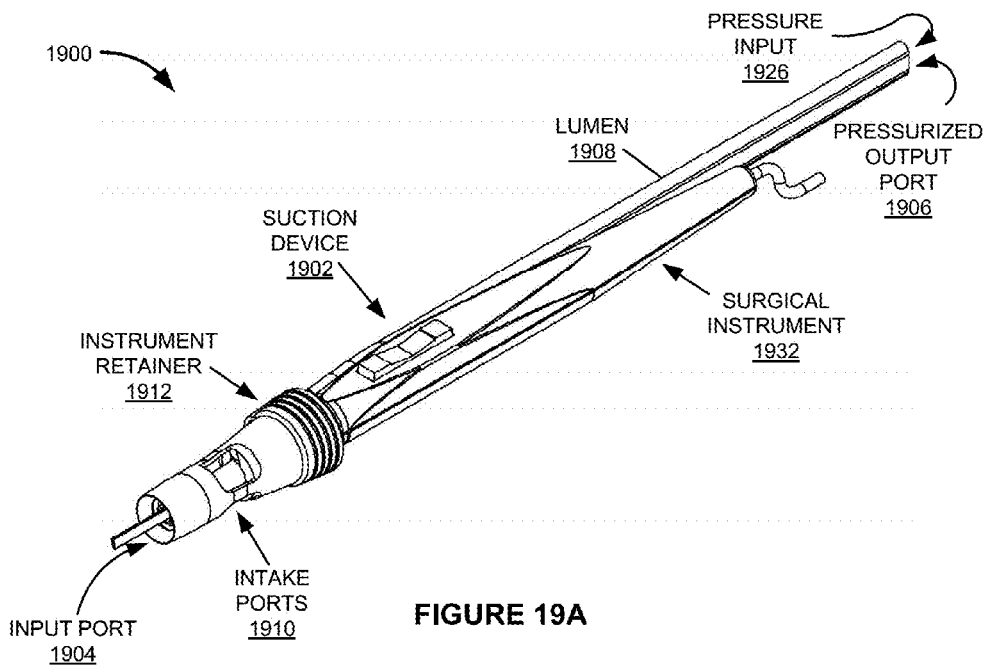
FIG. 19A is a diagram illustrating a suction device with surgical instrument.

FIG. 19A is a diagram illustrating suction device with surgical instrument 1900. Suction device with surgical instrument 1900 includes suction device 1902 and surgical instrument 1932. Suction device 1902 includes fluid accelerator 1934. Fluid accelerator 1934 is configured to generate a low pressure region near input port 1904 and intake ports 1910 from a positive pressure source. The low pressure region is at a pressure below the ambient air pressure, thus causing flow of matter 1920 to be pulled into suction device 1902. The positive pressure source provides pressure that is above the ambient air pressure. Fluid accelerator 1934 is configured to generate suction from positive pressure received by pressure input 1926. The positive pressure source may be an air compressor, compressed gas, or even a human breath. Suction device 1902 includes instrument retainer 1912. Instrument retainer 1912 is configured to couple suction device 1902 to surgical instrument 1932.

Suction device with surgical instrument 1900 includes suction device 1902. Suction device 1902 is an example of positive pressure operated suction device 1100; however, suction device 1902 may include alternative configurations and methods of operation. Suction device 1902 includes input port 1904, pressurized output port 1906, lumen 1908, intake ports 1910, instrument retainer 1912, gasket 1914 and fluid accelerator 1934.

Suction device 1902 includes input port 1904. Input port 1904 is configured to receive a flow of matter. The flow of matter may include liquids, gasses and solids. The flow of matter may include bodily fluids, surgical byproducts and smoke. Input port 1904 is disposed towards the distal end of suction device 1902. Input port 1904 couples to pressurized output port 1906 via lumen 1908. Input port 1904 is in fluidic communication with lumen 1908. Input port 1904 is configured to supply the flow of matter to pressurized output port 1906.

Input port 1904 includes a plurality of intake ports 1910. Intake ports 1910 are configured to suction at least gasses, aerosols and smoke. Intake ports 1910 may improve the suction of a flow of matter suctioned by suction device 1902. Intake ports 1910 may be configured to adjust a ratio of liquids, solids, and gasses suctioned by suction device 1902. Intake ports 1910 may be configured for specific applications. In some embodiments, intake ports 1910 may be configures as Venturi ports. In operation, the Venturi effect increases the velocity of a flow while maintaining a constant volume of flow.

Suction device 1902 includes pressurized output port 1906. Pressurized output port 1906 is disposed at the proximal end of suction device 1902. Pressurized output port 1906 is coupled to lumen 1908. Pressurized output port 1906 is configured to receive a flow of mater from lumen 1908. Pressurized output port 1906 is configured to expel a positive pressure effluent. The positive pressure effluent may include a combination of positive pressure received at pressure input 1926 and a flow of matter received at input port 1904. Pressurized output port 1906 is configured to couple to at least a collection canister, waste drain, fluid separator or a suction source. The suction source may include a vacuum pump, aspirator, positive pressure operation suction source configured to take advantage of the Coanda effect, or some other means of generating suction.

Suction device 1902 includes lumen 1908. Lumen 1908 is disposed within suction device 1902. Lumen 1908 includes a first lumen and a second lumen. The first lumen couples pressure input 1926 to fluid accelerator 1934. The first lumen is configured to supply positive pressure to fluid accelerator 1934. The second lumen couples pressurized output port 1906 to input port 1904. Lumen 1908 is configured to be approximately the same length as surgical instrument 1932 so that pressurized output port 1906 and pressure input 1926 are conveniently located in relation to surgical instrument 1932. This configuration prevents tubing or hoses from interfering with the operation of surgical instrument 1932.

Suction device 1902 includes instrument retainer 1912. Instrument retainer 1912 is configured to couple suction device 1902 to surgical instrument 1932. Instrument retainer 1912 allows surgical instrument 1932 to be attached and detached from suction device 1902 without the use of tools. In some embodiments, instrument retainer 1912 may be configured to accept a particular make and model of surgical instrument. In this example, instrument retainer 1912 is configured to couple suction device 1902 to surgical instrument 1932 using friction.

Suction device 1902 includes gasket 1914. Gasket 1914 is configured to provide a seal between suction device 1902 and surgical instrument 1932. Gasket 1914 may prevent pressure from leaking between suction device 1902 and surgical instrument 1932.

Suction device with surgical instrument 1900 includes surgical instrument 1932. Surgical instrument 1932 may be any surgical instrument that may benefit from suction device 1902. Some surgical instruments that may benefit from suction device 1902 include electrosurgical instruments using heat conduction, diathermy, radio-frequency, and laser methods of operation.

Figure 19B:
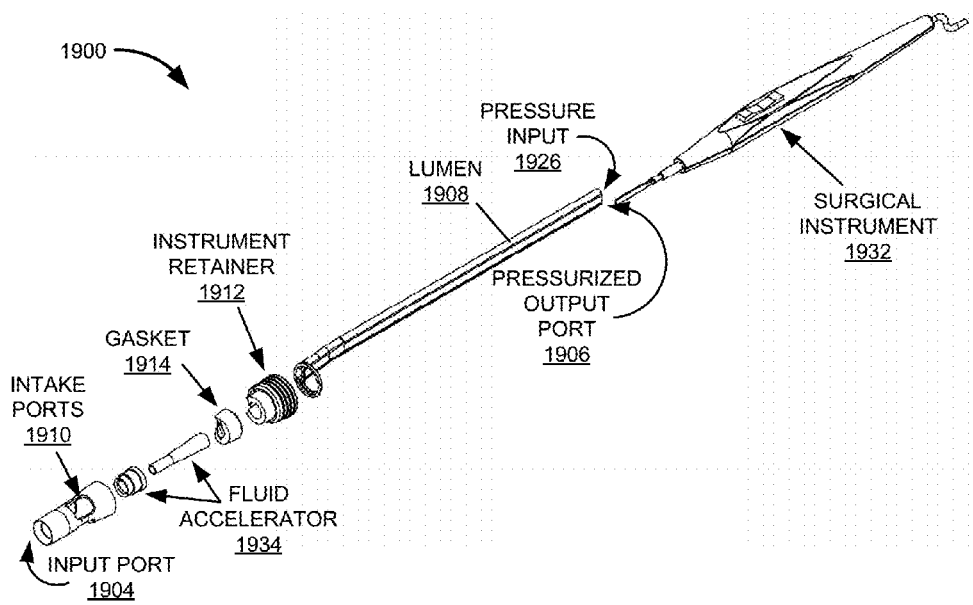
FIG. 19B is an exploded-view diagram illustrating a suction device with surgical instrument.

FIG. 19B is an exploded-view diagram illustrating suction device with surgical instrument 1900. The elements illustrated in FIG. 19B are the same as FIG. 19A. For the sake of brevity, the elements will not be described further.

In operation, pressure input 1926 receives a positive pressure flow. Pressure input 1926 supplies the positive pressure flow to fluid accelerator 1934. Fluid accelerator 1934 is configured to generate a low pressure region near input port 1904 and intake ports 1910. Fluid accelerator 1934 may be configured to utilize the Coanda effect to generate the low pressure region. The low pressure region is at a pressure below the ambient air pressure. This pressure difference causes a flow of matter to be pulled into suction device 1902. Fluid accelerator 1934 includes an annular pressure gap. In some embodiments, the annular pressure gap includes an adjustable dimension. Adjusting the adjustable dimension of the annular pressure gap adjusts a suction ratio of liquids, solids and gasses suction by suction device 1902. The flow of matter is received by input port 1904 and supplied to the second lumen included in lumen 1908. The second lumen is coupled to pressurized output 1906. The flow of matter and pressure received from pressure input 1926 may be combined in fluid accelerator 1934 to form a positive pressure effluent. Pressurized output port 1906 is configured to expel the positive pressure effluent. Pressurized output port 1906 may be coupled to at least a collection canister, filter, fluid separator, waste drain or suction source.

Figure 20A:
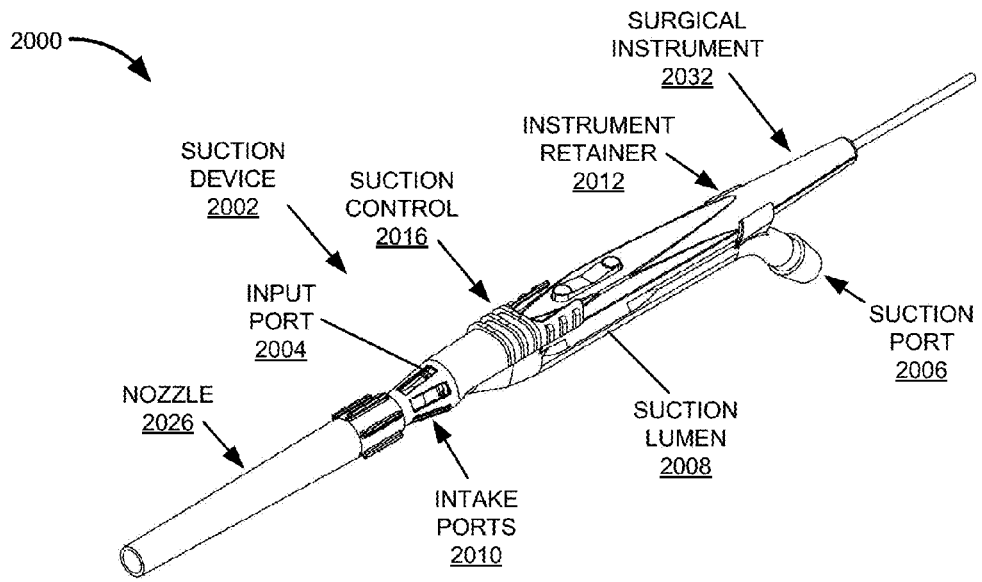
FIG. 20A is a diagram illustrating a suction device with surgical instrument.

FIG. 20A is a diagram illustrating suction device with surgical instrument 2000. Suction device with surgical instrument 2000 includes suction device 2002 and surgical instrument 2032.

Suction device with surgical instrument 2000 includes suction device 2002. Suction device 2002 is an example of suction device 100, suction device 202, suction device 400, suction device 500, suction device 602, suction device 800, suction device 902, suction device 1302 and suction device 1502; however, suction device with surgical instrument 2000 may include alternative configurations or methods of operation. Suction device 2002 includes input port 2004, suction port 2006, suction lumen 2008, instrument retainer 2012, suction control 2016, nozzle attachment 2024 and nozzle 2026.

Suction device 2002 includes input port 2004. Input port 2004 is disposed towards the distal end of suction device 2002. Suction lumen 2008 is configured to couple input port 2004 to suction port 2006. Input port 2004 is configured to receive a flow of matter from nozzle 2026. The flow of matter may include liquids, gasses and solids. The flow of matter may include bodily fluids, surgical byproducts and smoke. Input port 2004 is configured to supply a flow of matter to suction lumen 2008.

Suction device 2002 includes suction port 2006. Suction port 2006 is disposed at the proximal end of suction device 2002. Suction port 2006 is configured at an angle with respect to surgical instrument 2032. The angle allows tubing or hose to be coupled to suction port 2006 without interfering with surgical instrument 2032. Suction port 2006 is coupled to suction lumen 2008. Suction port 2006 is configured to receive a flow of matter from suction lumen 2008. Suction port 2006 is configured to expel a flow of matter. Suction port 2006 is configured to couple to a suction source. The suction source may include a vacuum pump, aspirator, positive pressure operation suction source configured to take advantage of the Coanda effect, or some other means of generating suction. In some embodiments, a suction system may include a separator disposed between suction port 2006 and a suction source to remove waste material from a flow of matter.

Suction device 2002 includes suction lumen 2008. Suction lumen 2008 is disposed within suction device 2002. Suction lumen 2008 is configured to couple input port 2004 to suction port 2006. Suction lumen 2008 includes an open portion configured to allow an obstruction to be removed from suction device 2002. Surgical instrument 2032 may be detached from suction device 2002 to permit access to suction lumen 2008.

Suction device 2002 includes instrument retainer 2012. Instrument retainer 2012 is configured to couple suction device 2002 to surgical instrument 2032. Instrument retainer 2012 allows surgical instrument 2032 to be attached and detached from suction device 2002 without the use of tools. Instrument retainer 2012 includes a clip-type configuration to allow quick attachment and detachment of surgical instrument 2032. In some embodiments, instrument retainer 2012 may be configured to accept a particular make and model of surgical instrument.

Suction device 2002 includes suction control 2016. Suction control 2016 is configured to adjust a suction ratio of liquids, solids and gasses pulled into suction device 2002. Suction control 2016 may adjust a ratio of liquids, solids and gasses by adjusting the location of nozzle 2026. Suction control 2016 may be configured to adjust dimensions of intake ports 2010 included at input port 2004. Suction control 2016 comprises a sliding member. Suction control 2016 may be configured to extend and retract nozzle 2026 in order to selectively adjust a ratio of liquids, solids and gasses suctioned by suction device 2002. In some embodiments, suction control 2016 may include a means for securing a location of suction control 2016. The means for securing suction control 2016 may include detents, friction fit, notches or some other means for securing a location of suction control 2016.

Figure 20B:
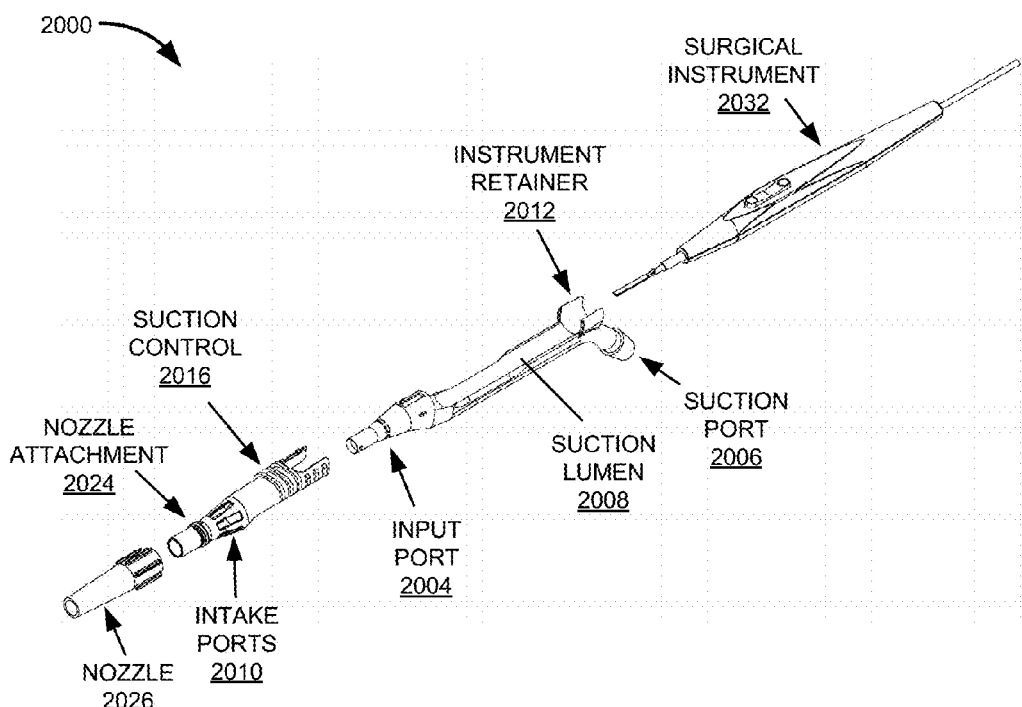
FIG. 20B is an exploded-view diagram illustrating a suction device with surgical instrument.

Suction device 2002 includes nozzle attachment 2024 (illustrated in FIG. 20B). Nozzle attachment 2024 is configured to accept a variety of different nozzles 2026 suited for an intended application. Nozzle attachment 2024 includes threads for couple nozzle 2026 to suction device 2002. In some embodiments, nozzle attachment 2024 may include Luer locks, quick-disconnect, or some other fitting configured to allow attachment of nozzle 2026.

Suction device 2002 includes nozzle 2026. Nozzle 2026 is configured to couple to nozzle attachment 2024. The shape and configuration of nozzle 2026 may vary depending upon the intended application. For example, FIGS. 20A and 20B illustrate two different embodiment of nozzle 2026.

Suction device with surgical instrument 2000 includes surgical instrument 2032. Surgical instrument 2032 may be any surgical instrument that may benefit from suction device 2002. Some surgical instruments that may benefit from suction device 2002 include electrosurgical instruments using heat conduction, diathermy, radio-frequency, and laser methods of operation.

FIG. 20B is an exploded-view diagram illustrating a suction device with surgical instrument 2000. The elements illustrated in FIG. 20B are the same as FIG. 20A. For the sake of brevity, the elements will not be described further.

Figure 21A:
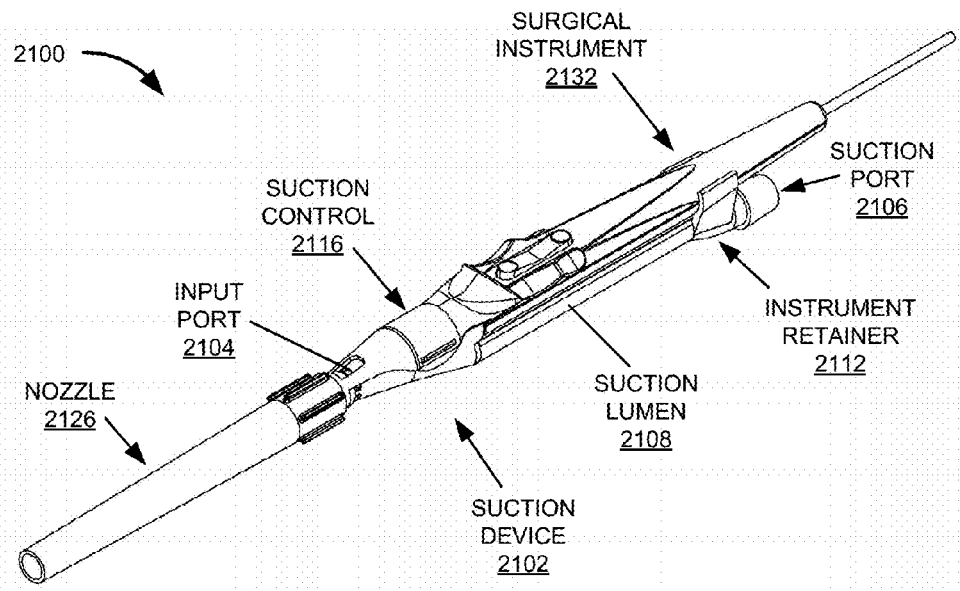
FIG. 21A is a diagram illustrating a suction device with surgical instrument.

FIG. 21A is a diagram illustrating suction device with surgical instrument 2100. Suction device with surgical instrument 2100 includes suction device 2102 and surgical instrument 2132.

Suction device with surgical instrument 2100 includes suction device 2102. Suction device 2102 is an example of suction device 100, suction device 202, suction device 400, suction device 500, suction device 602, suction device 800, suction device 902, suction device 1302 and suction device 1502; however, suction device 2102 with surgical instrument 2100 may include alternative configurations or methods of operation. Suction device 2102 includes input port 2104, suction port 2106, suction lumen 2108, instrument retainer 2112, suction control 2116, nozzle attachment 2124 and nozzle 2126.

Suction device 2102 includes input port 2104. Input port 2104 is disposed towards the distal end of suction device 2102. Suction lumen 2108 is configured to couple input port 2104 to suction port 2106. Input port 2104 is configured to receive a flow of matter from nozzle 2126. The flow of matter may include liquids, gasses and solids. The flow of matter may include bodily fluids, surgical byproducts and smoke. Input port 2104 is configured to supply a flow of matter to suction lumen 2108.

Suction device 2102 includes suction port 2106. Suction port 2106 is disposed at the proximal end of suction device 2102. Suction port 2106 is coupled to suction lumen 2108. Suction port 2106 is configured to receive a flow of matter from suction lumen 2108. Suction port 2106 is configured to expel a flow of matter. Suction port 2106 is configured to couple to a suction source. The suction source may include a vacuum pump, aspirator, positive pressure operation suction source configured to take advantage of the Coanda effect, or some other means of generating suction. In some embodiments, a suction system may include a separator disposed between suction port 2106 and a suction source to remove waste material from a flow of matter.

Suction device 2102 includes suction lumen 2108. Suction lumen 2108 is disposed within suction device 2102. Suction lumen 2108 is configured to couple input port 2104 to suction port 2106. Suction lumen 2108 includes an open portion configured to allow an obstruction to be removed from suction device 2102. Surgical instrument 2132 may be detached from suction device 2102 to permit access to suction lumen 2108.

Suction device 2102 includes instrument retainer 2112. Instrument retainer 2112 is configured to couple suction device 2102 to surgical instrument 2132. Instrument retainer 2112 allows surgical instrument 2132 to be attached and detached from suction device 2102 without the use of tools. Instrument retainer 2112 includes a clip-type configuration to allow quick attachment and detachment of surgical instrument 2132. In some embodiments, instrument retainer 2112 may be configured to accept a particular make and model of surgical instrument 2132.

Suction device 2102 includes suction control 2116. Suction control 2116 is configured to adjust a suction ratio of liquids, solids and gasses pulled into suction device 2102. Suction control 2116 may adjust a ratio of liquids, solids and gasses suctioned by suction device 2102 by adjusting the location of nozzle 2126 in relation to surgical device 2132. Suction control 2116 comprises a sliding member. Suction control 2116 may be configured for adjustment by one hand. Suction control 2116 includes a means for securing a location of suction control 2116. The means for securing suction control 2116 may include detents, friction fit, notches or some other means for securing a location of suction control 2116.

Figure 21B:
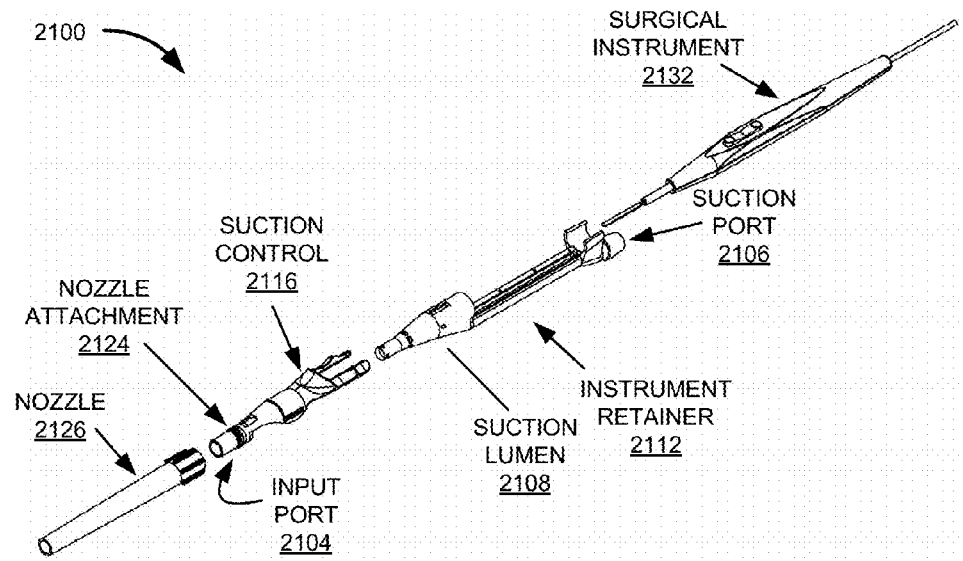
FIG. 21B is an exploded-view diagram illustrating a suction device with surgical instrument.

Suction device 2102 includes nozzle attachment 2124 (illustrated in FIG. 21B). Nozzle attachment 2124 is configured to accept a variety of different nozzles 2126 suited for an intended application. Nozzle attachment 2124 includes quick-disconnect type fitting for coupling nozzle 2126 to suction device 2102. In some embodiments, nozzle attachment 2124 may include threads, Luer locks, or some other fitting configured to allow attachment of nozzle 2126.

Suction device 2102 includes nozzle 2126. Nozzle 2126 is configured to couple to nozzle attachment 2124. The shape and configuration of nozzle 2126 may vary depending upon the intended application. Nozzle 2126 may be a commercially available nozzle.

Suction device with surgical instrument 2100 includes surgical instrument 2132. Surgical instrument 2132 may be any surgical instrument that may benefit from suction device 2102. Some surgical instruments that may benefit from suction device 2102 include electrosurgical instruments using heat conduction, diathermy, radio-frequency, and laser methods of operation.

FIG. 21B is an exploded-view diagram illustrating suction device with surgical instrument 2100. The elements illustrated in FIG. 21B are the same as FIG. 21A. For the sake of brevity, the elements will not be described further.

FIG. 21C is a diagram illustrating the operation of suction device with surgical instrument 2100 in the event of an obstruction. FIG. 21C illustrates suction device with surgical instrument 2100 with obstruction 2150. Obstruction 2150 may prevents all, or a portion of, flow of matter 2120 from passing through suction device 2102.

FIG. 21D is a diagram illustrating the operation of clearing a suction device with surgical instrument 2100. Instrument retainer 2112 is configured to allow surgical instrument 2132 to be attached and detached from suction device 2102 without the use of tools or other devices. In the event that obstruction 2150 has prevented flow of matter 2120 from passing through suction device 2102, surgical instrument 2132 may be detached from suction device 2102 to remove obstruction 2150.

FIG. 21D illustrates surgical instrument 2132 detached from suction device 2102. Instrument retainer 2112 is configured to allow attachment and detachment of surgical instrument 2132 from suction device 2102. FIG. 21D illustrates surgical instrument 2132 detached from suction device 2102. Suction lumen 2108 may be accessed to clear obstruction 2150 when surgical instrument 2132 is detached from suction device 2102. FIG. 21D illustrates obstruction 2150 removed from suction device 2102.

Figure 22:
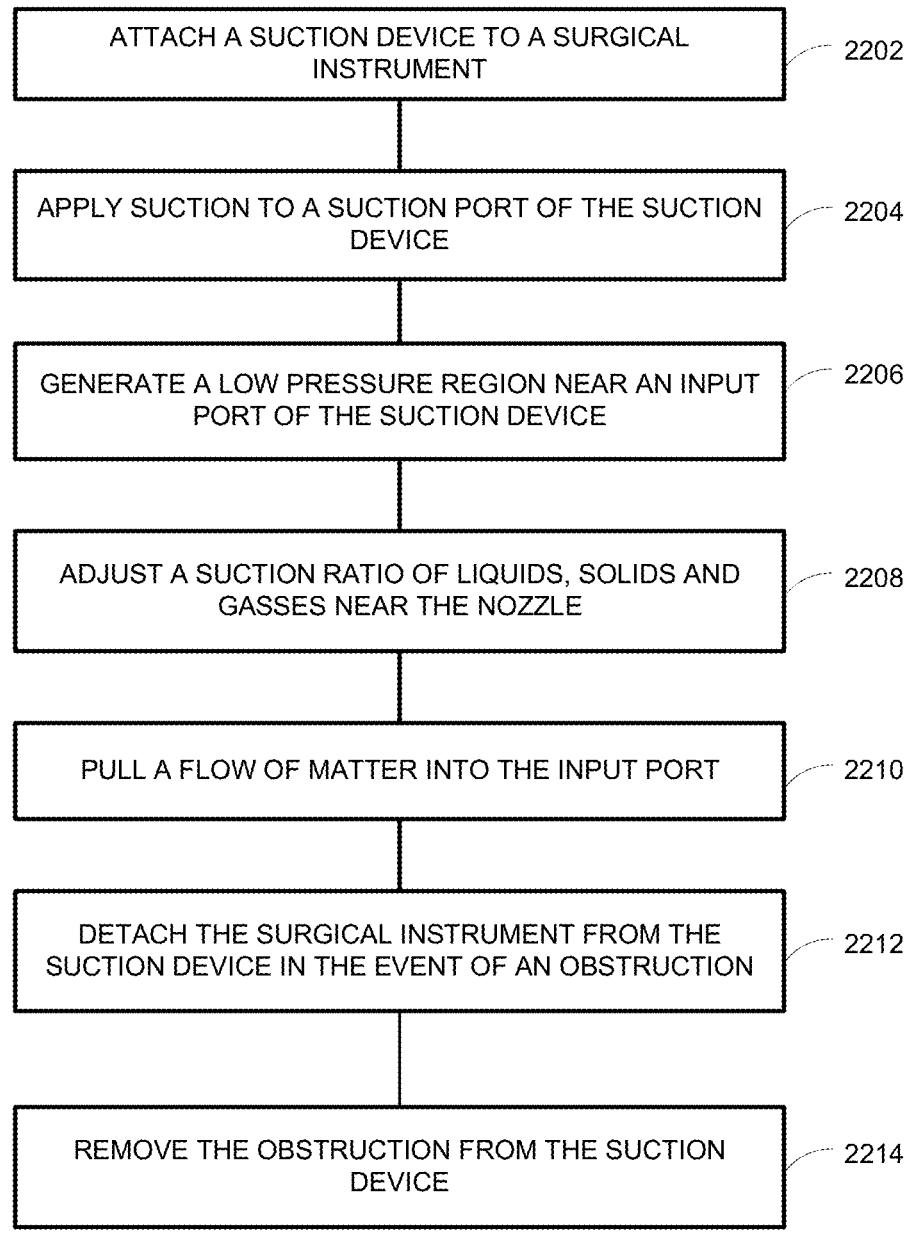
FIG. 22 is a diagram illustrating a method of operating a suction device with surgical instrument.

FIG. 22 is a diagram illustrating a method of operating a suction device with surgical instrument. The steps illustrated in FIG. 22 may be performed by one or more elements of suction device with surgical instrument 2100. A surgical instrument is attached to suction device (2202). For example, suction device 2102 includes instrument retainer 2112. Instrument retainer 2112 is configured to attach surgical instrument 2132 to suction device 2102. Instrument retainer 2112 is configured such that surgical instrument 2132 may be quickly attached or detached from suction device 2102 without the use of tools. Suction is applied to a suction port of a suction device (2204). For example, suction port 2106 is configured to couple to a suction source. The suction source is configured to apply suction to suction port 2106 of suction device 2102. A low pressure region is generated near an input port of the suction device (2206). For example, suction device 2102 is configured to generate a low pressure region near nozzle 2126 of suction device 2102 from the suction source. In some embodiments, input port 2104 may be used without nozzle 2126. A suction ratio of liquids, solids and gasses adjusted near the nozzle (2208). For example, suction device 2102 includes suction control 2116. Suction control 2116 is configured to adjust a ratio of liquids, solids and gasses suctioned by suction device 2102. A flow of matter is pulled into the input port (2210). For example, input port 2104 is configured to receive flow of matter 2120. Low pressure region 2122 is at a pressure below an ambient air pressure. Low pressure region 2122 is configured to pull flow of matter 2120 into input port 2104. The surgical instrument is detached from the suction device in the event of an obstruction (2212). For example, instrument retainer 2112 is configured to allow surgical instrument 2132 to be easily detached from suction device 2102. The obstruction is removed from the suction device (2214). For example, suction lumen 2108 includes an open portion configured to permit obstruction 2150 to be removed when surgical instrument 2132 is detached.

Figure 23A:
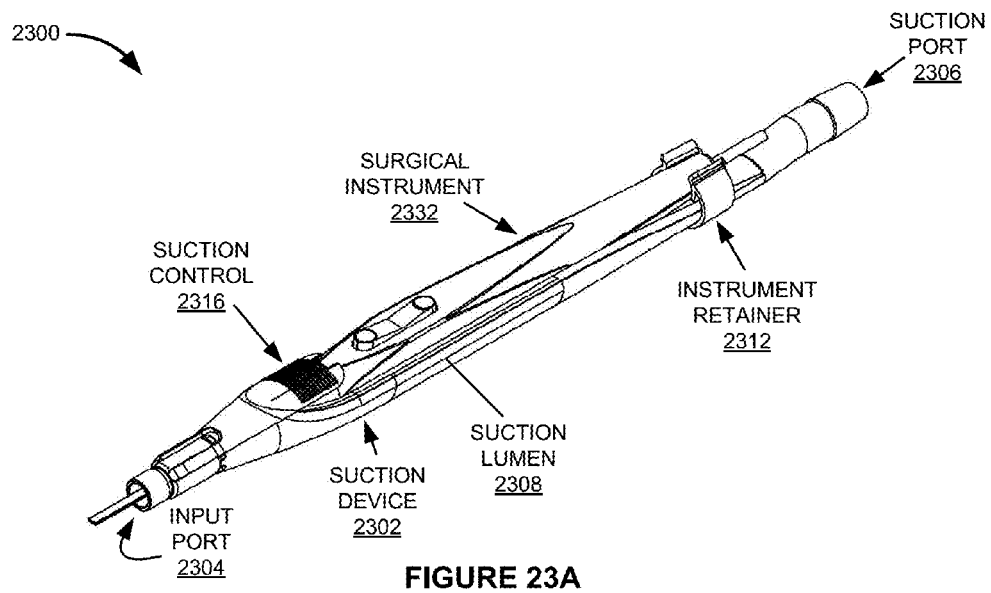
FIG. 23A is a diagram illustrating a suction device with surgical instrument.

FIG. 23A is a diagram illustrating suction device with surgical instrument 2300. Suction device with surgical instrument 2300 includes suction device 2302 and surgical instrument 2332.

Suction device with surgical instrument 2300 includes suction device 2302. Suction device 2302 is an example of suction device 100, suction device 202, suction device 400, suction device 500, suction device 602, suction device 800, suction device 902, suction device 1302 and suction device 1502; however, suction device 2302 may include alternative configurations or methods of operation. Suction device 2302 includes input port 2304, suction port 2306, suction lumen 2308, instrument retainer 2312, and suction control 2316. Suction device 2302 is configured to couple to a suction source. The suction source may be a vacuum pump, aspirator, positive pressure operated suction source configured to take advantage of the Coanda effect, or some other means of generating suction. The suction source is configured to generate a low pressure region near input port 2304. The low pressure region is at a pressure below the ambient air pressure, thus causing a flow of matter to be pulled into input port 2304. Suction device 2302 is configured to couple to surgical instrument 2332 via instrument retainer 2312.

Suction device 2302 includes input port 2304. Input port 2304 is disposed towards the distal end of suction device 2302. Input port 2304 is coupled to suction lumen 2308. Input port 2304 is configured to receive a flow of matter. The flow of matter may include liquids, gasses and solids. The flow of matter may include bodily fluids, surgical byproducts and smoke. Input port 2304 is configured to supply a flow of matter to suction lumen 2308.

Suction device 2302 includes suction port 2306. Suction port 2306 is disposed at the proximal end of suction device 2302. Suction port 2306 is coupled to suction lumen 2308. Suction port 2306 is configured to receive a flow of matter from suction lumen 2308. Suction port 2306 is configured to expel a flow of matter. Suction port 2306 is configured to couple to a suction source. The suction source may include a vacuum pump, aspirator, positive pressure operation suction source configured to take advantage of the Coanda effect, or some other means of generating suction.

Suction device 2302 includes suction lumen 2308. Suction lumen 2308 is disposed within suction device 2302. Suction lumen 2308 is configured to couple input port 2304 to suction port 2306. Suction lumen 2308 includes an open portion that is configured to allow access to suction lumen 2308. The open portion of suction lumen 2308 is closed by gasket 2314. Gasket 2314 is comprised of a flexible material. In the event of an obstruction, surgical instrument 2332 may be removed to access gasket 2314. Gasket 2314 may be manipulated to free an obstruction within suction lumen 2308.

Suction device 2302 includes instrument retainer 2312. Instrument retainer 2312 is configured to couple suction device 2302 to surgical instrument 2332. Instrument retainer 2312 allows surgical instrument 2332 to be attached and detached from suction device 2302 without the use of tools. Instrument retainer 2312 is configured to include a clip-type configuration to allow quick attachment and detachment of surgical instrument 2332 without tools. In some embodiments, instrument retainer 2312 may be configured to accept a particular make and model of surgical instrument.

Suction device 2302 includes gasket 2314. Gasket 2314 is configured to provide a seal between suction device 2302 and surgical instrument 2332. Gasket 2314 may prevent suction from a suction source from leaking between a suction device 2302 and surgical instrument 2332 interface. Gasket 2314 is comprised of a flexible material. In the event of an obstruction, surgical instrument 2332 may be removed to access gasket 2314. Gasket 2314 may be manipulated to free an obstruction within suction lumen 2308.

Suction device 2302 includes suction control 2316. Suction control 2316 is configured to adjust a suction ratio of liquids, solids and gasses pulled into suction device 2302. Suction control 2316 may adjust a ratio of liquids, solids and gasses suctioned by suction device 2302 by adjusting the location of nozzle 2326. Suction control 2316 includes a sliding member. The sliding member may be configured to extend and retract nozzle 2326 in order to selectively adjust a ratio of liquids, solids and gasses suctioned by suction device 2302. In some embodiments, suction control 2316 may include a means for securing a location of suction control 2316. The means for securing suction control 2316 may include detents, friction fit, notches or some other means for securing a location of suction control 2316.

Suction device with surgical instrument 2300 includes surgical instrument 2332. Surgical instrument 2332 may be any surgical instrument that may benefit from suction device 2302. Some surgical instruments that may benefit from suction device 2302 include electrosurgical instruments using heat conduction, diathermy, radio-frequency, and laser methods of operation.

Figure 23B:
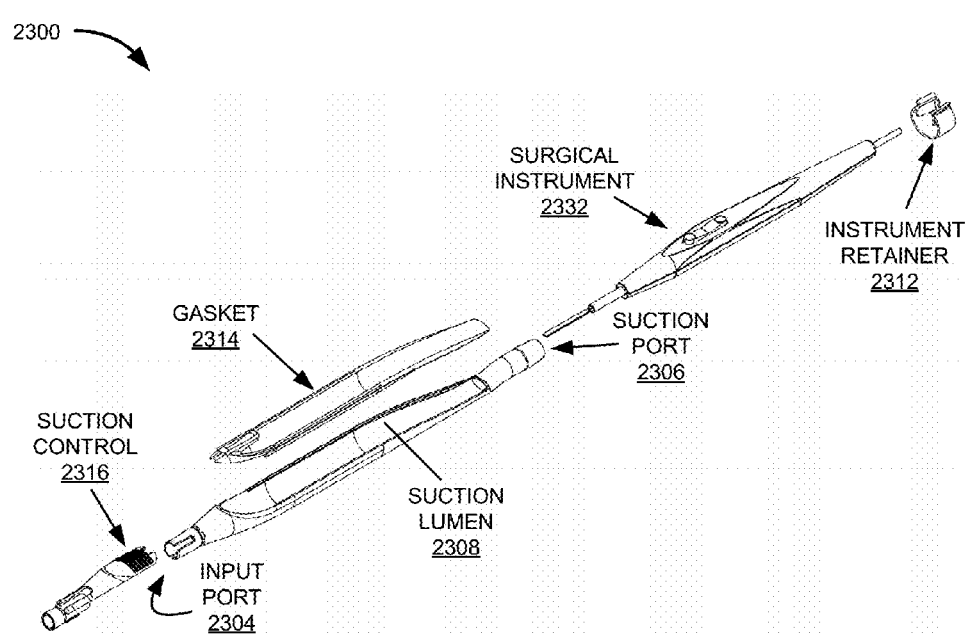
FIG. 23B is an exploded-view diagram illustrating a suction device with surgical instrument.

FIG. 23B is an exploded-view diagram illustrating suction device with surgical instrument 2300. The elements illustrated in FIG. 23B are the same as FIG. 23A. For the sake of brevity, the elements will not be described further.

FIG. 23C is a diagram illustrating the operation of suction device with surgical instrument 2300 in the event of an obstruction. Obstruction 2350 may prevents all, or a portion of, flow of matter 2320 from passing through suction device 2302.

FIG. 23D is a diagram illustrating the operation of clearing suction device with surgical instrument 2300. Instrument retainer 2312 is configured to allow surgical instrument 2332 to be attached and detached from suction device 2302 without the use of tools or other devices. In the event that obstruction 2350 has prevented flow of matter 2320 from passing through suction device 2302, surgical instrument 2332 may be detached from suction device 2302 to remove obstruction 2350.

Figure 24:
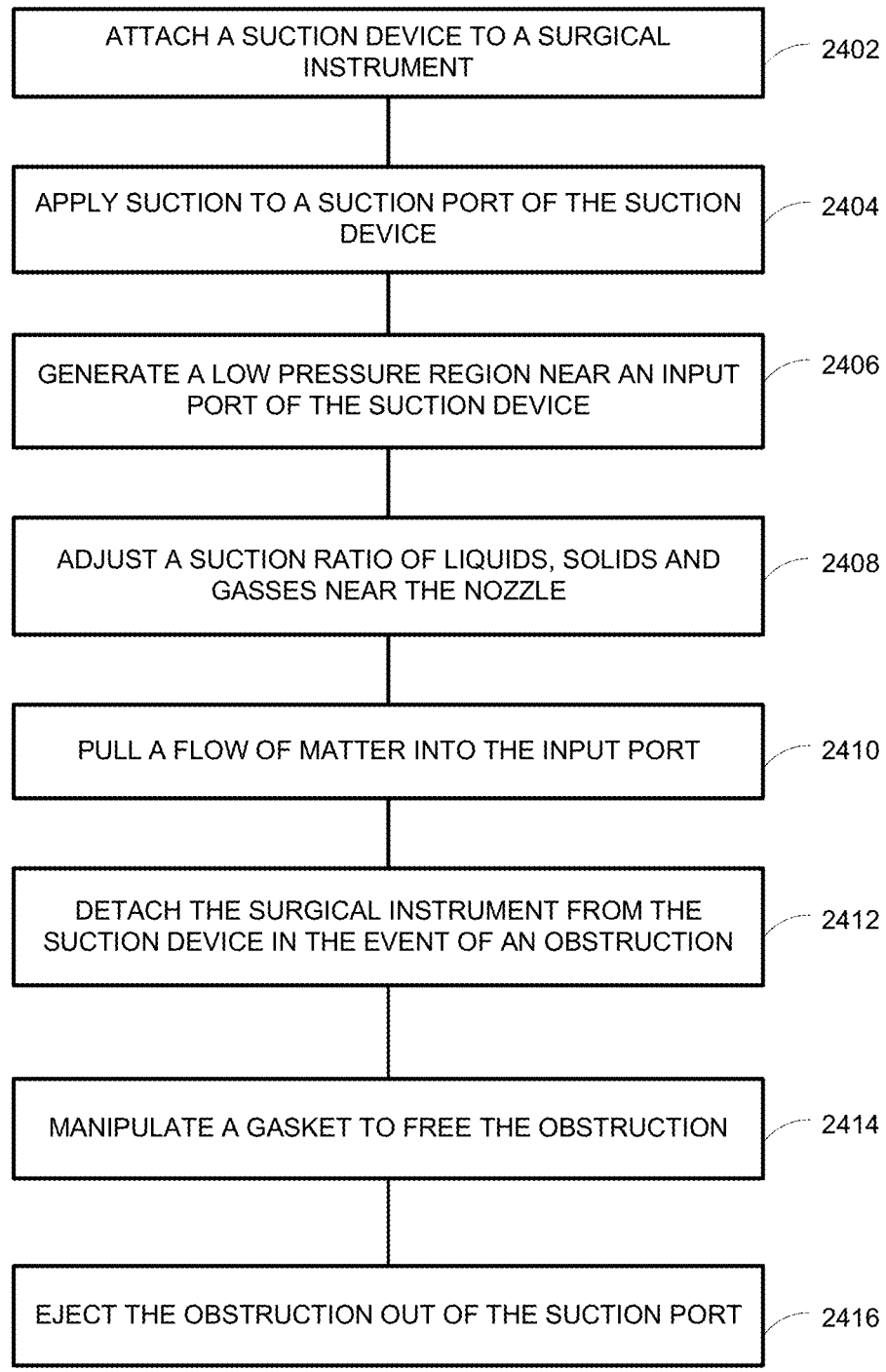
FIG. 24 is a diagram illustrating a method of operating a suction device with surgical instrument.

FIG. 24 is a diagram illustrating a method of operating a suction device. The steps illustrated in FIG. 24 may be performed by one or more elements of suction device with surgical instrument 2300. A surgical instrument is attached to suction device (2402). For example, suction device 2302 includes instrument retainer 2312. Instrument retainer 2312 is configured to attach surgical instrument 2332 to suction device 2302. Instrument retainer 2312 is configured such that surgical instrument 2332 may be quickly attached or detached from suction device 2302. Suction is applied to a suction port of a suction device (2404). For example, suction port 2306 is configured to couple to a suction source. The suction source is configured to apply suction to suction port 2306 of suction device 2302. A low pressure region is generated near an input port of the suction device (2406). For example, suction device 2302 is configured to generate low pressure region 2322 near input port 2304 of suction device 2302 from the suction source. A suction ratio of liquids, solids and gasses adjusted near the nozzle (2408). For example, suction device 2302 includes suction control 2316. Suction control 2316 is configured to adjust a ratio of liquids, solids and gasses suctioned by suction device 2302. A flow of matter is pulled into the input port (2410). For example, input port 2304 is configured to receive flow of matter 2320. Low pressure region 2322 is at a pressure below an ambient air pressure. Low pressure region 2322 is configured to pull flow of matter 2320 into input port 2304. The surgical instrument is detached from the suction device in the event of an obstruction (2412). For example, instrument retainer 2312 is configured to allow surgical instrument 2332 to be easily detached from suction device 2302 with the use of tools or other devices. A gasket is manipulated to free the obstruction (2414). For example, suction device 2302 includes gasket 2314. Gasket 2314 comprises a flexible membrane. The flexible membrane may be manipulated to change the size and shape of suction lumen 2308. Changing the size and shape of suction lumen 2308 may free obstruction 2350. The obstruction is ejected out of the suction port (2416). For example, FIG. 23D illustrates obstruction 2350 freed from suction lumen 2308 after gasket 2314 has been manipulated. Obstruction 2350 may be ejected out suction port 2306 along with flow of matter 2320.

Figure 25A:
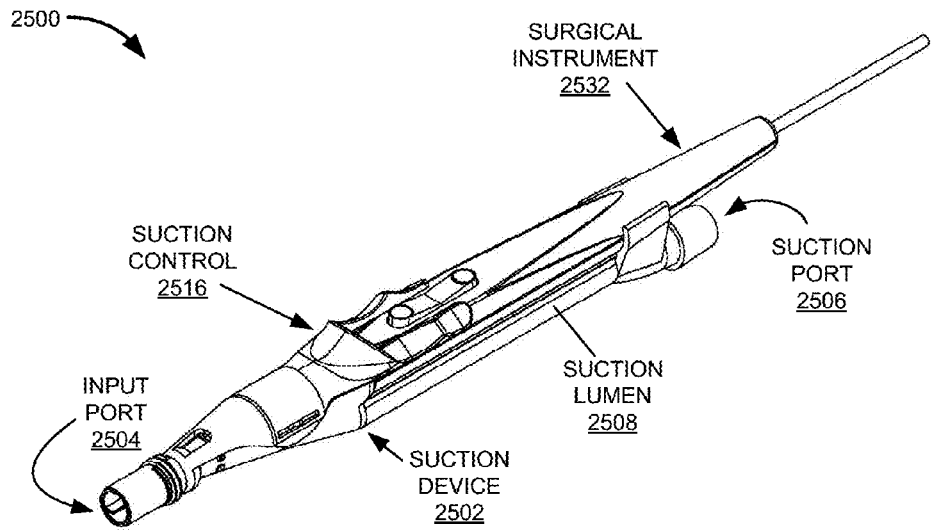
FIG. 25A is a diagram illustrating a suction device with surgical instrument.

FIG. 25A is a diagram illustrating a suction device with surgical instrument 2500. Suction device with surgical instrument 2500 includes suction device 2502 and surgical instrument 2532.

Suction device with surgical instrument 2500 includes suction device 2502. Suction device 2502 is an example of suction device 100, suction device 202, suction device 400, suction device 500, suction device 602, suction device 800, suction device 902, suction device 1302 and suction device 1502; however, suction device 2502 may include alternative configurations or methods of operation. Suction device 2502 includes input port 2504, suction port 2506, suction lumen 2508, instrument retainer 2512, gasket 2514 and suction control 2516. Suction device 2502 is configured to couple to a suction source. The suction source may be a vacuum pump, aspirator, positive pressure operated suction source configured to take advantage of the Coanda effect, or some other means of generating suction. The suction source is configured to generate a low pressure region near input port 2504. The low pressure region is at a pressure below the ambient air pressure, thus causing a flow of matter to be pulled into input port 2504. Suction device 2502 is configured to couple to surgical instrument 2532 via instrument retainer 2512.

Suction device 2502 includes input port 2504. Input port 2504 is disposed towards the distal end of suction device 2502. Input port 2504 is coupled to suction lumen 2508. Input port 2504 is configured to receive a flow of matter. The flow of matter may include liquids, gasses and solids. The flow of matter may include bodily fluids, surgical byproducts and smoke. Input port 2504 is configured to supply flow of matter 2520 to suction lumen 2508.

Suction device 2502 includes suction port 2506. Suction port 2506 is disposed at the proximal end of suction device 2502. Suction port 2506 is coupled to suction lumen 2508. Suction port 2506 is configured to receive a flow of matter from suction lumen 2508. Suction port 2506 is configured to expel a flow of matter. Suction port 2506 is configured to couple to a suction source. The suction source may include a vacuum pump, aspirator, positive pressure operation suction source configured to take advantage of the Coanda effect, or some other means of generating suction.

Suction device 2502 includes suction lumen 2508. Suction lumen 2508 is disposed within suction device 2502. Suction lumen 2508 is configured to couple input port 2504 to suction port 2506. Gasket 2514 includes obstruction clearing port 2540. Obstruction clearing port 2544 is configured to permit access to suction lumen 2508.

Suction device 2502 includes instrument retainer 2512. Instrument retainer 2512 is configured to couple suction device 2502 to surgical instrument 2532. Instrument retainer 2512 allows surgical instrument 2532 to be attached and detached from suction device 2502 without the use of tools. Instrument retainer 2512 is configured to include a clip-type configuration to allow quick attachment and detachment of surgical instrument 2532 without tools. In some embodiments, instrument retainer 2512 may be configured to accept a particular make and model of surgical instrument.

Suction device 2502 include gasket 2514. Gasket 1514 includes obstruction clearing port 2540 and suction control positioner 2542. Gasket 2514 is configured to provide a seal between suction device 2502 and surgical instrument 2532. The seal may prevent suction leaks. Gasket 2514 includes obstruction clearing port 2540. Obstruction clearing port 2540 is an opening within gasket 2514. Obstruction clearing port 2540 permits access to the proximal end of input port 2504 and the distal end of suction lumen 2508 to allow an obstruction to be removed from suction device 2502. Obstruction clearing port 2540 is closed by a portion of surgical instrument 2532 when surgical instrument 2532 is coupled to suction device 2502.

Suction device 2502 includes suction control 2516. Suction control 2516 is configured to adjust a suction ratio of liquids, solids and gasses pulled into suction device 2502. Suction control 2516 may adjust a ratio of liquids, solids and gasses suctioned by suction device 2502 by adjusting the location of input port 2504 with respect to a working end of surgical instrument 2532. Suction control 2516 includes a sliding member. The sliding member may be configured to extend and retract input port 2504 in order to selectively adjust a ratio of liquids, solids and gasses suctioned by suction device 2502. Gasket 2514 includes suction control positioner 2542. Suction control positioner 2542 is a feature integral to gasket 2514. Suction control positioner 2542 uses friction to hold a position of suction control 2516.

Suction device with surgical instrument 2500 includes surgical instrument 2532. Surgical instrument 2532 may be any surgical instrument that may benefit from suction device 2502. Some surgical instruments that may benefit from suction device 2502 include electrosurgical instruments using heat conduction, diathermy, radio-frequency, and laser methods of operation.

Figure 25B:
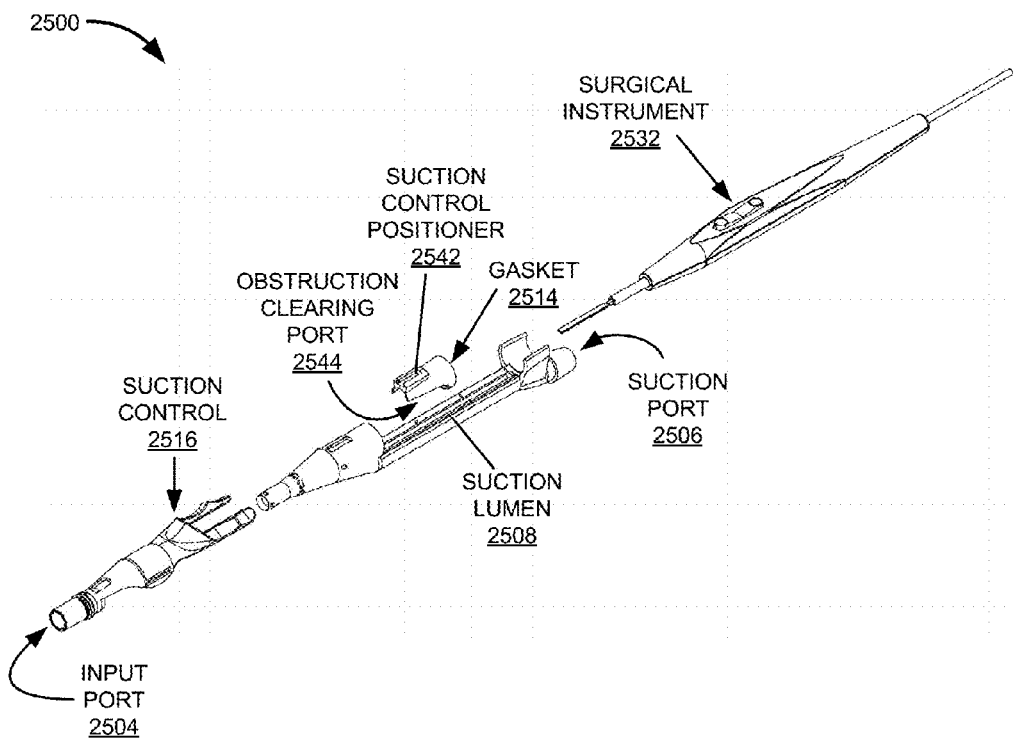
FIG. 25B is an exploded-view diagram illustrating a suction device with surgical instrument.

FIG. 25B is an exploded-view diagram illustrating a suction device with surgical instrument 2500. The elements illustrated in FIG. 25B are the same as FIG. 25A. For the sake of brevity, the elements will not be described further.

FIG. 25C is a diagram illustrating the operation of suction device with surgical instrument 2500 in the event of an obstruction. Obstruction 2550 may prevent all, or a portion of, flow of matter 2520 from passing through suction device 2502. As illustrated in FIG. 25C, obstruction 2550 is blocking flow of matter 2520 from passing through suction lumen 2508.

FIG. 25D is a diagram illustrating the operation of clearing suction device with surgical instrument 2500. Instrument retainer 2512 is configured to allow surgical instrument 2532 to be attached and detached from suction device 2502 without the use of tools or other devices. In the event that obstruction 2550 has prevented flow of matter 2520 from passing through suction device 2502, surgical instrument 2532 may be detached from suction device 2502 to access obstruction clearing port 2540. Obstruction clearing port 2540 is configured to allow access to input port 2504 and suction lumen 2508 when surgical instrument 2532 is detached from suction device 2502. Obstruction 2550 may be removed from suction device 2502 through obstruction clearing port 2540.

Figure 26:
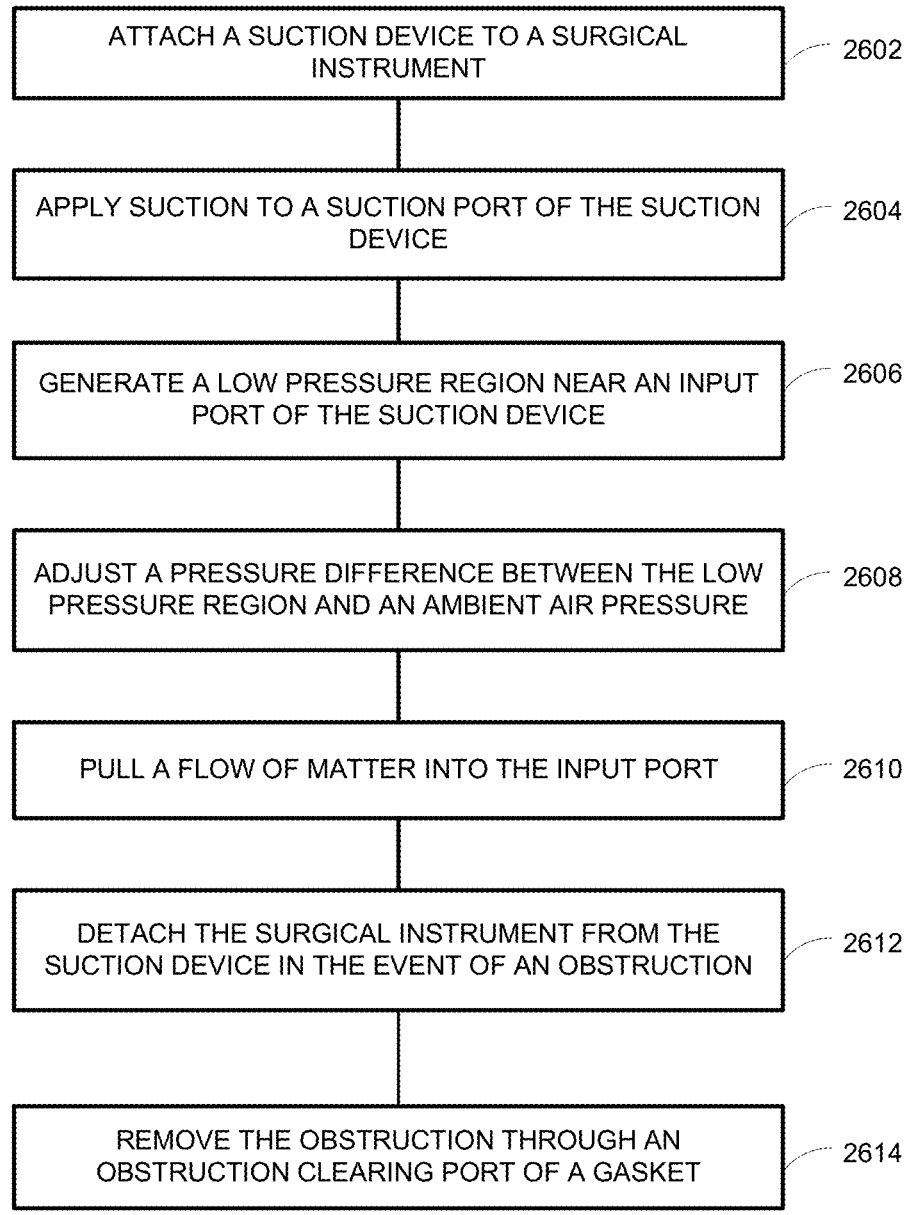
FIG. 26 is a diagram illustrating a method of operating a suction device with surgical instrument.

FIG. 26 is a diagram illustrating a method of operating a suction device with surgical instrument. The steps illustrated in FIG. 26 may be performed by one or more elements of suction device with surgical instrument 2500. A surgical instrument is attached to suction device (2602). For example, suction device 2502 includes instrument retainer 2512. Instrument retainer 2512 is configured to attach surgical instrument 2532 to suction device 2502. Instrument retainer 2512 is configured such that surgical instrument 2532 may be quickly attached or detached from suction device 2502 without the use of tools or other devices. Suction is applied to a suction port of a suction device (2604). For example, suction port 2506 is configured to couple to a suction source. The suction source is configured to apply suction to suction port 2506 of suction device 2502. A low pressure region is generated near an input port of the suction device (2606). For example, suction device 2502 is configured to generate low pressure region 2522 near input port 2504 of suction device 2502 from the suction source. A suction ratio of liquids, solids and gasses adjusted near the nozzle (2608). For example, suction device 2502 includes suction control 2516. Suction control 2516 is configured to adjust a ratio of liquids, solids and gasses suctioned by suction device 2502. A flow of matter is pulled into the input port (2610). For example, input port 2504 is configured to receive flow of matter 2520. Low pressure region 2522 is at a pressure below an ambient air pressure. Low pressure region 2522 is configured to pull flow of matter 2520 into input port 2504. The surgical instrument is detached from the suction device in the event of an obstruction (2612). For example, instrument retainer 2512 is configured to allow surgical instrument 2532 to be easily detached from suction device 2502 with the use of tools or other devices. The obstruction is removed through an obstruction clearing port of a gasket (2614). For example, suction device 2502 includes gasket 2514. Gasket 2514 includes obstruction clearing port 2540. Obstruction clearing port 2540 is configured to permit access to input port 2504 and suction lumen 2508. Obstruction 2550 may be removed from suction device 2502 through obstruction clearing port 2540.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

Figure 27:
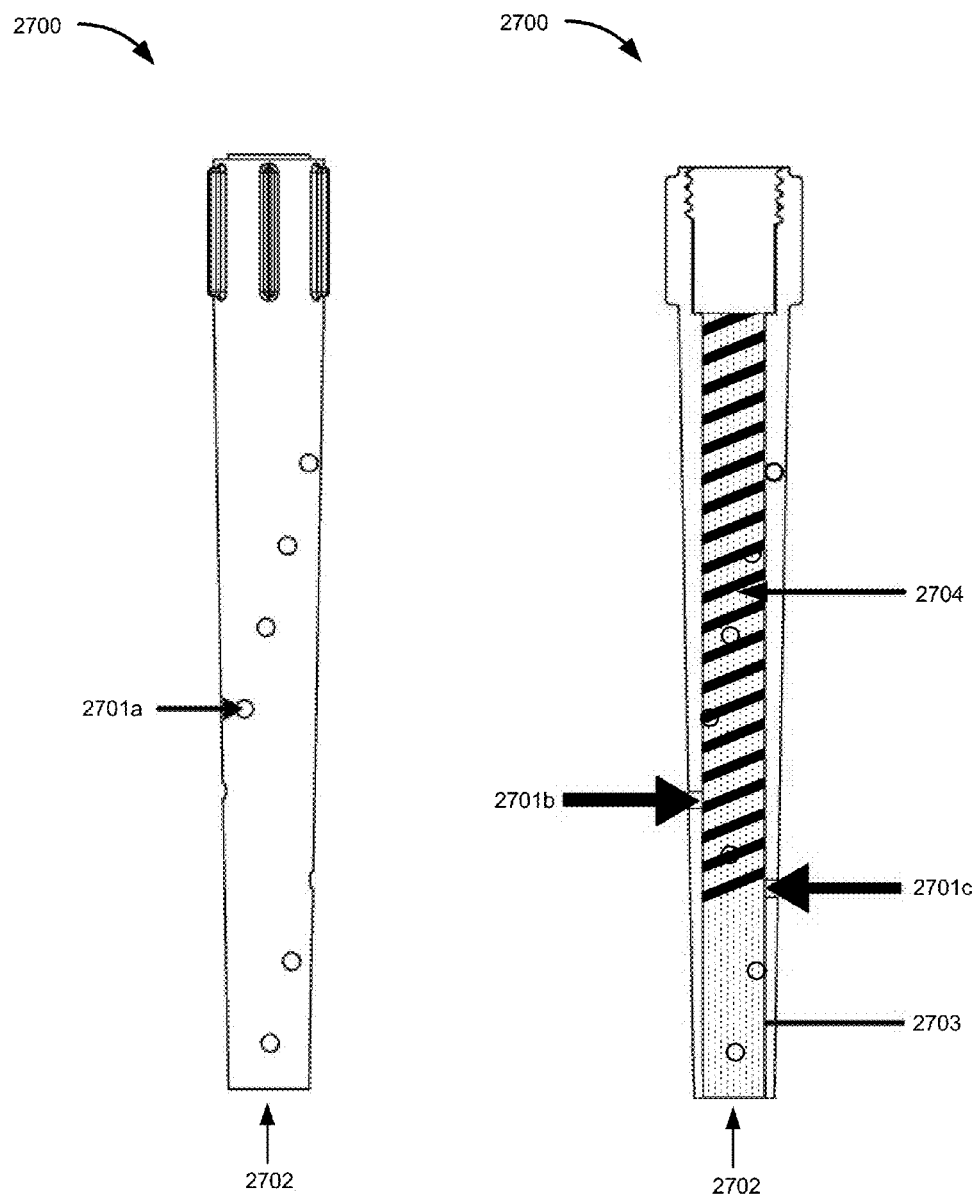
FIG. 27 illustrates an emulsion segment.
Figure 30:
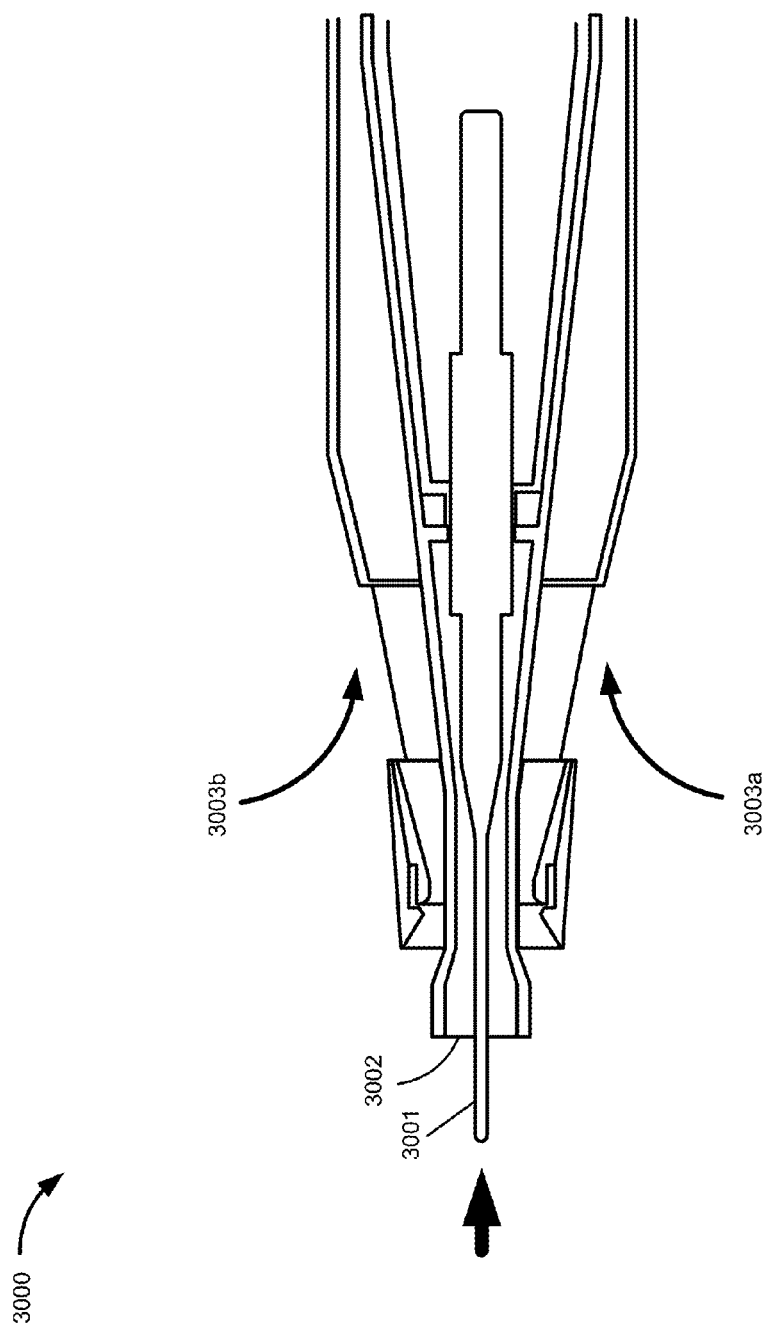
FIG. 30 illustrates a cross section of the device.

FIG. 27 illustrates an emulsion segment. The emulsion segment can be placed between the input port and the one or more intake ports disposed between the input port and the suction port. The emulsion segment can comprise an inner lumen and an outer lumen. The inner lumen can comprise one or more holes 2701*a-c* through which a least a portion of the flow of matter 2702 passes. The one or more holes 2701*a-c* can be evenly spaced along a length of the inner lumen. The one or more holes 2701*a-c* can be circumferentially spaced in series along a length of the inner lumen. The one or more holes 2701*a-c* can be toroidally spaced or helically spaced along the length of the inner lumen. As the at least a portion of the flow of matter 2702 passes through the one or more holes, a liquid portion 2703 of the flow of matter may be mixed with a gas portion of the flow of matter to create a froth or liquid-gas mixture 2704. The emulsion segment that froths the flow of matter 2702 a) may lighten the flow of matter, b) may prevent excessive suction at the input port to prevent suction adhesion to a solid surface, such as a tissue, c) may reduce or overcome suction adhesion at the input port, d) may aid is visualizing a surgical field and/or removing gas, such as smoke, or e) any combination thereof. FIG. 30 also illustrates a cross section of the device showing a surgical instrument 3001 that may be inserted into or integral thereto the device. The flow of matter may enter the input port 3002 or intake ports 3003*a-b* along the length of the device.

Figure 28:
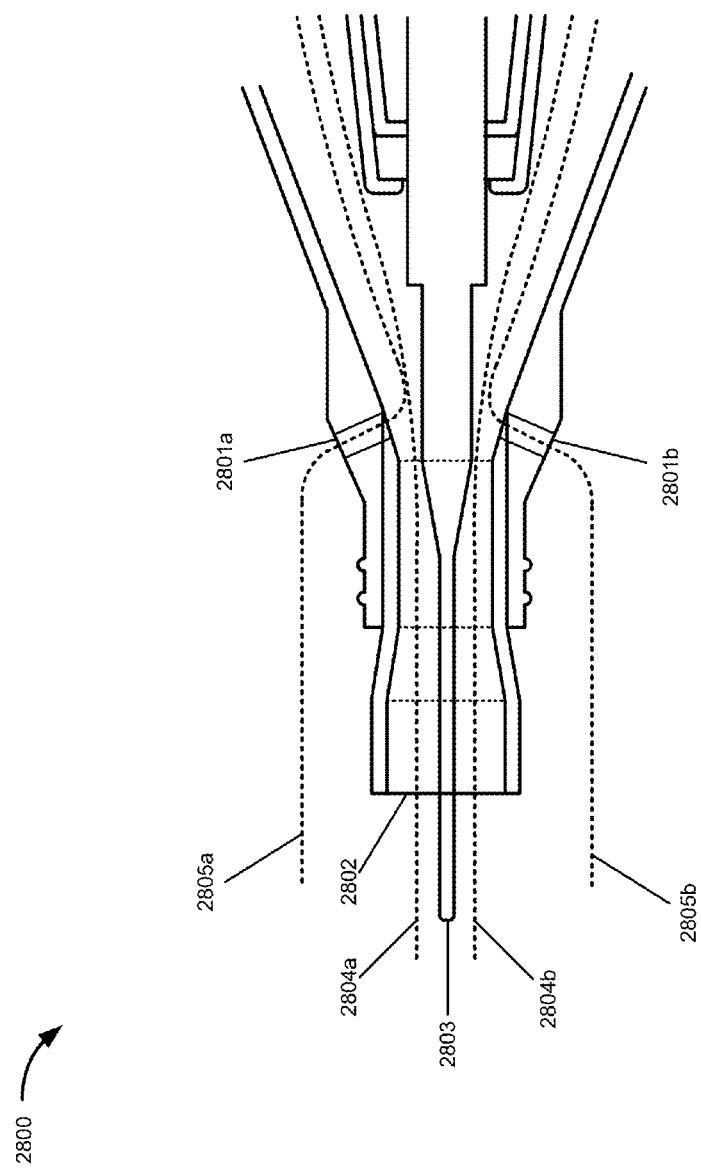
FIG. 28 illustrates a cross section of the device and flow paths through the device.

FIG. 28 illustrates a cross section of the device and flow paths of the flow of matter that may enter and pass through the device. A surgical instrument 2803 may be inserted in or integral thereto the suction device. A flow of matter 2804*a-b*, from for example a surgical field, may enter the suction device at an input port 2802 or may enter one or more intake ports on the input port (not shown). Additional flow of matter 2805*a-b*, from for example a surgical field, may enter the suction device at one or more intake ports 2801*a-b* on the suction device.

Figure 29:
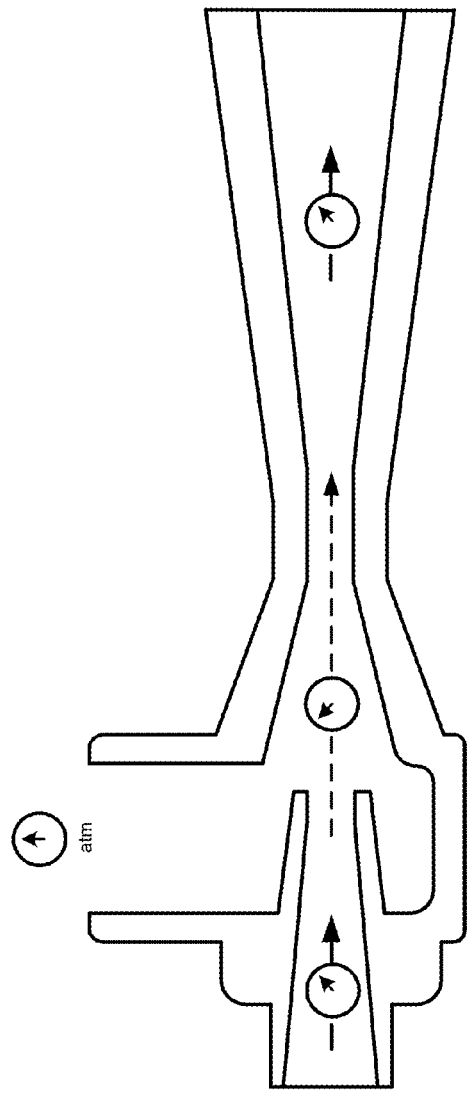
FIG. 29 illustrates the pressure differential generated in a lumen from a narrowing or a Venturi effect.
Figure 37:
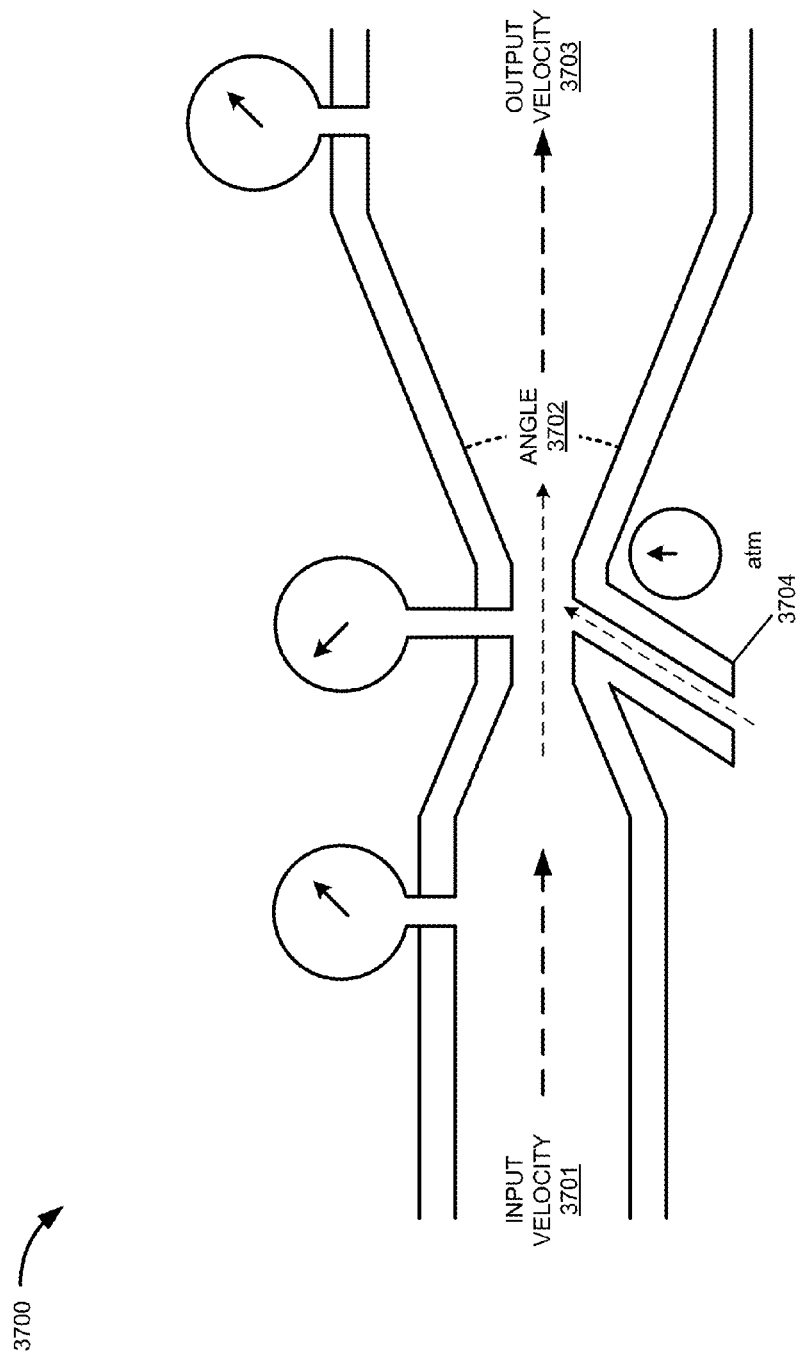
FIG. 37 illustrates the pressure differential generated in a lumen from a narrowing or a Venturi effect with an intake port placed at the narrowing.
Figure 38:
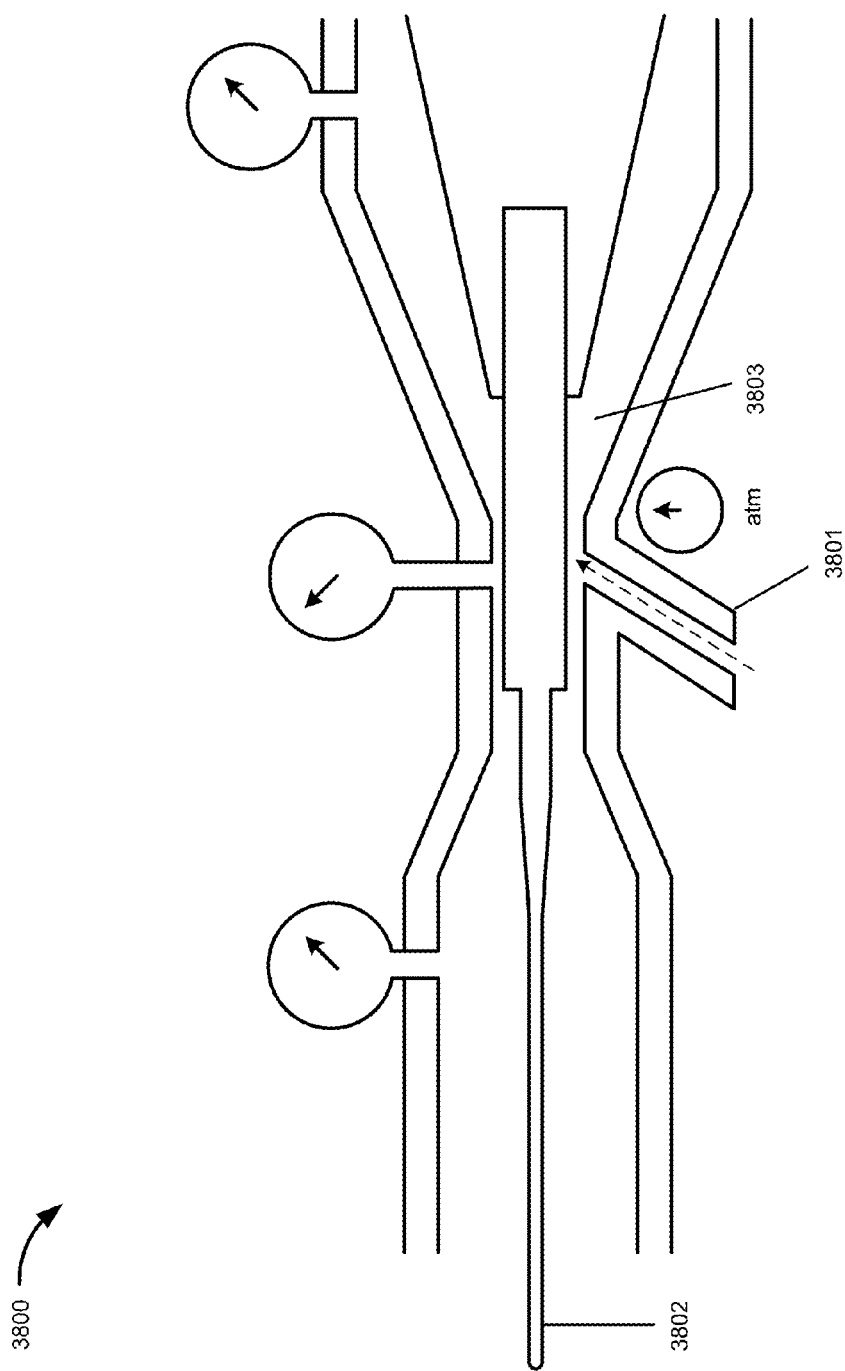
FIG. 38 illustrates the pressure differential generated in a lumen from a narrowing or a Venturi effect with an intake port placed at the narrowing.
Figure 39:
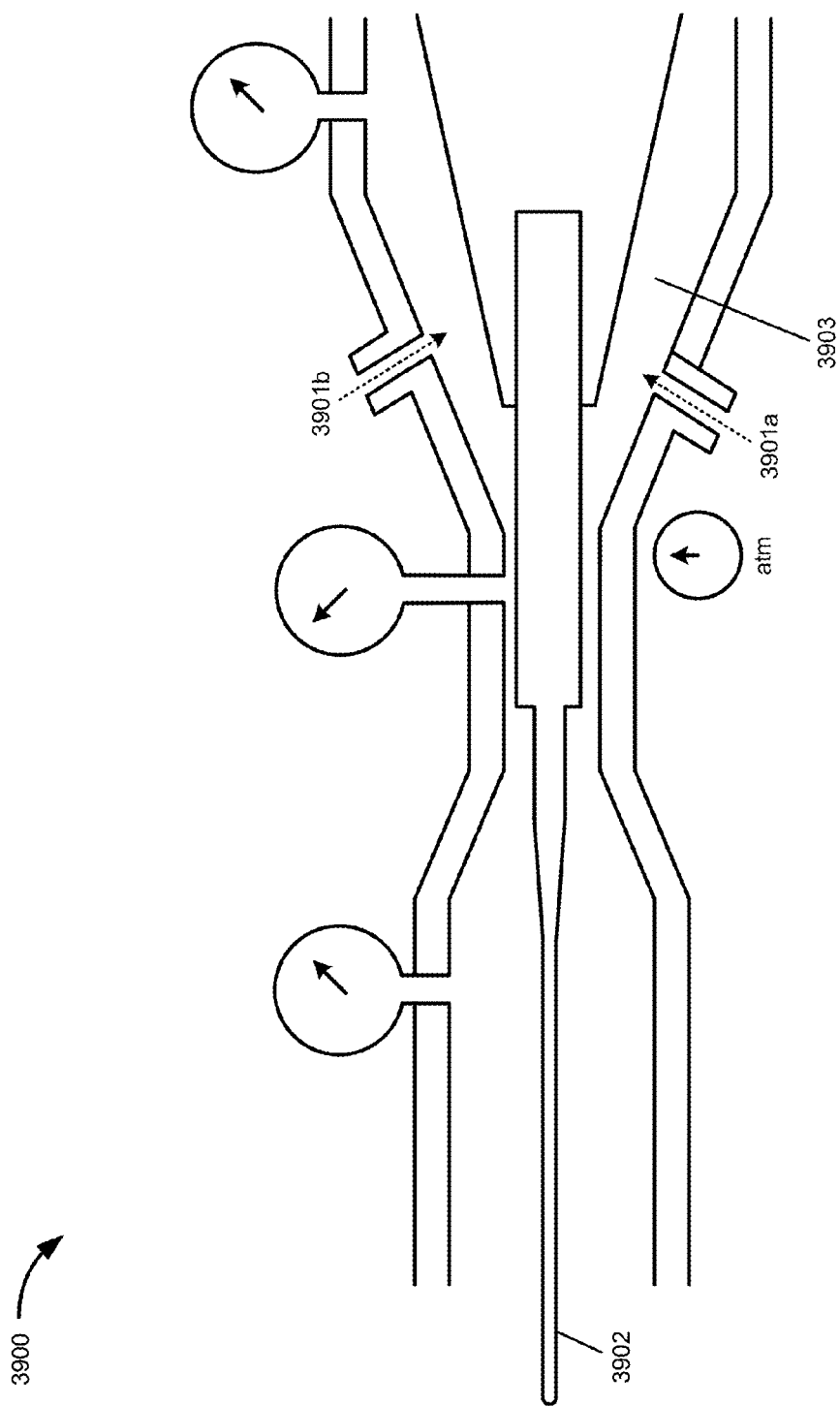
FIG. 39 illustrates the positioning of intake ports along a suction lumen of a device.
Figure 40:
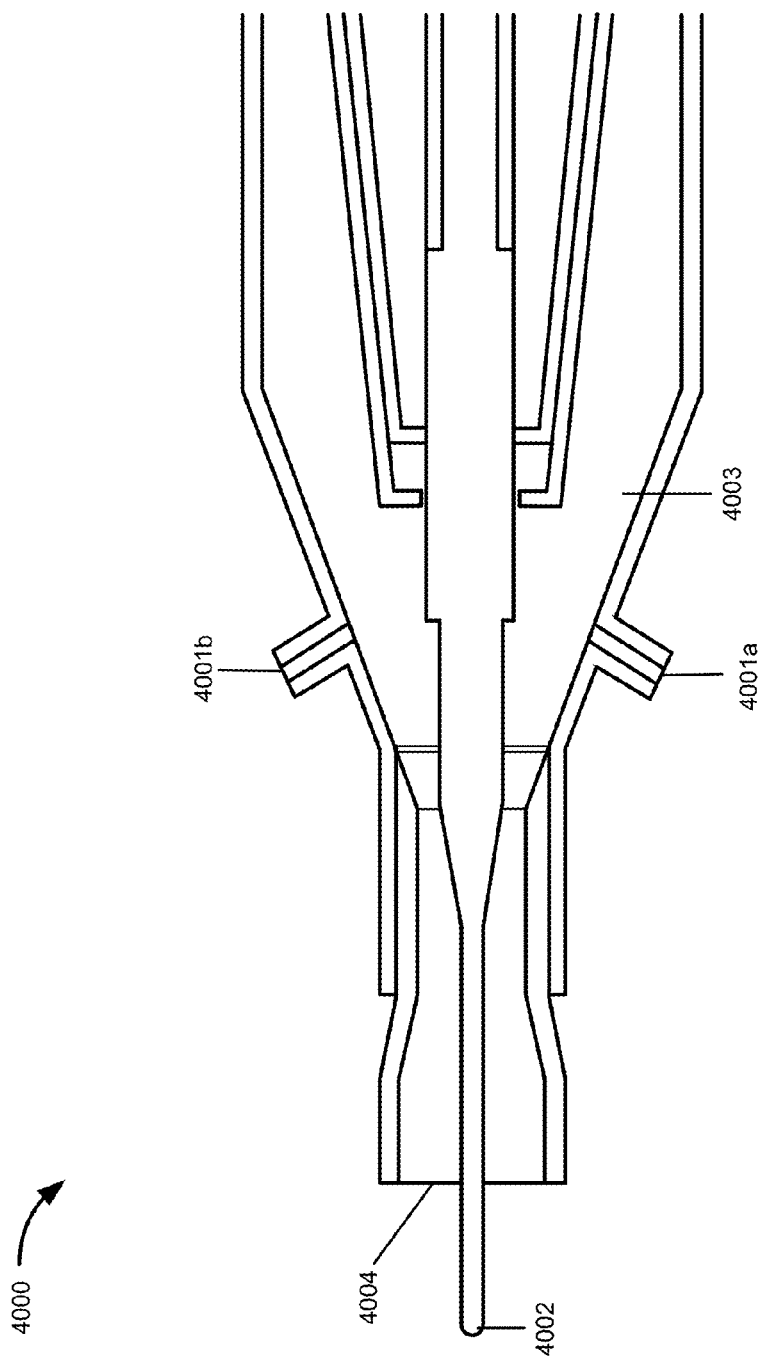
FIG. 40 illustrates the positioning of intake ports along a suction lumen of a device.
Figure 41:
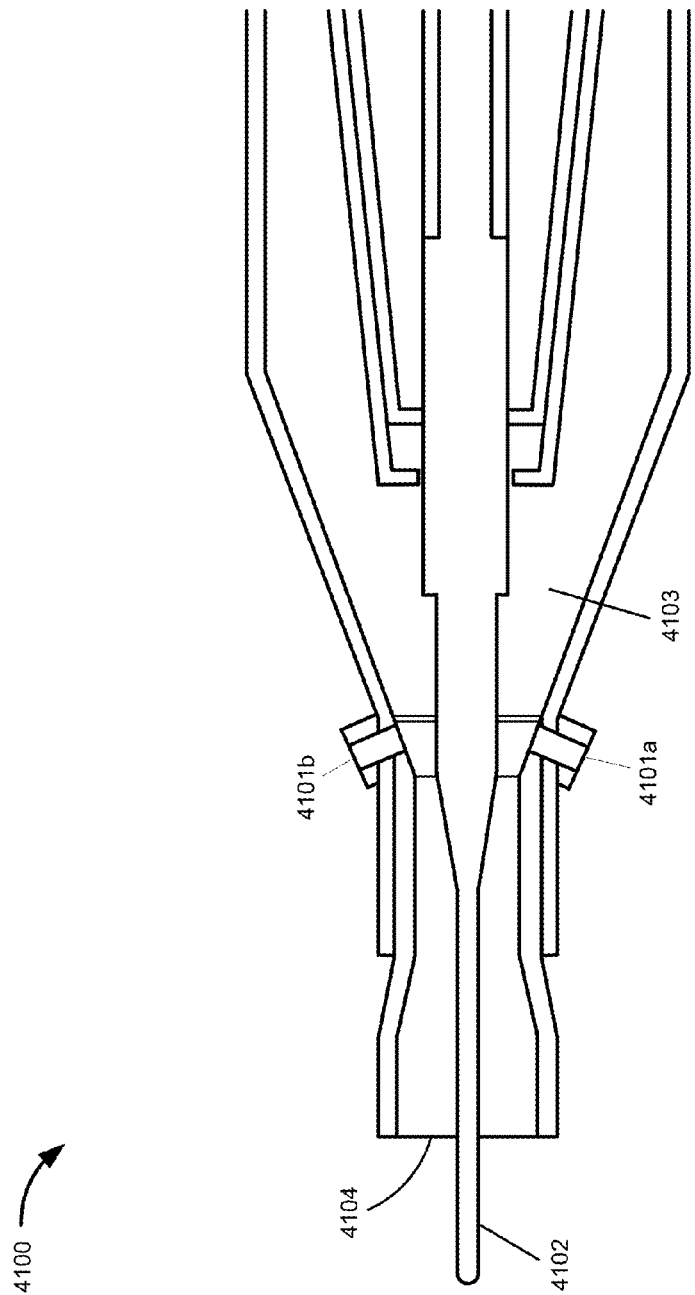
FIG. 41 illustrates the positioning of intake ports along a suction lumen of a device.

FIGS. 29 and 37 illustrate the pressure differential generated in a lumen from a narrowing or a Venturi effect. The pressure may be lower in the narrowing of the lumen compared with the higher pressure of the wider regions. This pressure differential may result from the flow of matter through the device. Fluid velocity may be greater and pressure lower in the narrowing of the lumen compared with the lower fluid velocity and higher pressure of the wider regions such as the input velocity 3701 and output velocity 3703. One or more intake ports 3704 may be positioned at the narrowing. The angle 3702 of the wider regions may be constant or adjustable to maximize the Venturi effect. The angle 3702 may be about 15 degrees. The angle 3702 may be from about 10 degrees to about 45 degrees. The angle 3702 may be about 5, 10, 15, 20, 25, 30, 35, 40, or 45 degrees.

Figures 31A, 31B:
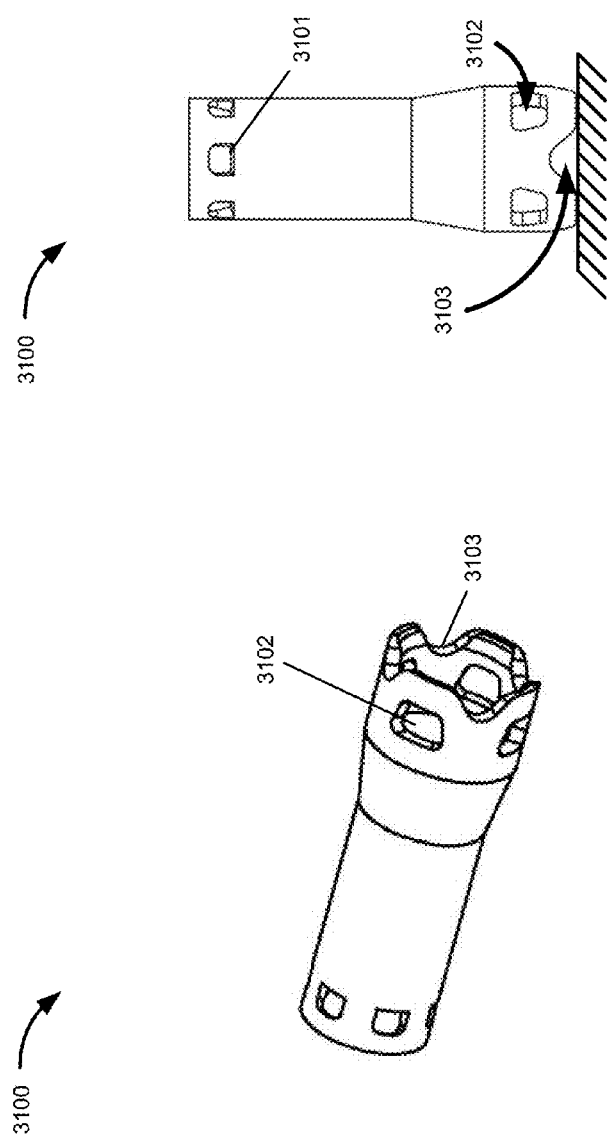
FIGS. 31A and 31B illustrate placement of intake ports and scalloped edging of the input port.

FIGS. 31A and 31B illustrate placement of intake ports 3101 and 3102 and scalloped edging 3103 of the input port. One or more intake ports 3102 may be placed on the input port. One or more intake ports 3101 may be between the input port and the suction port. The edge of the device may be modified to enhance capture of gas or liquid from the flow field or enhance the flow of matter. For example, the edge of the device may comprise one or more scalloped edgings 3103.

Figure 32A:
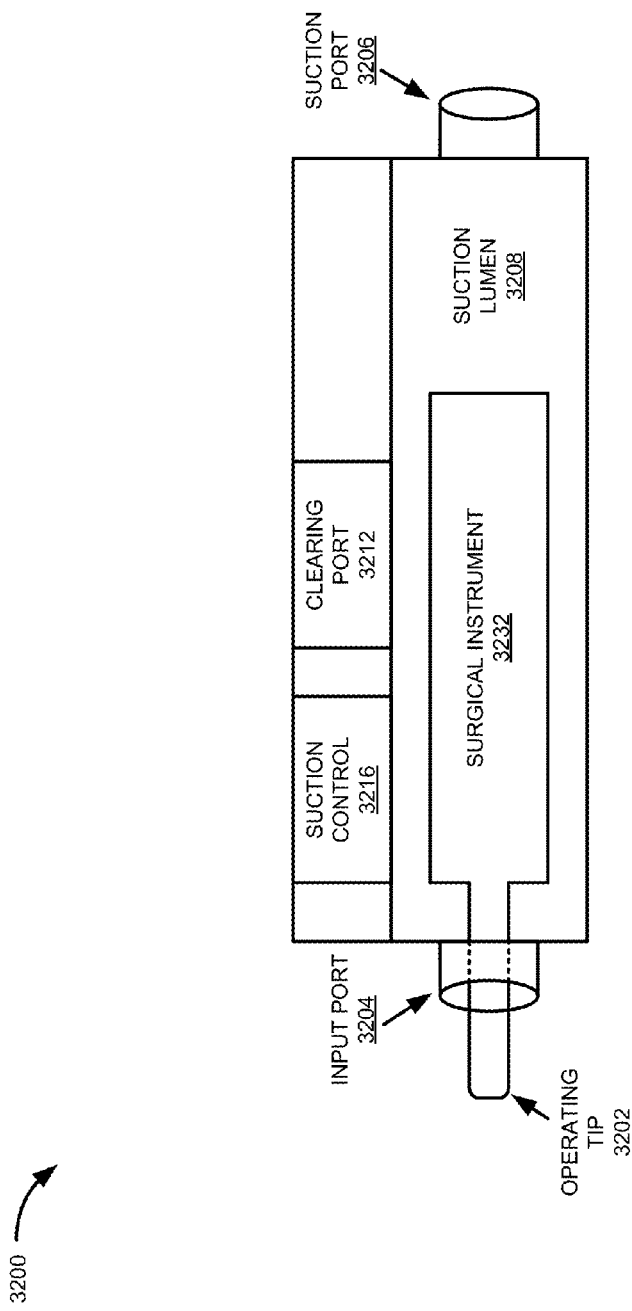
FIGS. 32A, 32B and 32C illustrate three separate flow diagrams showing the configuration of various components of the device.
Figure 32B:
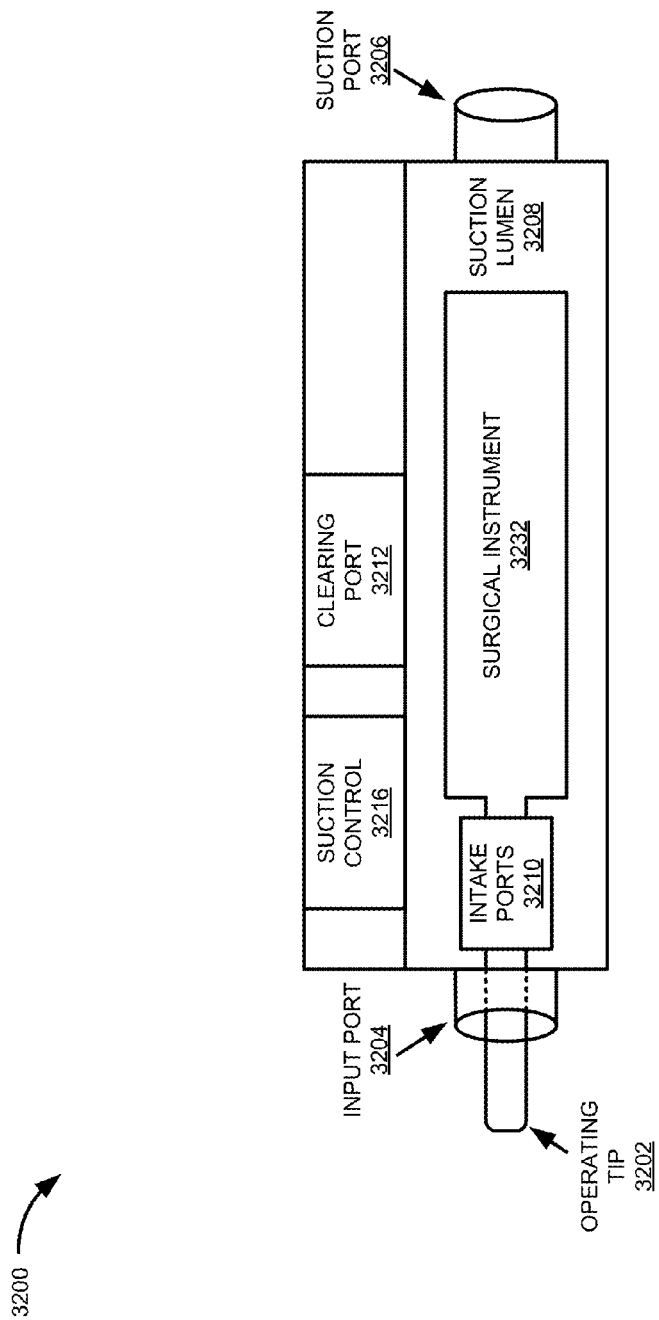
Figure 32C:
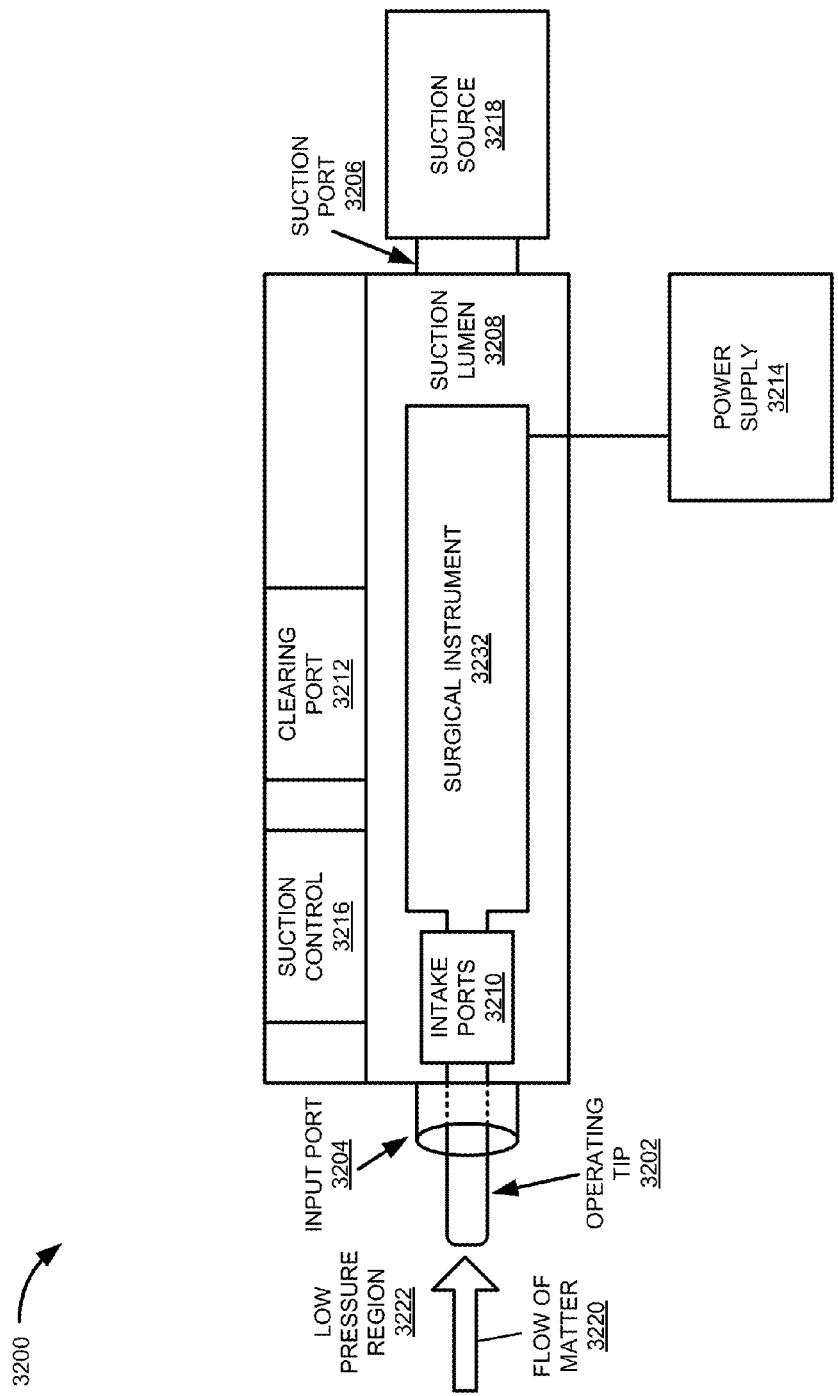

FIGS. 32A, 32B and 32C illustrate three separate flow diagrams showing the configuration of various components of the device. A surgical instrument 3232 with an operating tip 3202 may be inserted into or integral thereto the device 3200. Flow of matter 3220 from a low pressure region 3222 such as for example from a surgical field may enter a suction lumen 3208 from a) an input port 3204, b) one or more intake ports 3210 on an input port 3204, c) one or more intake ports 3210 between the input port 3204 and the suction port 3206, or d) any combination thereof. The device may further comprise a suction control 3216. The device may further comprise a clearing port 3212. The device may be operably connected to a suction source 3218. The device may be operably connected to a power supply 3214.

Figure 33:
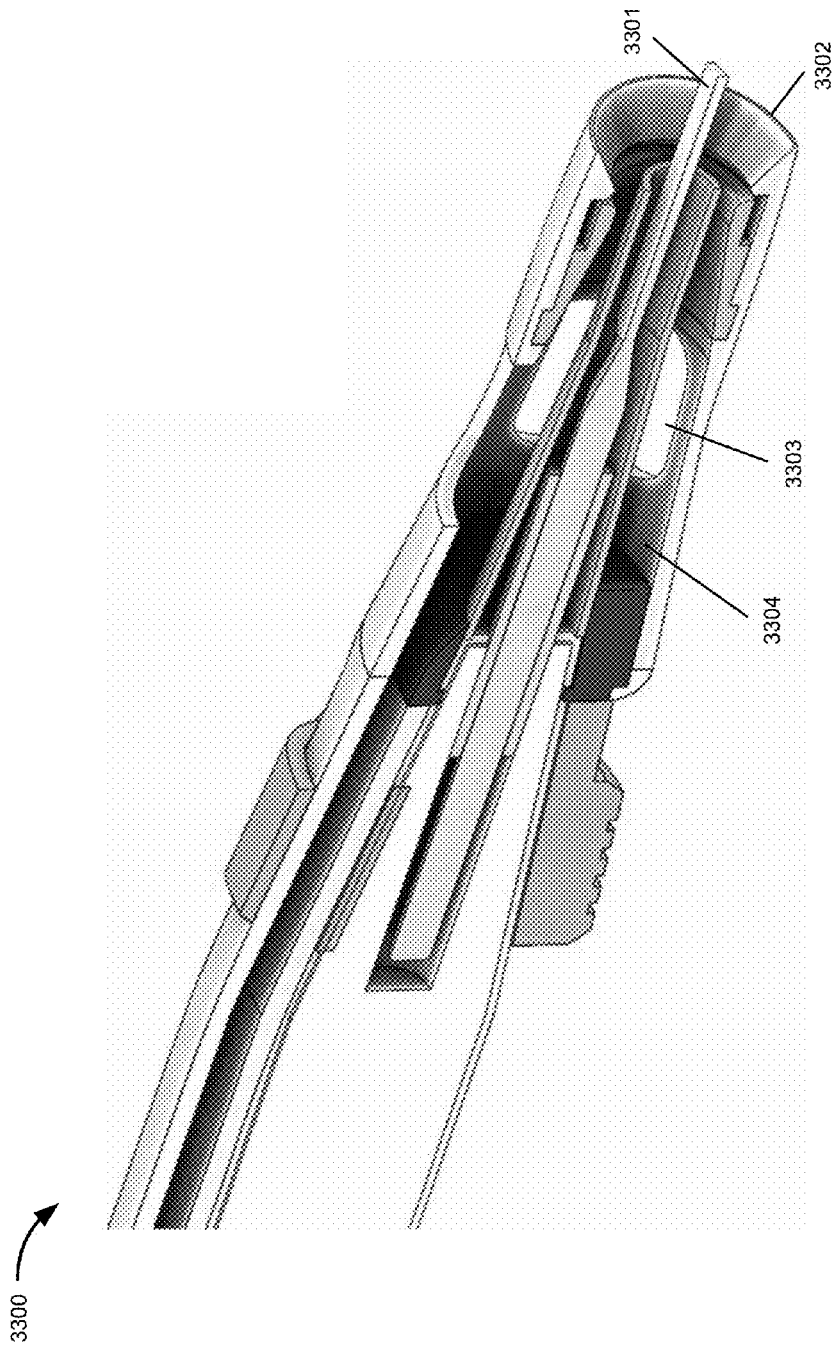
FIG. 33 illustrates a cross section of the device.
Figures 34A, 34B:
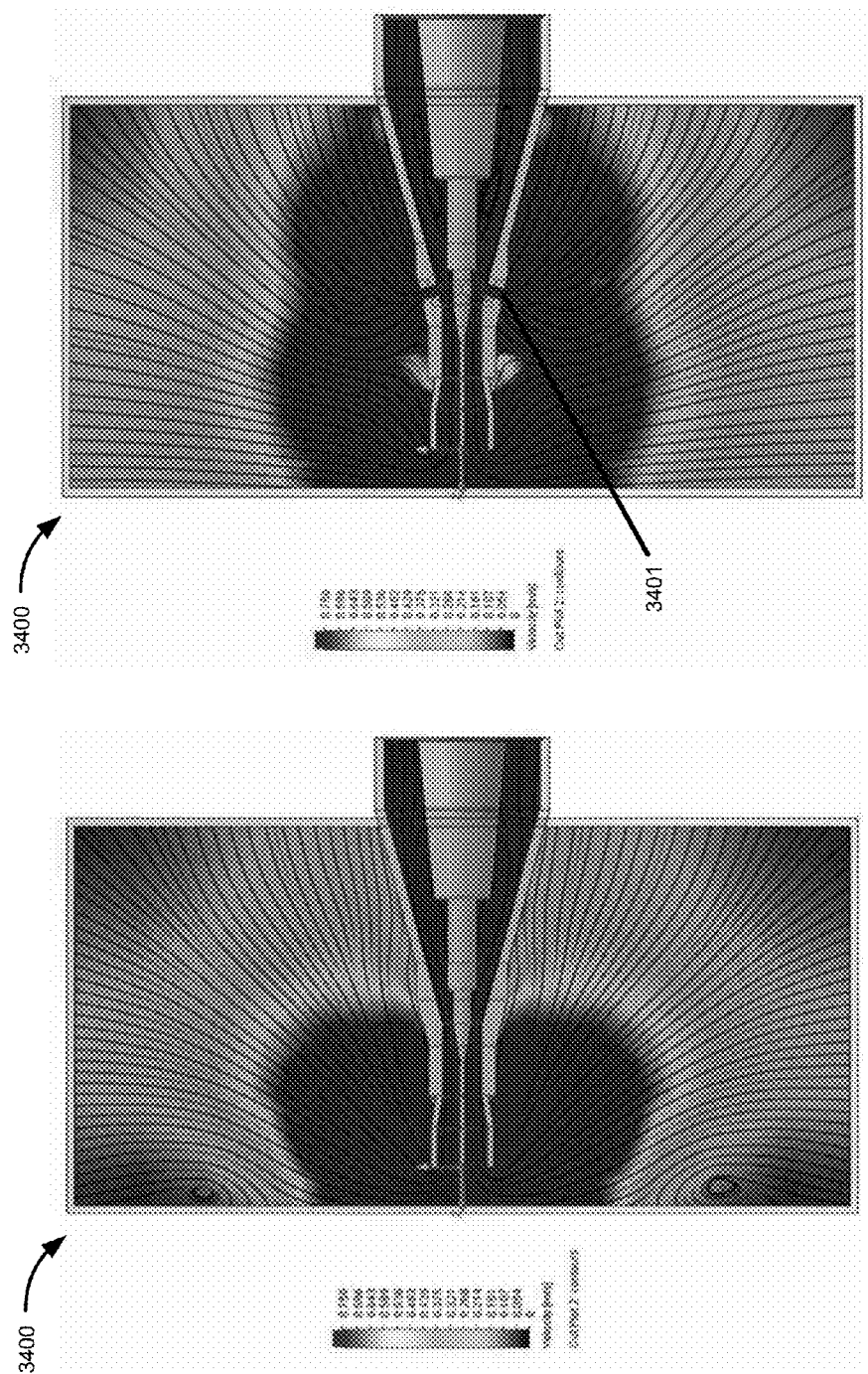
FIGS. 34A and 34B illustrate computational fluid dynamic (CFD) plots of flow fields surrounding a device without intake ports, 34A, and with intake ports, 34B.
Figure 35:
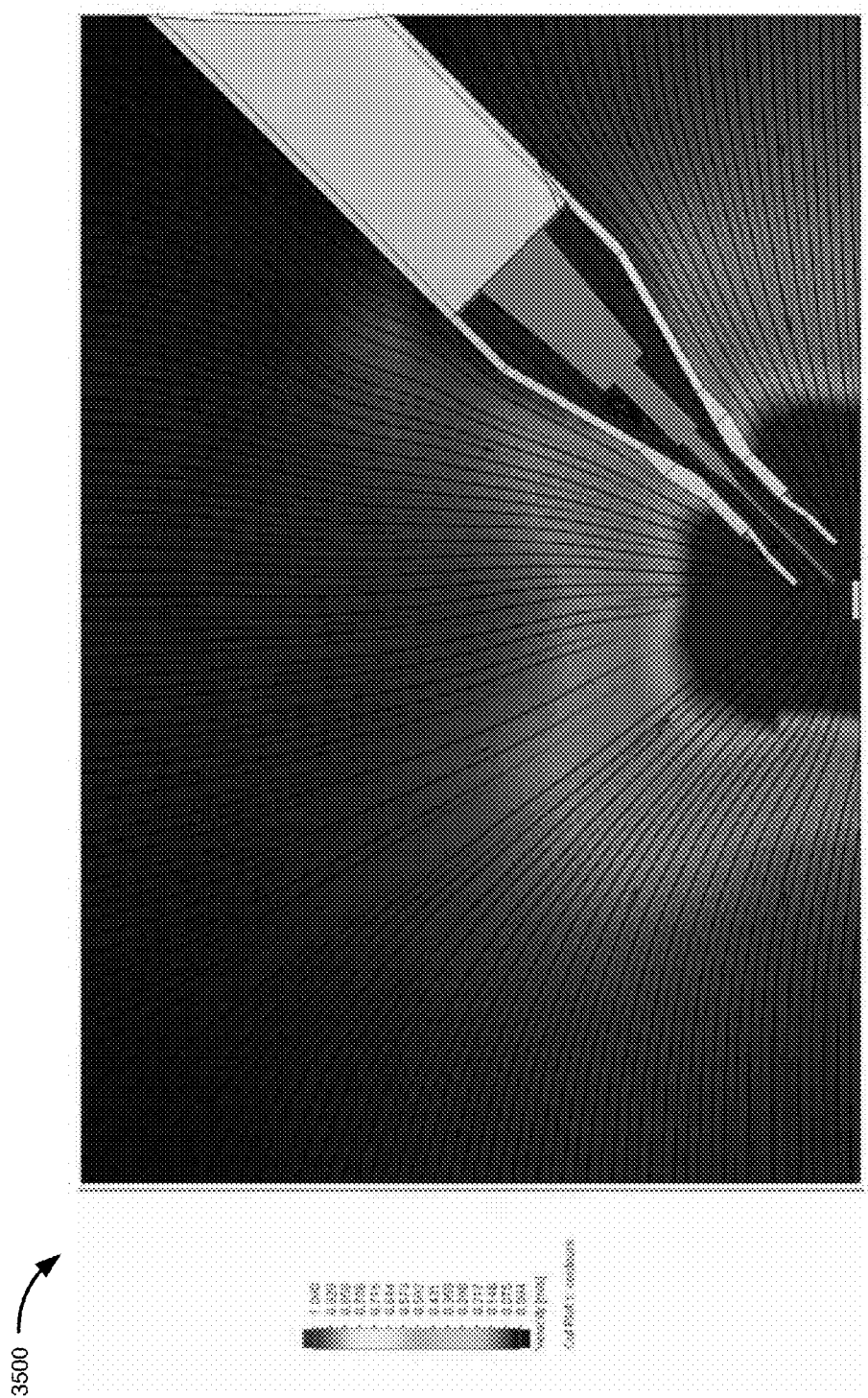
FIG. 35 illustrates a CFD plot of flow fields surrounding a device without intake ports.
Figure 36:
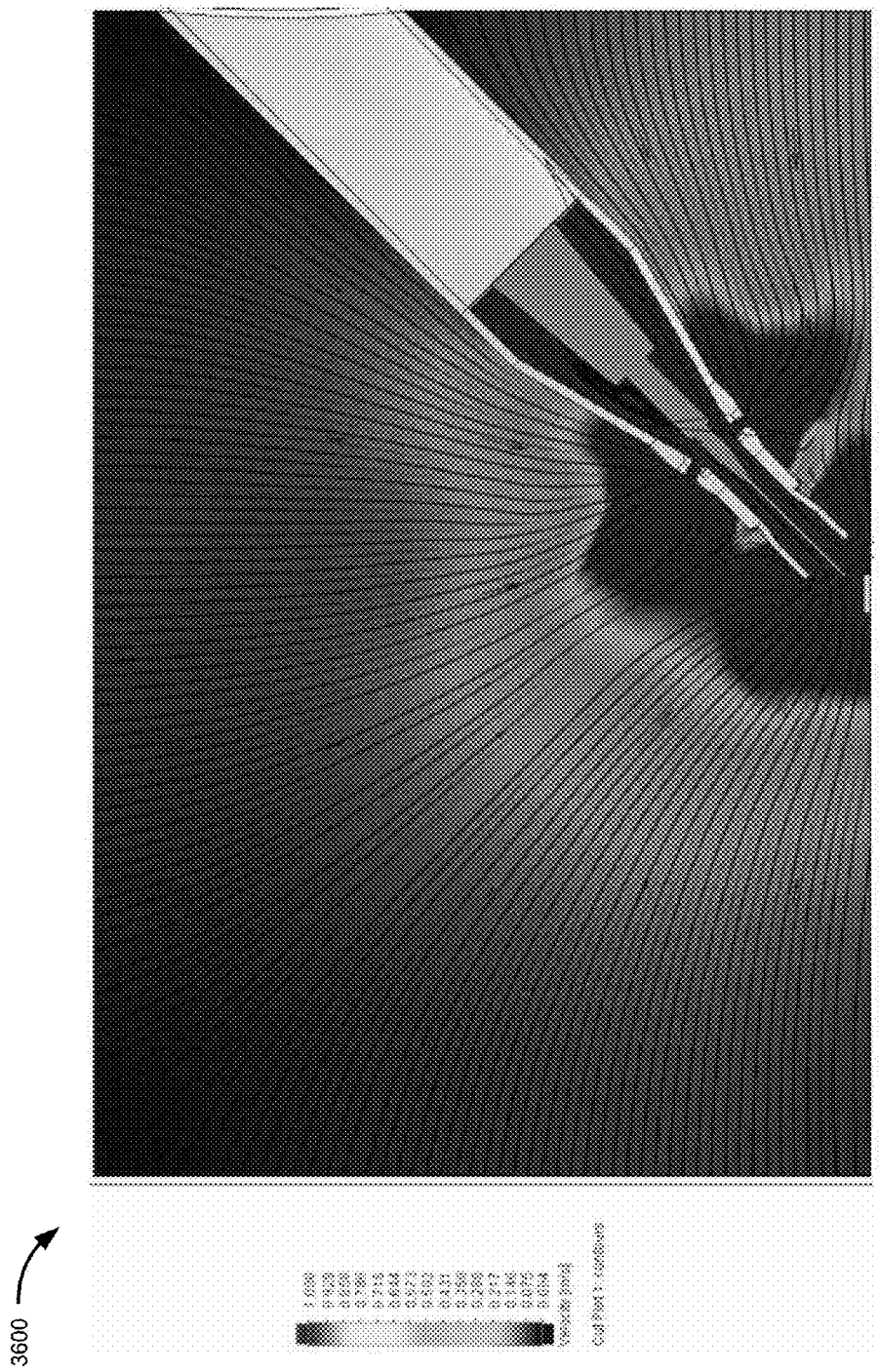
FIG. 36 illustrates a CFD plot of flow fields surrounding a device with intake ports.

FIG. 33 illustrates a cross section of the device 3300. A surgical instrument 3301 may be inserted into or integral thereto the device 3300. A flow of matter may enter a suction lumen 3304 from a) an input port 3302, b) one or more intake ports 3303.

FIGS. 34A, 34B, 35, and 36 illustrate computational fluid dynamic (CFD) plots of flow fields surrounding a device without intake ports, 34A and 35, and with intake ports 3401, 34B and 36. The area of suction surrounding the device may increase by at least 2 fold with one or more intake ports 34B and 36 compared to a device without intake ports 34A and 35. The area of suction surrounding the device may increase by at least 1 fold, 1.5 fold, 2 fold, 2.5 fold, 3 fold, 3.5 fold, 4 fold, 4.5 fold, 5 fold, 10 fold or more compared to a device without intake ports. The area of suction surrounding the device may increase by at least 1 fold or more compared to a device without intake ports. The area of suction surrounding the device may increase by at least 2 fold or more compared to a device without intake ports. The area of suction surrounding the device may increase by at least 3 fold or more compared to a device without intake ports. The area of suction surrounding the device may increase by at least 4 fold or more compared to a device without intake ports.

FIGS. 38, 39, 40, and 41 show a cross section of the device (3800, 3900, 4000, 4100) illustrating the positioning of one or more intake ports (3801, 3901a-b, 4001a-b, 4101a-b) after the input port (4004, 4104) and positioned along a suction lumen (3803, 3903, 4003, 4103) formed between the device and the surgical instrument (3802, 3902, 4002, 4102).

The input port may comprise a scallop shape. The one or more intake ports may comprise a scallop shape. The scallop shape may be a double scallop, a triple scallop, a quadruple scallop, or more. The scallop shape may increase capture or collection of gas and liquid from a surgical field at the input port compared to other shapes, such as a blunt end input port. The scallop shape may alter the flow profile within the suction lumen, such as improving laminar flow or enhancing suction capacity at the input port.

The one or more intake ports may be disposed on the input port, disposed between the input port and the suction port, or a combination thereof. The one or more intake ports may be two, three, four, five, or more. The one or more intake ports on the input port may be three. The one or more intake ports on the input port may be four. The one or more intake ports on the input port may be five. The one or more intake ports between the input port and the suction port may be one. The one or more intake ports between the input port and the suction port may be two. The one or more intake ports between the input port and the suction port may be three. The one or more intake ports between the input port and the suction port may be four. The one or more intake ports between the input port and the suction port may be five.

Adding one or more intake ports to the device may enhance capture and suction of materials from a surgical field, may improve visibility of the surgical field, may reduce user exposure to toxic or harmful components within the surgical field, or any combination thereof. Adding one or more intake ports to the device may enhance the suction capacity of the device. For example, the suction capacity may increase at least about 1 fold, 1.5 fold, 2 fold, 2.5 fold, 3 fold, 3.5 fold, 4 fold, 4.5 fold, 5 fold, 10 fold or more compared to a suction device without intake ports. The suction capacity may increase at least about 2 fold compared to a suction device without intake ports. The suction capacity may increase at least about 3 fold compared to a suction device without intake ports. The suction capacity may increase at least about 1.5 fold compared to a suction device without intake ports.

The suction area may increase in a suction device with intake ports compared to a suction device without. For example, the suction area may increase at least about 1 fold, 1.5 fold, 2 fold, 2.5 fold, 3 fold, 3.5 fold, 4 fold, 4.5 fold, 5 fold, 10 fold or more compared to a suction device without intake ports. The suction area may increase at least about 2 fold compared to a suction device without intake ports. The suction area may increase at least about 1.5 fold compared to a suction device without intake ports.

The shape or geometry of the suction lumen may be adjusted to alter the flow profile of the flow of matter travelling through the suction lumen. The shape or geometry may be adjusted to enhance laminar flow. The shape or geometry may be adjusted to enhance the suction capacity of the device. The shape or geometry may be adjusted to enhance capture of the flow of matter from the surgical field. In some embodiments, the shape may be one or more edges of one or more intake ports in fluidic communication with the suction lumen. The one or more edges may form an angle of less than 90 degrees relative to the body of the device. One or more edges may form an angle of less than about 85, 80, 75, 70, 65, 60, 55, 50, 45, 40, 35, 30, 25, 20, 15, or about 10 degrees. One or more edges may form an angle from about 60 to 80 degrees. One or more edges may form an angle from about 35 to about 55 degrees.

The one or more intake ports may enhance suction at an input port of the suction device. The one or more intake ports may be positioned on the input port. The one or more intake ports may be positioned between the input port and the suction port. The suction lumen, connecting the input port and the suction port and in fluidic communication with the one or more intake ports, may have one or more narrowings, such as a reduction in diameter of the suction lumen. At the narrowing of the suction lumen the pressure may decrease and the flow rate of the flow of matter passing through the suction lumen may increase. The one or more intake ports may be positioned at the region of highest flow rate immediately following the narrowing. The one or more intake ports may be positioned at the narrowing. The one or more intake ports may be positioned circumferentially in series about the narrowing. The one or more intake ports may be positioned at a narrowest point of the narrowing in the suction lumen.

One of more intake ports may be fluidically connected to the suction lumen and positioned circumferentially about the device. The one or more intake ports may be positioned in series along one side of the device. The one or more intake ports may be positioned toroidally or helically along a portion of the length of the device. The one or more intake ports may be positioned randomly along a portion of the length of the device. The one or more intake ports may be clustered together on a portion of the device. One or more intake ports may have the same diameter opening at the input port. One or more intake ports may have a diameter opening about ¾, ½, ⅓, ¼, ⅕, ⅙, ⅐, ⅛, 1/16 or less the diameter of the input port. One or more intake ports may have a diameter opening about ¾ or less the diameter of the input port. One or more intake ports may have a diameter opening about ½ or less the diameter of the input port. One or more intake ports may have a diameter opening about ¼ or less the diameter of the input port. One or more filters may be attachable to or integral thereto the device. The one or more filters may cover a portion or substantially cover the entire area of one or more intake ports. The one or more filters may prevent solids from the surgical field from entering the suction lumen via the one or more intake ports. The one or more filters may comprise a pore size of about 100 micrometers or less. The one or more filters may comprise a pore size of about 500 micrometers or less. The one or more filters may comprise a pore size of about 200 micrometers or less. The one or more filters may comprise a pore size of about 75 micrometers or less. The one or more filters may comprise a pore size of about 50 micrometers or less.

The suction device may comprise an emulsion segment. The emulsion segment may be positioned between the input port and the suction port. The emulsion segment may be positioned between the input port and the one or more intake ports disposed between the input port and the suction port. The emulsion segment may comprise an inner lumen and an outer lumen. The inner lumen may comprise one or more holes. As the flow of matter enters the device via the input port, the suction may draw at least a portion of the flow of matter through the one or more holes of the emulsion segment to generate a froth or liquid gas emulsion. The one or more holes may be spaced toroidally or helically along the length of the inner lumen.

The suction device may comprise a body that is configured to attach to an instrument, such as a surgical instrument. The suction device may comprise a body that that integral thereto or formed thereon an instrument, such as a surgical instrument. The body may comprise an input port, a suction port, and a suction lumen disposed within the body that couples the input port to the suction port. The input port may be disposed towards the distal end of the body. The input port may be configured to receive a flow of matter. The input port may have a blunt edge. The input port may have an edge configured to enhance capture of the flow of matter from a field, such as a surgical field. The input port may have a scalloped edge, a double scalloped edge, or multi-scalloped edge. The input port may comprise one or more intake ports. The suction port may be disposed towards a proximal end of the body. The suction port may be configured to couple to a suction source, such as a suction source generated by a Coanda effect or a positive pressure operated fluid accelerator. The suction device may comprise one or more intake ports in fluid communication with the suction lumen. The one or more intake ports may be positioned on the input port, may be positioned between the input port and the suction port, or a combination thereof.

The suction device, attachable to a surgical instrument, may further comprise an instrument retainer. The instrument retainer may be configured to couple the surgical instrument to the body of the suction device. The suction device may further comprise a gasket. The gasket may be disposed within the body and configured to provide a seal between the suction device and the surgical instrument. The gasket may comprise one or more flexible membranes. The flexible membrane may permit removal of an obstruction from the suction device. A user may detach the surgical instrument to remove an obstruction from the suction device.

The suction device may further comprise a suction control. The suction control may be configured to be adjustable by a user. The suction control may be configured to be automatically adjustable. The suction control may be configured to be adjustable from a remote location, such as from a computer. The suction control may adjust the suction capacity at the input port of the suction device. The suction control may adjust a rate of gas evacuation, a rate of liquid evacuation, or a combination thereof from a field, such as a surgical field. The suction control may be adjusted such that a gas is evacuated from a field, a liquid is evacuated from a field, or a combination thereof. The suction control may be adjusted by a user or automatically adjusted based on an action taken by the device. For example, when the surgical instrument is set to an operation mode to cauterize a vessel, the suction control may be adjusted by a user or automatically adjusted to suction or remove a gas from the surgical field. When the surgical instrument is set to an operation mode to cut a tissue, the suction control may be adjusted by a user or automatically adjusted to suction a gas and a liquid from the surgical field. When the suction capacity of the suction device may cause excessive suction attachment to a tissue surface in the surgical field, the suction control may be reduced by a user or automatically adjusted.

The suction control may be adjusted by any number of mechanical adjustments on the device. For example, the suction device may comprise a sliding member configured to be adjustable. The sliding member may adjust a gas evacuation, a liquid evacuation, or a combination thereof at the input port. The sliding member may partially close or completely close one or more intake ports to reduce or stop the flow of matter from entering the one or more intake ports. The sliding member may comprise a linear sliding mechanical element, a circumferential sliding mechanical element, or a combination thereof.

The suction control may comprise one or more detents. The one or more detents may be configured to locate the suction control in user or automatically controlled positions, using for example friction. Detents may comprise one or more teeth grippers, continuous or discrete notches, or any combination there.

The suction device may comprise one or more nozzles. The one or more nozzles may be attachable to the suction device or integral thereto. The one or more nozzles may be positioned on or adjacent the input port. The one or more nozzles may comprise one or more intake ports. The one or more nozzles may comprise a blunt edge, scallop edge, double scallop edge, or other geometric shaped edge.

The one or more intake ports may be positioned on one or more nozzles, on the input port, or between the input port and the suction port. The one or more intake ports may be in fluidic communication with the suction lumen. The one or more intake ports may comprise a blunt edge, scallop edge, double scallop edge or more. A shape of the one or more intake ports may be configured to enhance capture or suction of the flow of matter from a surgical field. A shape of the one or more intake ports may be configured to enhance laminar flow within the suction lumen. A shape of the suction lumen may be configured to enhance laminar flow within the suction lumen. At a point in which an intake port fluidically connects to the interior surface of the suction lumen, the shape of this point may be configured to optimally capture or suction the flow of matter from the surgical field and/or enhance laminar flow within the suction lumen. The shape may be smooth or curved. The shape may be configured to reduce sharp or blunt edges. The shape may be an edge of the one or more intake ports in fluidic communication with the suction lumen, the edge of which forms an angle of less than 90 degrees relative to the body of the suction device. Shaping the one or more intake ports may include shaping all edges that fluidically connect to the suction lumen. Positioning of the instrument, such as a surgical instrument, may also enhance capture or suction of the flow of matter from a surgical field or enhance laminar flow within the suction lumen. For example, positioning a smooth surface of the surgical instrument directly opposed to the intake port may enhance laminar flow within the suction lumen, compared with an angled edge of the instrument.

The suction device may comprise one or more filters. The filters may be attachable to an exterior surface of the suction device, integral to an interior portion of the suction device, or a combination thereof. A filter may be positioned on an exterior surface of the suction device adjacent to one or more intake ports. A filter may partially or completely cover the one or more intake ports. The filter may prevent solids from a surgical field from entering the suction device via the one or more intake ports and preventing an obstruction within the suction lumen. The filter may comprise a pore size of about 500, 200, 150, 100, 75, 50 micrometers or less.

The one or more intake ports may be 1, 2, 3, 4, 5, 6, 7, 8, 9, 10 ports or more. The one or more intake ports may be 3 ports. The one or more intake ports may be 4 ports. The one or more intake ports may be 5 ports. The one or more intake ports may be 6 ports. The one or more intake ports may be 7 ports. The one or more intake ports may be 8 ports. Changing the number of intake ports may alter a suction capacity, a suction area, a gas to liquid suction ratio, alter a suction adhesion or any combination thereof. Opening or closing a number of intake ports may alter the number of active intake ports and thus alter a suction capacity, a suction area, a gas to liquid suction ratio, a suction adhesion or any combination thereof. Opening one or more intake ports or adding additional ports on the input port may reduce suction adhesion. Opening one or more intake ports or adding additional ports disposed between the input port and the suction port may reduce suction adhesion.

The suction device may operate in a liquid mode, ideal for suctioning liquid. The suction device may operate in gas-liquid mode, ideal for suctioning both gas and liquid. The suction device may be adjusted between the liquid mode and the gas-liquid mode, for example, by a user manipulating a sliding member or switch. The suction device may be adjusted between the liquid mode and the gas-liquid mode is a binary way (on-off switch) or in a graded way (tuner dial). The suction device may operate in a liquid mode when for example intake ports are closed or partially closed. The suction device may operate in a gas-liquid mode when for example intake ports are open or partially open.

The intake ports disposed between the input port and the suction port may be positioned at a narrowing of the suction lumen to maximize suction capacity. The intake ports disposed between the input port and the suction port may be positioned at a widening of the suction lumen to decrease suction capacity. The suction device may be configured with a porous scaffold surrounding the surgical instrument the inner volume between which forms the suction lumen. A two-part sheath may be disposed circumferentially about the porous scaffold. The porous scaffold may minimize the thickness and number of connecting segments of the scaffold and may maximize the open surface area of the scaffold. The two-part sheath fitted adjacent to and circumferentially surrounding the scaffold, may form a gap space between the two parts of the sheath, such as an annular opening. The gap space between the two parts of the sheath may be in fluidic communication with the suction lumen to accept flow of matter from a surgical field similar to the intake ports as described elsewhere. Such a design configuration may permit for tuning the suction device across a range of suction capacities by tuning the positioning of the intake ports. Moving the gap space adjacent to a narrowing of the suction lumen may increase suction capacity, increase suction area, and permit gas-liquid suction. Moving the gap space away from a narrowing of the suction lumen may decrease suction capacity, decrease suction area, and permit predominantly liquid suction.

Maximizing an open surface area at a narrowing of the suction lumen may maximize the suction capacity of the suction device. Maximizing the number of intake ports may maximize the surface area. Maximizing the open surface area of the individual intake ports may maximize the suction capacity of the suction device. A suction device may comprise a two-part sheath surrounding the surgical instrument the inner volume between which forms the suction lumen. One or each of the sheath parts of the two-part sheath may comprise one or more sets of radial ribs or fan blades disposed circumferentially about an interior surface of the sheath and contacting the surgical instrument to mechanically anchor that portion of the sheath to the surgical instrument. A suction device with a two-part sheath may comprise a gap space, such as an annular opening. The gap space between the two parts of the two-part sheath may be in fluidic communication with the suction lumen to accept flow of matter from a surgical field similar to the intake ports as described elsewhere. Such as design configuration may permit for maximizing the open surface area at a narrowing of the suction lumen to maximize a suction capacity of the suction device.

What is claimed is:

1. A method comprising
   directing a suction flow through an input port of a body configured to couple with an electrosurgical instrument, wherein the body comprises a distal end and a proximal end and a narrow segment positioned between the distal end and the proximal end, wherein the input port is positioned at the distal end, wherein one or more intake ports are positioned at the distal end, and wherein the one or more intake ports are positioned so that they are in flud communication with the narrow segment;
   directing the suction flow through the narrow segment so that a velocity of the suction flow is increased as the suction flow passes through the narrow segment; and
   directing a flow of matter through the one or more intake ports, wherein a velocity of the flow of matter through the one or more intake ports is increased by a Venturi effect that is generated when the suction flow passes through the narrow segment, wherein the body comprises an emulsion segment positioned to receive the flow of matter.

2. The method of claim 1, wherein the increase in the velocity of the flow of matter as the matter passes through the narrow segment causes an increase in the velocity of the suction flow through the input port.

3. The method of claim 1, wherein the body has a central horizontal axis.

4. The method of claim 3, wherein the narrow segment comprises an angle of 15 degrees or less relative to the central horizontal axis.

5. The method of claim 1, wherein the width of the narrow segment is adjustable.

6. The method of claim 4, wherein the angle is adjustable.

7. The method of claim 1, wherein the body comprises a longitudinal channel.

8. The method of claim 7, wherein the longitudinal channel comprises a flexible membrane configured to facilitate removal of an obstruction in the longitudinal channel.

9. The method of claim 8, wherein the body comprises an opening along at least a portion of the longitudinal channel that abuts the electrosurgical instrument when the body is coupled with the electrosurgical instrument so that a portion of the electrosurgical instrument covers the opening when the body is coupled with the electrosurgical instrument.

10. The method of claim 9, comprising a gasket configured to tightly couple the electrosurgical surgical instrument with the body so that the opening is tightly sealed when covered by the electrosurgical instrument.

11. The method of claim 10, comprising decoupling the electrosurgical instrument from the body and removing an obstruction from the longitudinal channel through the opening.

12. The method of claim 1, wherein the body comprises a suction port coupled to a suction source.

13. The method of claim 12, comprising providing suction from the suction source, wherein the step of directing the suction flow through the input port and the step of directing the flow of matter through one or more of the intake ports uses suction provided by the suction source.

14. The method of claim 1, wherein the body comprises a pressurized gas port configured to receive a pressurized gas.

15. The method of claim 14, comprising providing a pressurized gas, wherein the pressurized. gas generates suction through the Coanda effect as the pressurized gas passes through the body, and wherein the step of directing the suction flow through the input port and the step of directing the flow of matter through one or more of the intake ports uses suction provided by the Coanda effect.

16. The method of claim 1, wherein the input port comprises one or more scalloped edges.

17. The method of claim 16, wherein the one or more intake ports are positioned on the input port.

18. The method of claim 1, wherein the flow of matter comprises a flow of surgical smoke.

19. The method of claim 1, wherein the body comprising one or more filters positioned to receive a flow of matter from the one or more intake ports.

20. The method of claim 1, wherein the body comprises
a. suction control configured to open or close at least one of the one or more intake ports.

21. The method of claim 1, wherein the input port is configured to couple with a suction nozzle.

22. The method of claim 1, wherein body is configured so that the electrosurgical instrument is operable when coupled with the body.

23. The method of claim 22, wherein the body is configured to be operable simultaneously with the electrosurgical instrument when coupled with the electrosurgical instrument.

24. The method of claim 1, wherein the one or more intake ports in fluid communication with the narrow segment directly open into the narrow segment.

* * * * *

UNITED STATES PATENT AND TRADEMARK OFFICE
CERTIFICATE OF CORRECTION

PATENT NO. : 9,867,913 B2
APPLICATION NO. : 14/945367
DATED : January 16, 2018
INVENTOR(S) : Noah Mark Minskoff et al.

It is certified that error appears in the above-identified patent and that said Letters Patent is hereby corrected as shown below:

In the Claims

Column 48, Claim 1, Line 42, please replace "flud" with "fluid"

Signed and Sealed this
Twenty-fifth Day of September, 2018

Andrei Iancu
*Director of the United States Patent and Trademark Office*